US011382970B2

(12) United States Patent
Fettelschoss et al.

(10) Patent No.: US 11,382,970 B2
(45) Date of Patent: *Jul. 12, 2022

(54) TREATMENT OF INSECT BITE HYPERSENSITIVITY

(71) Applicant: UNIVERSITÄT ZÜRICH, Zürich (CH)

(72) Inventors: Antonia Fettelschoss, Münchwilen (CH); Martin Bachmann, Rämismühle (CH)

(73) Assignee: UNIVERSITAT ZURICH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/721,847

(22) Filed: Dec. 19, 2019

(65) Prior Publication Data
US 2020/0230231 A1    Jul. 23, 2020

Related U.S. Application Data

(63) Continuation of application No. 15/758,052, filed as application No. PCT/EP2016/071078 on Sep. 7, 2016, now Pat. No. 10,556,003.

(30) Foreign Application Priority Data

Sep. 8, 2015 (EP) .................................. 15184195
Apr. 21, 2016 (EP) .................................. 16166342
Jun. 20, 2016 (EP) .................................. 16175211

(51) Int. Cl.
A61K 39/385 (2006.01)
A61K 39/35 (2006.01)
A61P 17/00 (2006.01)
A61P 37/08 (2006.01)
A61P 17/02 (2006.01)
(Continued)

(52) U.S. Cl.
CPC .............. *A61K 39/35* (2013.01); *A61P 17/00* (2018.01); *A61P 17/02* (2018.01); *A61P 37/08* (2018.01); *C12N 7/00* (2013.01); A61K 2039/5258 (2013.01); A61K 2039/552 (2013.01); A61K 2039/58 (2013.01); C07K 14/54 (2013.01); C12N 2770/14023 (2013.01); C12N 2770/14034 (2013.01)

(58) Field of Classification Search
None
See application file for complete search history.

(56) References Cited

FOREIGN PATENT DOCUMENTS

WO    WO 03/040164    5/2003

OTHER PUBLICATIONS

Benarafa et al., "Cloning of equine chemokines eoxtaxin, monocyte chemoattractant protein (MCP)-1, MCP-2 and MCP-4, mRNA expression in tissues and induction by IL-4 in dermal fibroblasts," Veterinary Immunology and Immunopathology 76: 283-298 (2000).
(Continued)

*Primary Examiner* — M Franco G Salvoza
(74) *Attorney, Agent, or Firm* — Medier Ferro Woodhouse & Mills PLLC

(57) ABSTRACT

The present invention relates to compositions, immunogenic or vaccine compositions and pharmaceutical compositions for the prevention or treatment of insect bite hypersensitivity of equine mammals, preferably of horses. Furthermore, the invention provides methods for preventing or treating insect bite hypersensitivity of equine mammals, preferably of horses.

24 Claims, 28 Drawing Sheets
Specification includes a Sequence Listing.

(51) Int. Cl.
   *C12N 7/00*    (2006.01)
   *C07K 14/54*   (2006.01)
   *A61K 39/00*   (2006.01)

(56) References Cited

OTHER PUBLICATIONS

Benarafa et al., "Role of the chemokine eotaxin in the pathogenesis of equine sweet itch," Veterinary Record 151(23): 691-693 (2002) (British Veterinary Association, London, GB).
Cunningham et al., "Cloning, expression and biological activity of equine interleukin (IL)-5," Veterinary Immunology and Immunopathology 95(1-2):63-72 (2003).
Cunningham et al., "Equine recurrent airway obstruction and insect bite hypersensitivity: Understanding the diseases and uncovering possible new therapeutic approaches," The Veterinary Journal 177(3):334-344 (2008) (Bailliere Tindall, London, GB).
Plummer et al., "Viral nanoparticles and virus-like particles: platforms for contemporary vaccine design," WIRES Nanomed and Nanobiotechnol 3(2):174-196 (2011).
Scaffartzik et al., "Equine insect bite hypersensitivity: What do we know?", Veterinary Immunology and Immunopathology 147: 113-126 (2012).
Jonsdottir et al., "Developing a preventative immunization approach against insect bite hypersensitivity using recombinant allergens: A pilot study," Veterinary Immunology and Immunopathology 166: 8-21 (2015).
Vandergrifft et al., NCBI Genbacnk Accession No. AAB51382.1 (1997).
Zou et al., "Combined vaccination against IL-5 and eotaxin blocks eosinophilia in mice," Vaccine 28(18):3192-3200 (2010).
The International Search Report issued in International Application No. PCT/EP2016/071078 dated Dec. 1, 2016.
Benarafa et al., "Role of the chemokine eotaxin in the pathogenesis of equine sweet itch," Vet Rec. 151(23):691-3 (2002).
Panina-Bordignon et al., "Universally immunogenic T cell epitopes: promiscuous binding to human MHC class II and promiscuous recognition by T cells," Eur J Immunol. 19(12):2237-42 (1989).
Petersen et al., "Effects of dexamethasone and hydroxyzine treatment on intradermal testing and allergen-specific IgE serum testing results in horses," Vet Dermatol. 20(5-6):615-22 (2009).
Sette et al., "Structural analysis of peptides capable of binding to more than one Ia antigen," J Immunol. 142(1):35-40 (1989).

TREATMENT OF INSECT BITE HYPERSENSITIVITY

REFERENCE TO AN ELECTRONIC SEQUENCE LISTING

The contents of the electronic sequence listing (0192_0048US1_SL.txt; Size: 46 KB; and Date of Creation: Dec. 19, 2019) is herein incorporated by reference in its entirety.

The present invention relates to compositions, immunogenic or vaccine compositions and pharmaceutical compositions for the prevention or treatment of insect bite hypersensitivity of equine mammals, preferably of horses. Furthermore, the invention provides methods for preventing or treating insect bite hypersensitivity of equine mammals, preferably of horses.

RELATED ART

Insect bite hypersensitivity (IBH), also known as "sweet itch" or "summer eczema", is the most common allergic skin disease of equine mammals, in particular horses, and manifests as a chronic relapsing seasonal allergic dermatitis caused by the bites of insects of the genus *Culicoides* found in various areas of the world. Various studies have suggested IBH to be associated with IgE-mediated reactions against salivary gland proteins from *Culicoides*. Moreover, recent studies suggest that IBH is characterized by an imbalance between a T helper 2 (Th2) and regulatory T cell ($T_{reg}$) immune response (Schaffartzik A., et al., Vet Immunol Immunopathol, 2012, 147:113-126). During the last decade several studies have demonstrated that the salivary gland proteins of *Culicoides* are recognized by IgE of IBH-affected horses (Hellberg, W., et. al., 2006, Vet Immunol Immunopathol 113:99-112). Up to date, more than 700 *Culicoides* species have been identified of which 130 are blood feeding species (Van Grevenhof, E. M., et. al., 2007, Equine Vet J 36:69-73).

Worldwide, approximately 5-10% of horses are affected by IBH (Bjornsdottir, S., et al., 2006, Acta Vet. Scand. 48:3). Great Britain's prevalence is approximately 3%, in Germany about 38% and in Queensland, Australia it is about 60% (Anderson, G. S., et al., 1996, J. Med. Entomol. 33:458-466; Littlewood, J. D., et al., 1998, Vet. Rec. 142, 66-67; and references cited therein). In principal all breeds can be affected, however, disease has been described for Quarter horses, Thoroughbreds, Arabian horses, Warmbloods, Draft horses, Friesian horses, Shire horses, different pony breeds and Icelandic horses (Van Grevenhof, E. M., et. al., 2007, Equine Vet J 36:69-73 and references cited therein).

Clinical signs of IBH derive from intense pruritus caused by hypersensitivity reactions to bites of blood feeding insects. The disease is initially characterized by numerous papules, tufted hair, hyperesthesia, and skin sensitization followed by scratching and rubbing. This self trauma leads to localized hair loss and excoriations which contribute to the perpetuation of secondary infections. If the disease progresses and becomes chronic, it may lead to fibrosis, hypertrophy of epidermal tissue, and marked hyperkeratosis and lichenification, visible in thickening of the skin, scaling, formation of transverse ridges and folds (Schaffartzik A., et al., Vet Immunol Immunopathol, 2012, 147:113-126). Moreover, the presence of *Culicoides* antigens in the skin of affected animals induces inflammatory cell infiltration, with early eosinophil accumulation followed by T cell recruitment. The T cell cytokine profile in IBH lesions has not been extensively studied although increased interleukin IL-4, IL-5 and IL-13 mRNA expression in acute lesions and increased chemokine CCL11 (eotaxin) and CCL2 mRNA expression has been reported in established lesions (Cunningham, F. M., et al. 2008, Vet. J. 177:334-344; Benarafa, C. et al., 2002, Vet Rec 151: 691-693).

Due to the preferred feeding sites of the insects, the lesions are mostly located along the dorsal midline, at the base of the mane and tail, and/or along the ventral midline and, occasionally, at the ears. IBH-affected horses show seasonal manifestation with a gradual progression in severity of the signs over time. Clinical signs appear during the warmer months from spring to autumn when *Culicoides* are active and regress during the winter in the absence of exposure but in severe chronic cases, clinical signs may also persist during winter response (Schaffartzik A., et al., Vet Immunol Immunopathol, 2012, 147:113-126).

In the past, different approaches for treatment of IBH have been described, but, at present, the only safe and effective method is the avoidance of *Culioides* allergens. Avoidance or reduced allergen exposure is attempted to be achieved by mechanical protection with blankets representing the most common treatment of IBH (Olsen, L., et al., 2010, Vet. J. 187:347-351). Beside blankets horses are kept in stables in an insect-proof environment from midafternoon to midmorning or relocated to other parts where the occurrence of *Culioides* is highly reduced.

Insect repellents are also applied to keep blood-sucking insects away from horses. Moreover, glucocorticosteroids are further used for symptomatic treatment of IBH (Petersen, A., et. al., 2009, Vet. Dermatol. 20:615-622). Severely affected horses, particularly those with marked pruritus may need anti-inflammatory treatment with systemic steroids. The disadvantages of glucocorticosteroids in long-term treatments are the toxic side-effects, e.g. immunosuppression, muscular atrophy, osteoporosis and laminitis (Cunningham, F. M., et al. 2008, Vet. J. 177:334-344).

Allergen-specific immunotherapy (SIT), usually the subcutaneous administration of allergen extract, is effectively used in human and small animal dermatology, conferring long-term benefit. There are not many reports describing experimental applications of SIT in horses. However, controversial results of the efficacy have been reported for SIT with whole body extract (WBE) of *Culioides*. In an immunotherapy trial IBH-affected horses were injected subcutaneously with WBE. Weekly injections during the first year reduced the clinical signs in 90% of IBH-affected horses (Anderson et al., 1996). 37.5% of these horses were completely free from clinical signs after two years of immunotherapy, whereas 62.5% had moderately to significantly reduced clinical signs (Anderson et al., 1996). Conversely, a randomized, double-blinded, placebo-controlled clinical study did not show any improvement in the health status in IBH-affected horses after SIT over a six-month period (Barbet et al., 1990). In conclusion and in contrast to human allergy, SIT in horses is not yet established and other long-term curative treatments do not exist.

As a consequence, there is currently no satisfactory treatment of IBH (Cunningham, F. M., et al. 2008, Vet. J. 177:334-344; Schaffartzik A. et al., Vet Immunol Immunopathol, 2012, 147:113-126).

SUMMARY OF THE INVENTION

We have now surprisingly found that compositions of the present invention are effective for the prevention and treatment of insect bite hypersensitivity (IBH) in equine mammals, in particular in horses. Thus, we have found that administration of the compositions of the present invention to horses led to an efficient reduction of IBH disease parameters and symptoms. In particular, we have shown that administration of the compositions of the present invention to horses not only led to the induction of auto-antibodies and reduction of eosinophil levels in blood and skin of the horses, but furthermore said reduction of eosinophil levels correlate with reduction of IBH disease symptoms. Moreover, we have shown that administration of the compositions of the present invention to horses led to an efficient reduction of the severity grade of skin lesions of the horses affected with IBH.

Thus, in a first aspect, the present invention provides for a composition comprising: (a) a core particle with at least one first attachment site; and (b) at least one antigen with at least one second attachment site, wherein said at least one antigen is (i) an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; or (ii) an equine Eotaxin antigen (eEotaxin antigen), wherein said eEotaxin antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6; (iii) an equine Interleukin-31 antigen (eIL-31 antigen), wherein said eIL-31 antigen comprises, or preferably is, a protein with the amino sequence selected from SEQ ID NO:12 or a protein with an amino acid sequence of at least 90%, preferably of at least 92%, further preferably of at least 95%, and again further preferably of at least 98% amino acid sequence identity with SEQ ID NO:12;

wherein (a) and (b) are linked through said at least one first and said at least one second attachment site via at least one non-peptide covalent bond.

In a preferred embodiment, said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5.

In another preferred embodiment, said at least one antigen is an equine Eotaxin antigen (eEotaxin antigen), wherein said eEotaxin antigen comprises, or preferably is, a protein with the amino sequence selected from SEQ ID NO:6, SEQ ID NO:7, SEQ ID NO:10.

In another preferred embodiment said at least one antigen is an equine Interleukin-31 antigen (eIL-31 antigen), wherein said eIL-31 antigen comprises, or preferably is, a protein with the amino sequence selected from SEQ ID NO:12, SEQ ID NO:14.

In another preferred embodiment, said core particle is a virus-like particle (VLP) wherein said VLP is a VLP of RNA bacteriophage Qβ, and said VLP comprises, consists essentially of, or alternatively consists of, recombinant coat proteins of RNA bacteriophage Qβ, and wherein said recombinant coat proteins comprising or preferably consisting of SEQ ID NO:31.

In a further preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. Preferably said T helper cell epitope replaces a N-terminal region of said CMV polypeptide, and wherein said N-terminal region of said CMV polypeptide corresponds to amino acids 2-12 of SEQ ID NO: 15. A preferred Th cell epitope is a PADRE sequence, and wherein said Th cell epitope comprises, preferably consists of, the amino acid sequence of SEQ ID NO:19; or wherein said Th cell epitope is derived from tetanus toxin, and wherein said Th cell epitope has, preferably consists of, the amino acid sequence of SEQ ID NO:18. Thus, in a very preferred embodiment, said modified CMV polypeptide comprises, preferably consists of, an amino acid sequence of SEQ ID NO:20 or SEQ ID NO:21.

In a further aspect, the present invention provides for an immunogenic or vaccine composition comprising an effective amount of the inventive, optionally said immunogenic or vaccine composition further comprises an adjuvant.

In a further aspect, the present invention provides for a pharmaceutical composition comprising: (a) the inventive composition or the inventive immunogenic or vaccine composition; and (b) a pharmaceutically acceptable carrier.

In a further aspect, the present invention provides for a method of immunization, wherein said method comprises administering the inventive composition, the inventive immunogenic or vaccine composition or the inventive pharmaceutical composition to an equine mammal, preferably to a horse.

In a further aspect, the present invention provides for the inventive composition, the inventive immunogenic or vaccine composition, or the inventive pharmaceutical composition for use as a medicament.

In a further aspect, the present invention provides for the inventive composition, the inventive immunogenic or vaccine composition, or the inventive pharmaceutical composition for use in a method of prevention or treatment of insect bite hypersensitivity of an equine mammal, preferably of a horse, wherein an effective amount of said inventive composition, said inventive immunogenic or vaccine composition, or said inventive pharmaceutical composition is administered to said equine mammal, preferably to said horse. Preferably, said administration of said inventive composition, said inventive immunogenic or vaccine composition, or said inventive pharmaceutical composition reduces at least one IBH parameter or symptom when compared to said at least one IBH parameter or symptom before said administration, and wherein preferably said at least one IBH parameter or symptom is the level or severity grade of skin lesions, and wherein further preferably said reduction of said level or severity grade of skin lesions is determined by a symptom lesion scoring test, typically and preferably as described in Example 13.

In a further aspect, the present invention provides for a method of prevention or treatment of insect bite hypersensitivity, wherein said method comprises administering an effective amount of said inventive composition, said inventive immunogenic or vaccine composition, or said inventive pharmaceutical composition to an equine mammal, preferably to a horse.

In another aspect, the present invention provides for the of said inventive composition, said inventive immunogenic or vaccine composition, or said inventive pharmaceutical composition for the manufacture of a medicament for the prevention or treatment of insect bite hypersensitivity, wherein typically and preferably an effective amount of said inventive composition, said inventive immunogenic or vaccine composition, or said inventive pharmaceutical composition is administered to an equine mammal, preferably to a horse.

In a further aspect, the present invention provides for an immunogenic or vaccine composition comprising an effective amount of a first composition and an effective amount of a second composition, wherein said first composition comprises (a) a first core particle with at least one first attachment site; and (b) at least one first antigen with at least one second attachment site, wherein said at least one first antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein said second composition comprises (c) a second core particle with at least one first attachment site; and (d) at least one second antigen with at least one second attachment site, wherein said at least one second antigen is an equine Eotaxin antigen (eEotaxin antigen), wherein said eEotaxin antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6; and wherein (a) and (b) are linked through said at least one first and said at least one second attachment site via at least one non-peptide covalent bond, and wherein (c) and (d) are linked through said at least one first and said at least one second attachment site via at least one non-peptide covalent bond; and wherein optionally said immunogenic or vaccine composition further comprises an adjuvant.

Samples from various stages of the inclusion body preparation and purification were applied to a 4-12% Bis-Tris Gel (NuPAGE, Novex, Invitrogen Life Technologies) and run under reducing conditions. Proteins were stained with Coomassie blue. Lane M, Size Marker (See Blue, prestained, NuPAGE, Novex, Invitrogen Life Technologies), lane 1, Lysate (sample A), lane 2, soluble fraction (sample B), lane 3, flow through (unbound material, sample D), lane 4, pooled eluate from Ni-NTA column (sample E).

Figure 5:
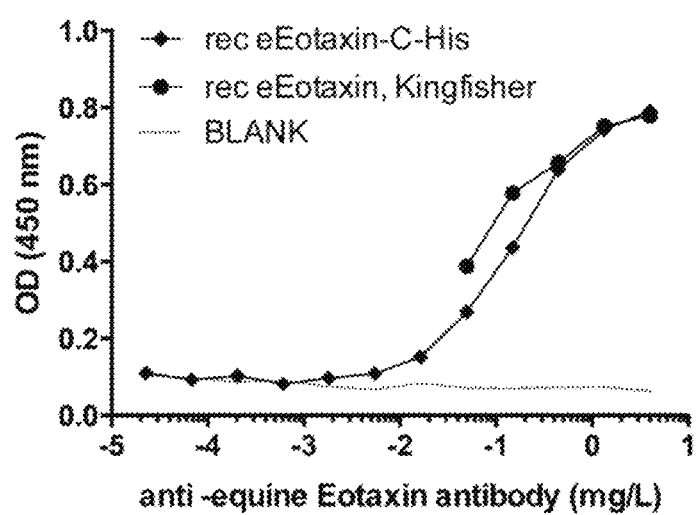

FIG. 5: Correct structure of refolded recombinant eEotaxin-C-His. eEotaxin-C-His can be detected by a commercially available anti-eEotaxin antibody. Anti-His antibody coated ELISA plates were incubated with recombinantly expressed and refolded eEotaxin-C-His and detected by a commercially available anti-Eotaxin antibody that recognizes equine Eotaxin.

Figure 6:
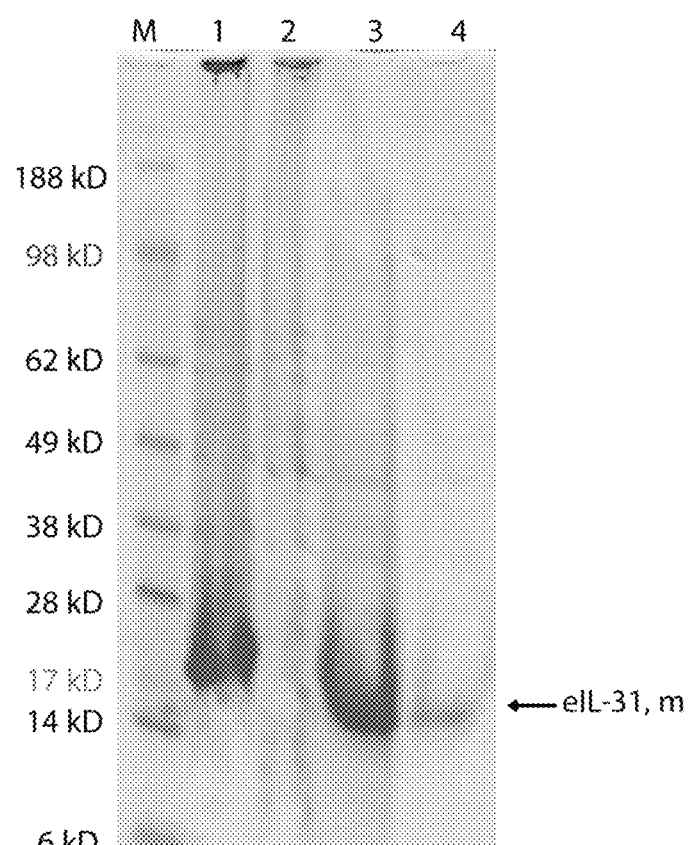

FIG. 6: SDS-PAGE refolded recombinant eIL-31-C-His.

Samples from various stages of the inclusion body preparation and purification were applied to a 4-12% Bis-Tris Gel (NuPAGE, Novex, Invitrogen Life Technologies) and run under reducing conditions. Proteins were stained with Coomassie blue. Lane M, Size Marker (See Blue, prestained, NuPAGE, Novex, Invitrogen Life Technologies), lane 1, Lysate (sample A), lane 2, soluble fraction (sample B), lane 3, solubilized inclusion bodies (sample C), lane 4, eIL-31 monomer (eIL-31, m) eluate from Ni-NTA column (sample E).

Figure 7:
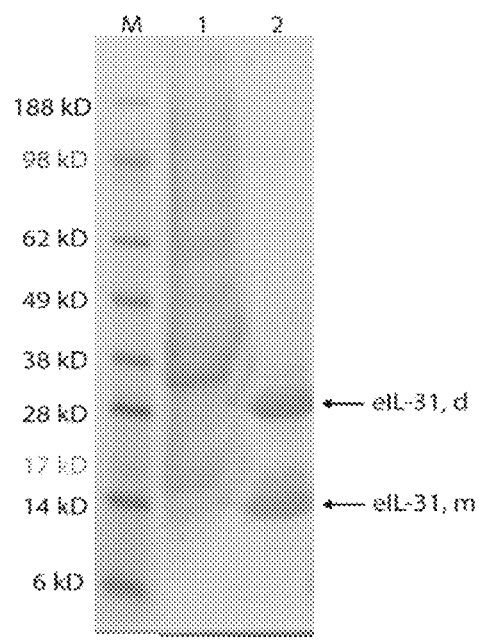

FIG. 7: Correct structure of refolded recombinant eIL-31-C-His.

Protein was refolded and concentrated as described above. An aliquote was separated on a 4-12% Bis-Tris Gel (NuPAGE, Novex, Invitrogen Life Technologies) and run under native conditions (+SDS, no DTT, no heating). Proteins were stained with Coomassie blue. Lane M, Size Marker (See Blue, prestained, NuPAGE, Novex, Invitrogen Life Technologies), lane 1, pooled eluate from Ni-NTA column, lane 2, refolded eIL-31-C-His.

Figure 8:
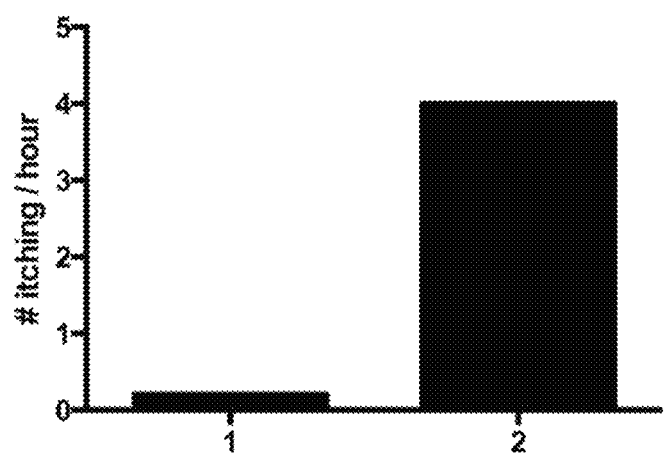

FIG. 8: Biological activity of recombinant refolded equine eIL-31-C-His. Number of itching on injection site. Bar 1, eIL-5-C-His control, bar 2, eIL-31-C-His.

Figure 9:
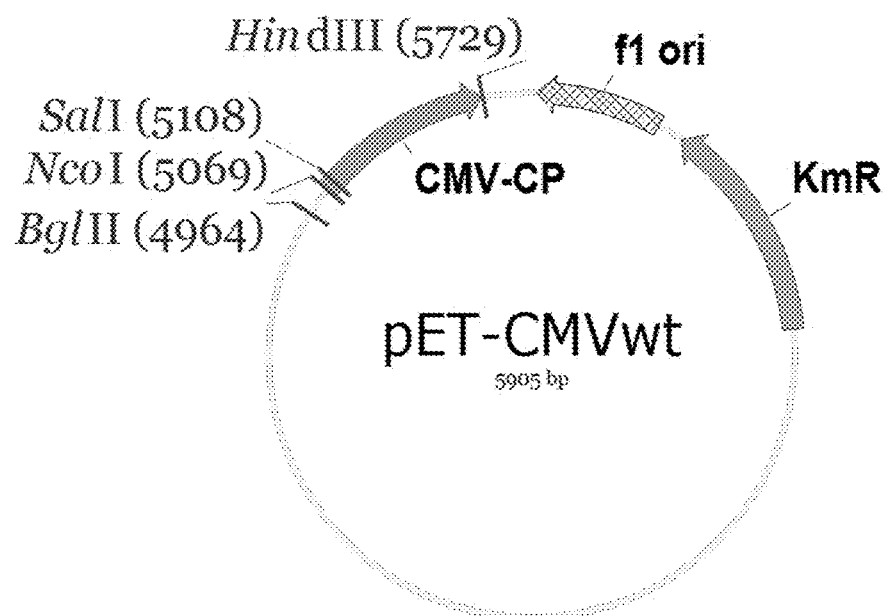

FIG. 9: pET-CMVwt plasmid map. The relative positions of all relevant genes and restriction enzyme sites are denoted.

Figure 10A:
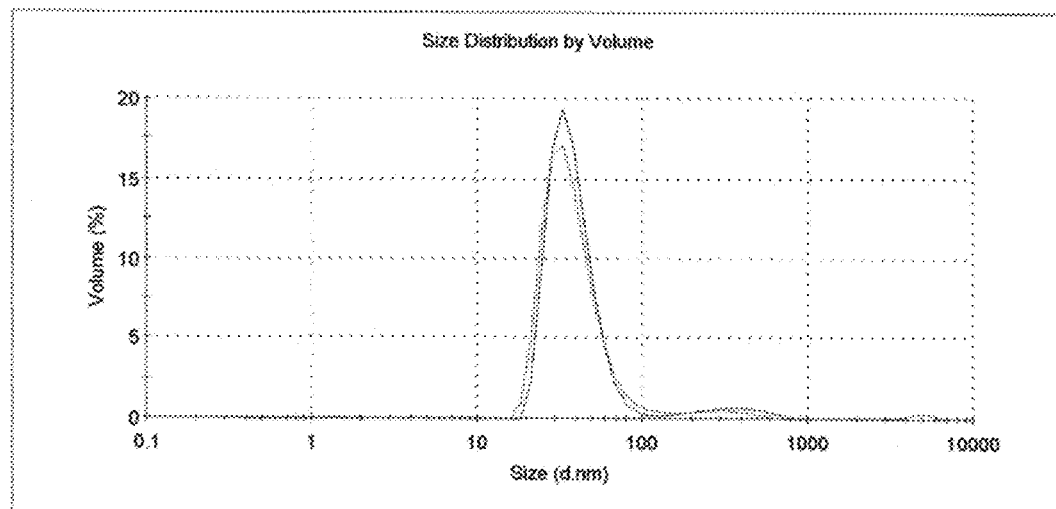

FIG. 10A: Dynamic light scattering of purified CMVwt VLPs. The size of particles was detected by using Zetasizer Nano ZS (Malvern Instruments Ltd., United Kingdom).

Figure 10B:
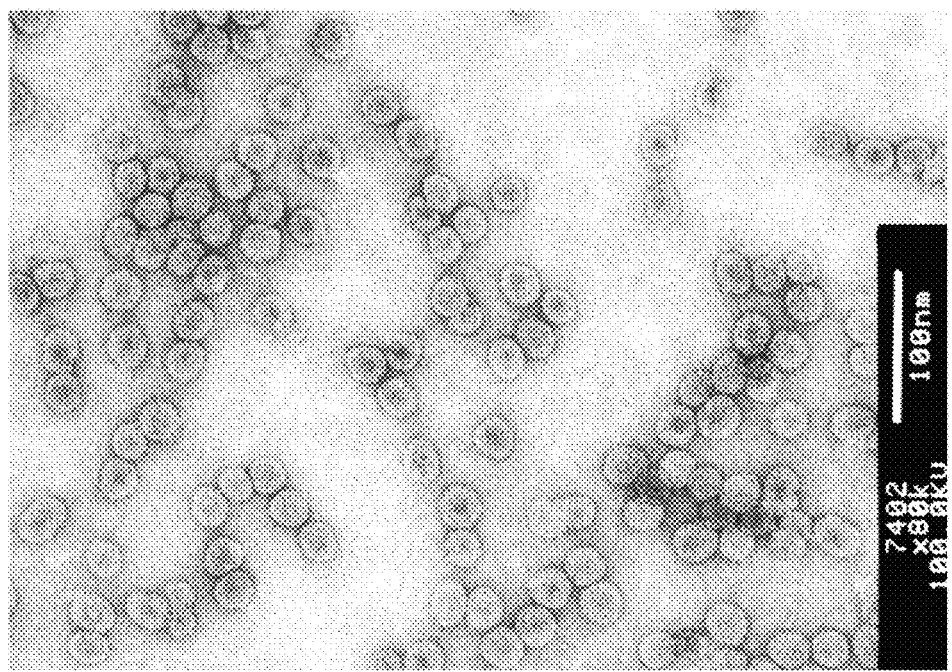

FIG. 10B: Electron-microscopy analysis of purified CMVwt VLPs. For the morphological analysis of VLPs the JEM-1230 electron microscope (Jeol Ltd., Tokyo, Japan) was used.

Figures 11A, 11B:
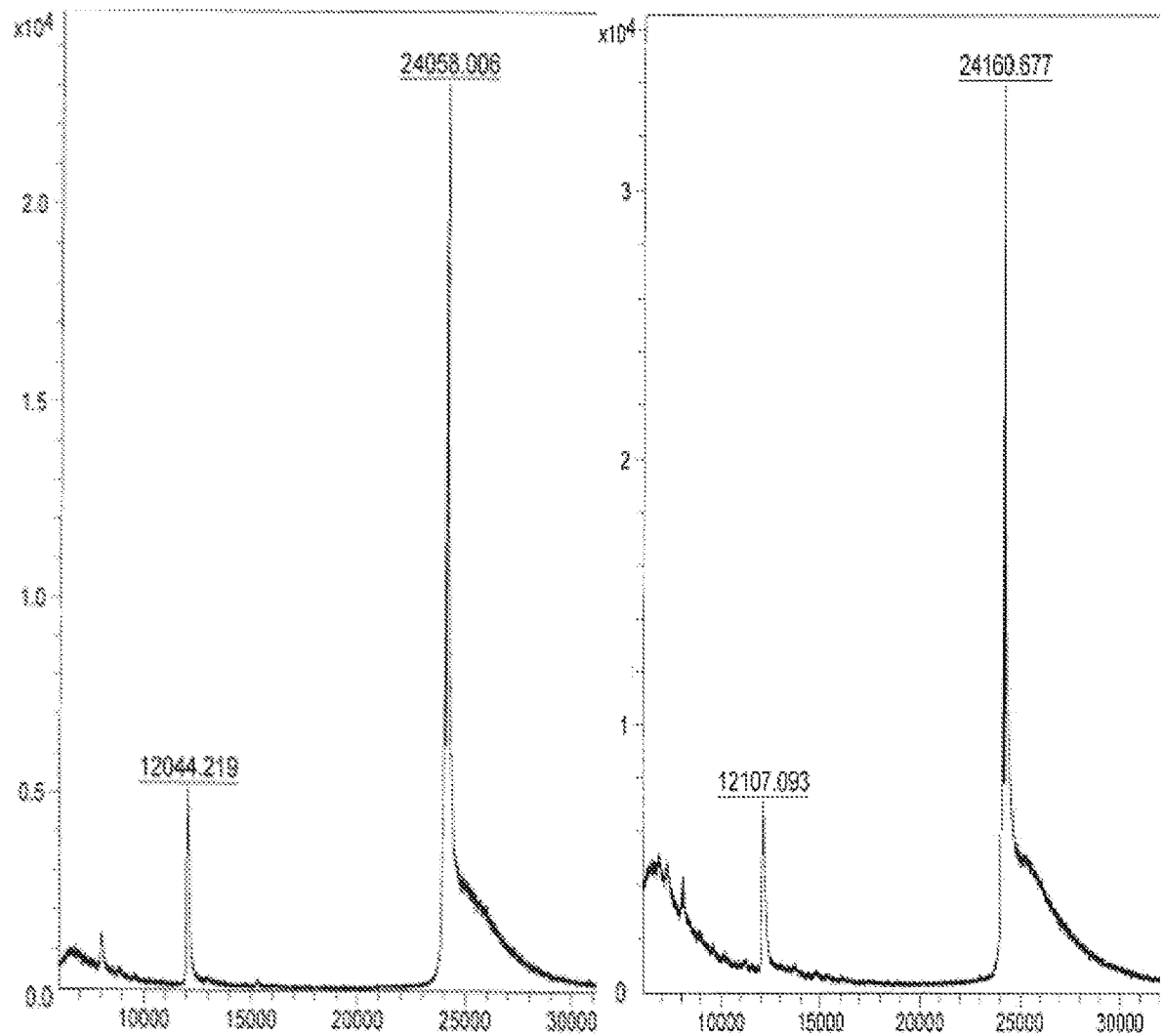
Figure 11C:
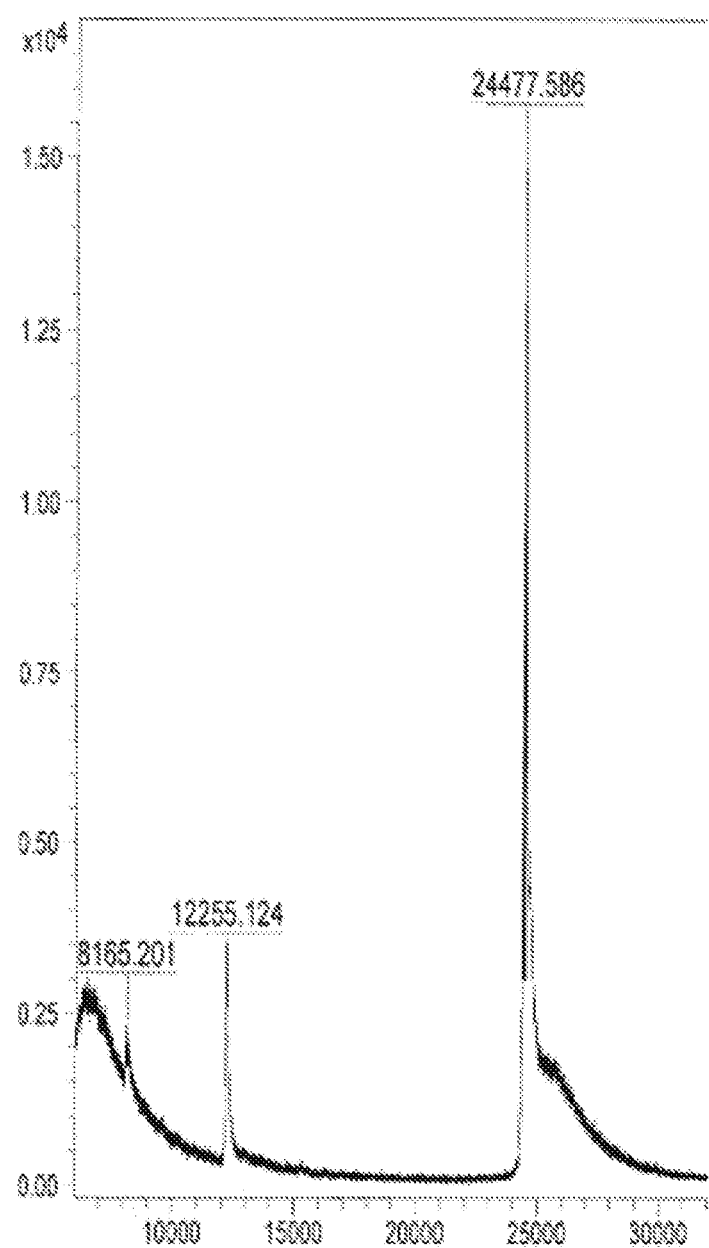

FIGS. 11A, 11B, and 11C: Mass spectrometric analysis of purified CMV-derived VLPs.

Matrix-assisted laser desorption/ionization (MALDI)-TOF MS analysis was carried out on an Autoflex MS (Bruker Daltonik, Germany). The protein molecular mass (MM) calibration standard II (22.3-66.5 kDa; Bruker Daltonik) was used for mass determination.

FIG. 11A: CMVwild-type ("wt"); theoretical MM=24069; found MM=24058

FIG. 11B: CMV-Npadr; theoretical MM=24161 (without first Met); found MM=24160

FIG. 11C: CMV-Ntt830; theoretical MM=24483 (without first Met); found MM=24477

Figure 12A:
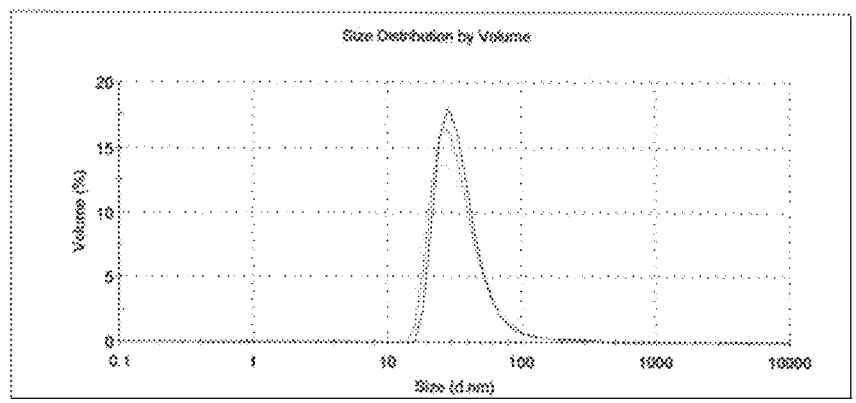

FIG. 12A: Dynamic light scattering of purified CMV-Ntt830 VLPs. The size of particles was detected by using Zetasizer Nano ZS (Malvern Instruments Ltd., United Kingdom).

Figure 12B:
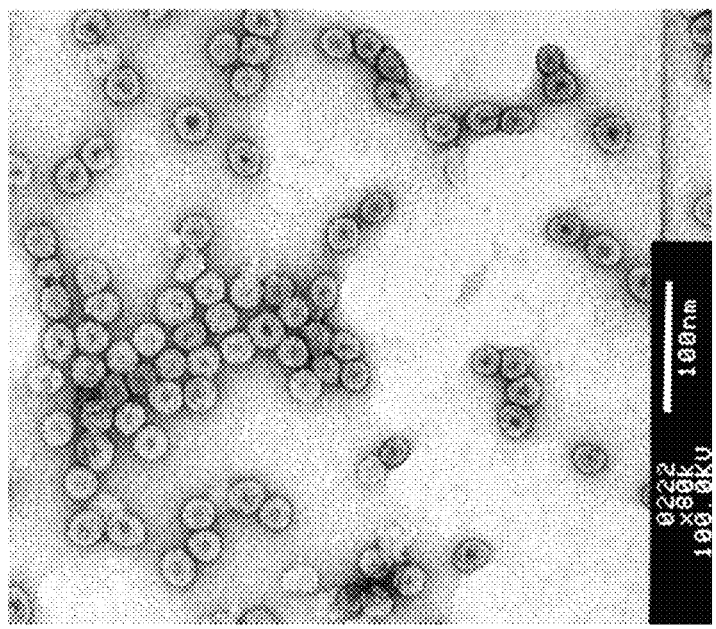

FIG. 12B: Electron-microscopy analysis of purified CMV-Ntt830 VLPs. For the morphological analysis of VLPs the JEM-1230 electron microscope (Jeol Ltd., Tokyo, Japan) was used.

Figure 13A:
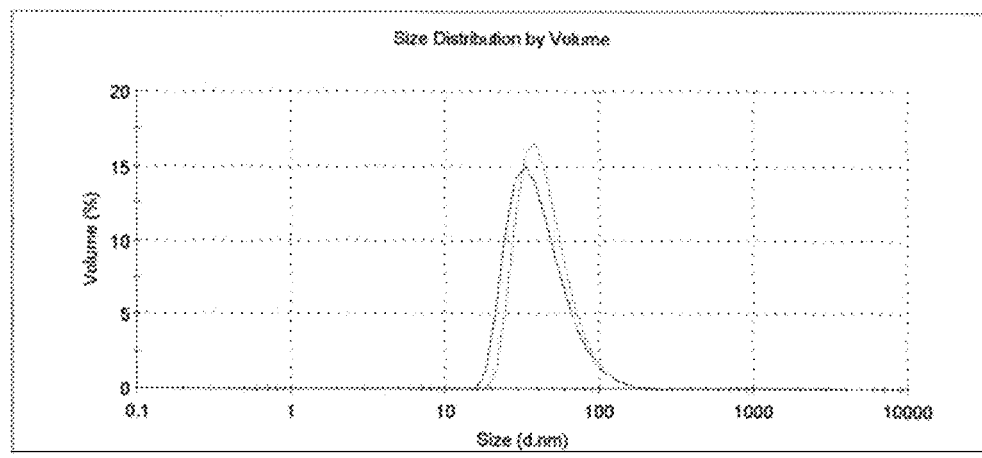

FIG. 13A: Dynamic light scattering of purified CMV-Npadr VLPs. The size of particles was detected by using Zetasizer Nano ZS (Malvern Instruments Ltd., United Kingdom).

Figure 13B:
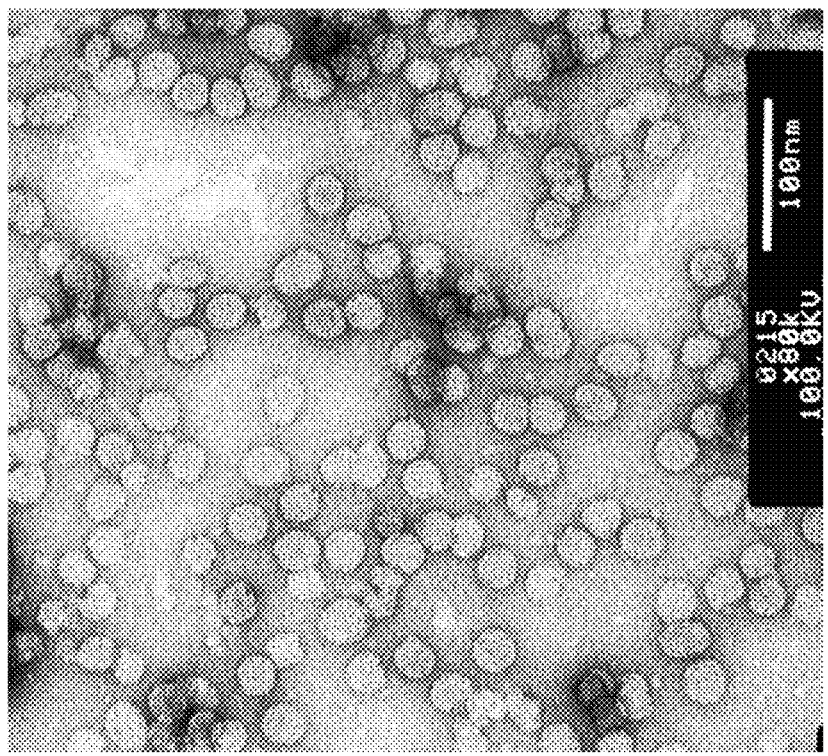

FIG. 13B: Electron-microscopy analysis of purified CMV-Npadr VLPs. For the morphological analysis of VLPs the JEM-1230 electron microscope (Jeol Ltd., Tokyo, Japan) was used.

Figure 14A:
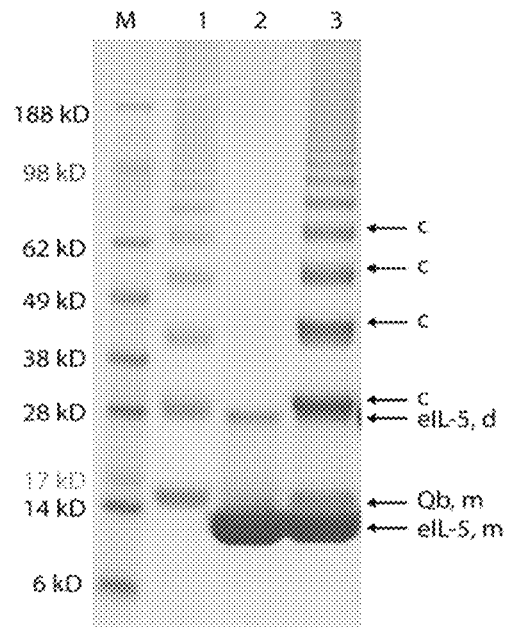

FIG. 14A: Analysis of coupling reaction of eIL-5-C-His-Qβ. By SDS-PAGE. Proteins were stained with Coomassie blue: eIL-5 monomer (eIL-5, m), eIL-5 dimer (eIL-5, d), Qβ monomer (Qβ, m) coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-5-C-His, lane 3, eIL-5-C-His-Qβ coupling reaction.

Figure 14B:
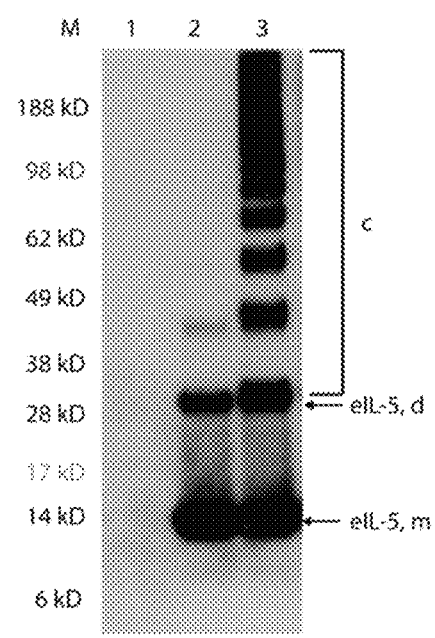

FIG. 14B: Analysis of coupling reaction of eIL-5-C-His-Qβ. By Western-blot. Stained with α-His antibody: eIL-5 monomer (eIL-5, m), eIL-5 dimer (eIL-5, d), coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-5-C-His, lane 3, eIL-5-C-His-Qβ coupling reaction.

Figure 15A:
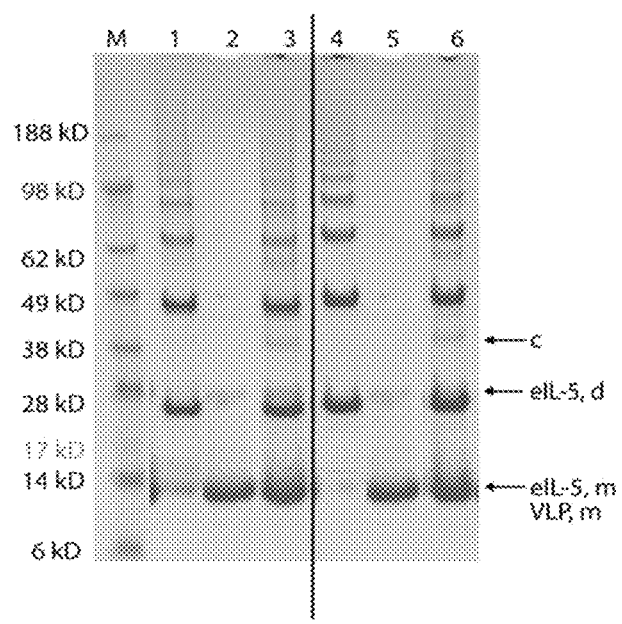

FIG. 15A: Analysis of coupling reaction of eIL-5-C-His to VLPs CMV-Npadr and CMVtt830. By SDS-PAGE. Proteins were stained with Coomassie blue: eIL-5 monomer (eIL-5, m), eIL-5 dimer (eIL-5, d), VLP (VLP, m), coupling (c). Lane M, Size Marker (See Blue, prestained, NuPAGE, Novex, Invitrogen Life Technologies), lane 1, CMV-Npadr-VLP after derivatization with the chemical crosslinker SMPH, lane 2, TCEP activated eIL-5-C-His, lane 3, eIL-5-C-His-CMV Npadr coupling reaction, lane 4, CMVtt830-VLP after derivatization with the chemical crosslinker SMPH, lane 5, TCEP activated eIL-5-C-His, lane 6, eIL-5-C-His-CMVtt830 coupling reaction.

Figure 15B:
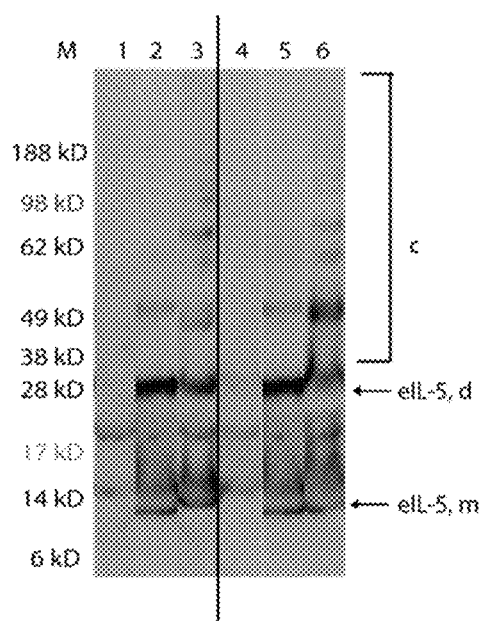

FIG. 15B: Analysis of coupling reaction of eIL-5-C-His to VLPs CMV-Npadr and CMVtt830. By Western-blot. Stained with α-His antibody: eIL-5 monomer (eIL-5, m), eIL-5 dimer (eIL-5, d), coupling (c). Lane M, Size Marker (See Blue, prestained, NuPAGE, Novex, Invitrogen Life Technologies), lane 1, CMV-Npadr-VLP after derivatization with the chemical crosslinker SMPH, lane 2, TCEP activated eIL-5-C-His, lane 3, eIL-5-C-His-CMV Npadr coupling reaction, lane 4, CMVtt830-VLP after derivatization with the chemical crosslinker SMPH, lane 5, TCEP activated eIL-5-C-His, lane 6, eIL-5-C-His-CMVtt830 coupling reaction.

FIG. 16A: ELISA of Antibody titer in mice. Sera from mice. Pre-immune sera (dotted line) and day 21 sera from mice vaccinated with eIL5-C-His-Qβ were collected and analyzed by ELISA for antibodies against eIL-5-C-His.

FIG. 16B: ELISA of Antibody titer in horses. Sera from horses. Pre-immune and day 56 sera of 5 horses immunized with eIL5-C-His-Qβ were collected and analyzed by ELISA for antibodies against eIL-5-C-His. Horses have been immunized on day 0, 21, and 42. Data shows day 56 sera subtracted by pre-immune values.

FIG. 16C: ELISA of Antibody titer in horses. Sera from horses. Pre-immune and serum after 1st, 2nd, and 3rd vaccination of eIL-5-C-His-CMV-Ntt830 of a single horse was collected and sera were analyzed for antibodies against eIL-5. The horse has been immunized on day 0, 21, and 42. Data shows day 14, 35, and 56 sera subtracted by pre-immune values.

FIG. 16D: ELISA of Antibody titer in horses. Sera from horses. Pre-immune and serum after 1st, 2nd, and 3rd vaccination of eIL-5-C-His-CMV-Ntt830 of a single horse was collected and sera were analyzed for antibodies against CMV-Ntt830. The horse has been immunized on day 0, 33, and 53. Data shows day 16, 51, and 67 sera subtracted by pre-immune values.

FIG. 16E: ELISA of Antibody titer in horses. Sera from horses. Pre-immune and serum after 3rd vaccination (day 84) of eIL-5-C-His-CMV-Ntt830 of four horses was collected and sera were analyzed for antibodies against eIL-5. Horses have been immunized on day 0, 28, and 56. Data shows day 84 sera subtracted by pre-immune values.

FIG. 17A: Correlation of disease symptoms to eosinophil levels in blood. Eosinophil levels of 12 sweet itch affected horses were measured in the blood and were blotted against disease symptom scoring of IBH lesions during the season. Correlation precision is shown by $R^2=0.9227$, $p<0.0001$, n=12.

FIG. 17B. Correlation of disease symptoms to eosinophil levels in blood. Eosinophil levels of 48 sweet itch affected horses were measured in the blood and were blotted against disease symptom scoring of IBH lesions during the season. Correlation precision is shown by $R^2=0.3115$, $p<0.0001$, n=48.

FIG. 18A: Efficient reduction of IBH disease parameters by eIL-5-C-His-Qβ. Time course of antibody titer. Blood samples have been collected at several time points post injections (indicated by arrows) and sera were analyzed for anti-eIL-5 IgG self-antibodies.

FIG. 18B: Efficient reduction of IBH disease parameters by eIL-5-C-His-Qβ. Time course of eosinophil levels in blood. Blood samples have been collected at several time points post injections (indicated by arrows) and EDTA-blood samples were analyzed.

FIG. 18C: Efficient reduction of IBH disease parameters by eIL-5-C-His-Qβ. Disease lesion time course. Severity grades of lesions on tail and mane were recorded over time.

FIG. 18D: Efficient reduction of IBH disease parameters by eIL-5-C-His-Qβ. Correlation of antibody titer versus eosinophil levels. IgG anti-eIL-5 antibody response was correlated to eosinophil levels.

FIG. 18E: Efficient reduction of IBH disease parameters by eIL-5-C-His-CMVtt830. Time course of antibody titer. Blood samples have been analyzed for anti-eIL-5 (black line) and anti-CMVtt830 IgG antibodies (grey line). Blood samples have been collected at several time points post injections (indicated by arrows, day 0, 33, 53) and sera (day 0, 16, 51, 67) were analyzed for anti-eIL-5 IgG self-antibodies and anti-CMVtt830 antibodies.

FIG. 18F: Efficient reduction of IBH disease parameters by eIL-5-C-His-CMVtt830. Time course of eosinophil levels in blood (black line) and total lesion severity (grey line). Blood samples have been collected and EDTA-blood samples were analyzed. Vaccine injections on day 0, 33, 53 are indicated by arrows.

Figure 18A:
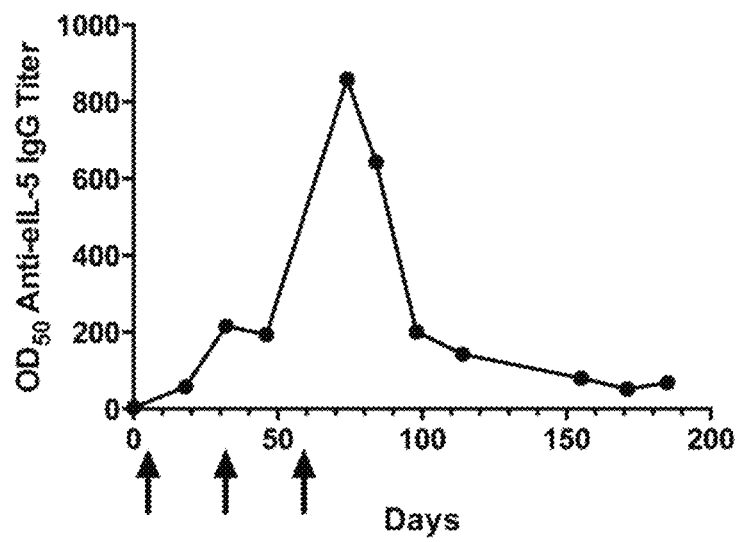
Figure 18B:
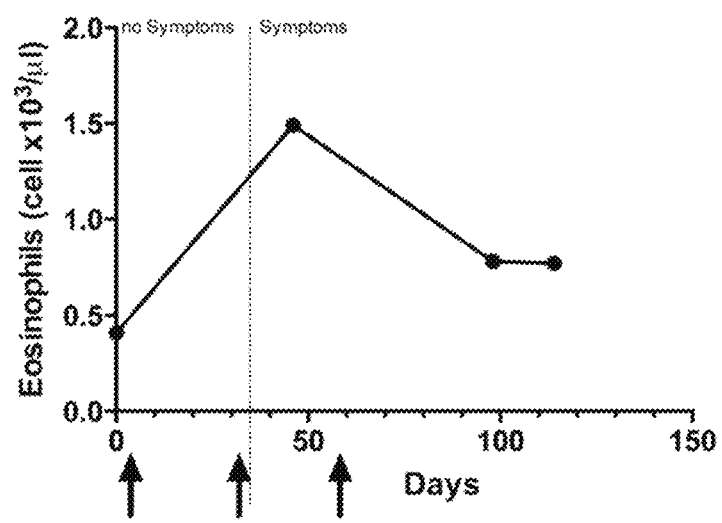
Figure 18C:
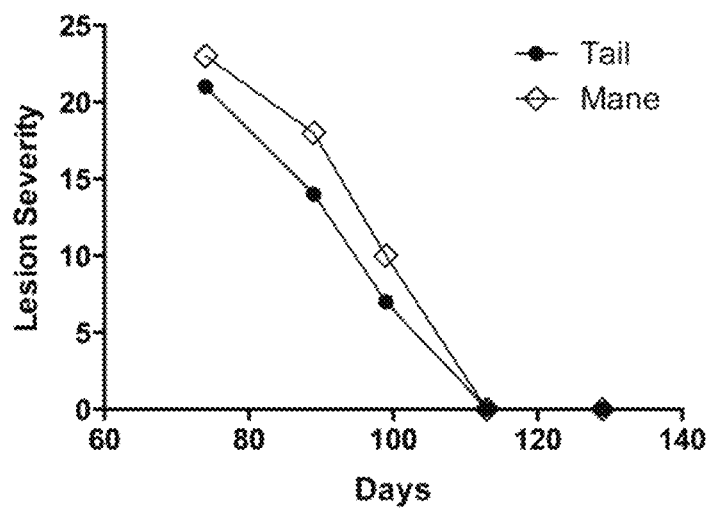
Figure 18D:
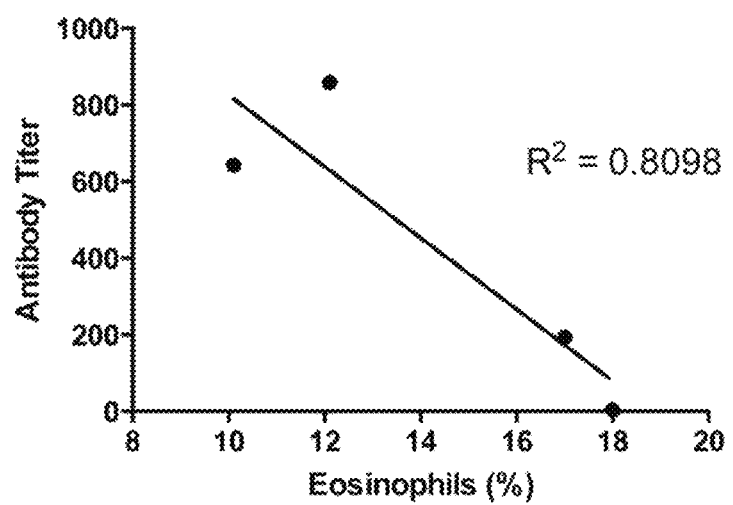
Figure 18E:
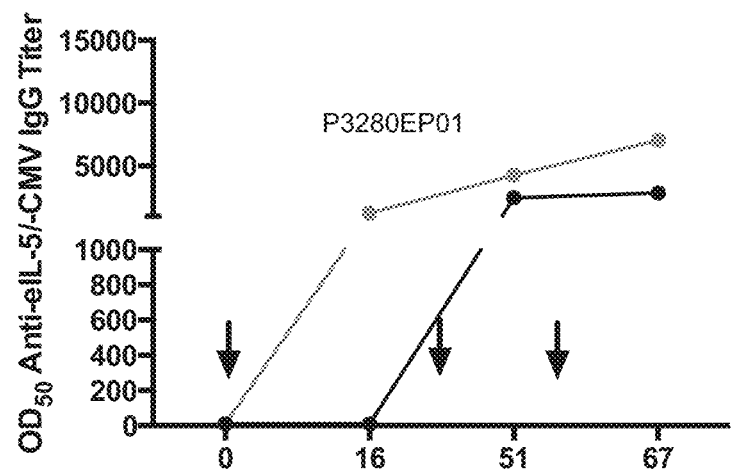
Figure 18F:
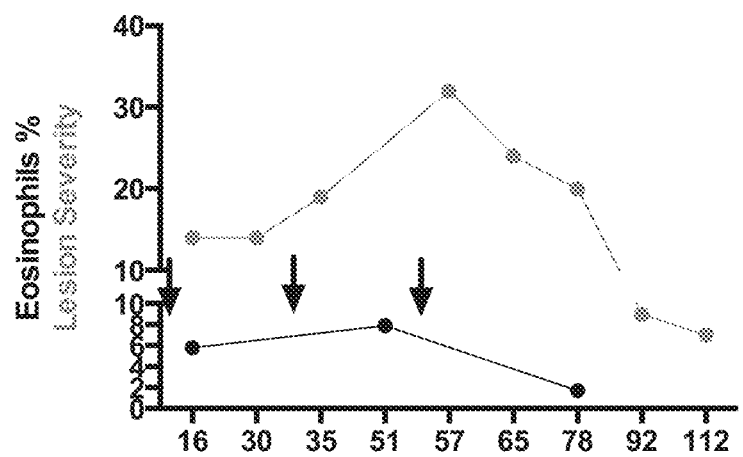
Figure 18G:
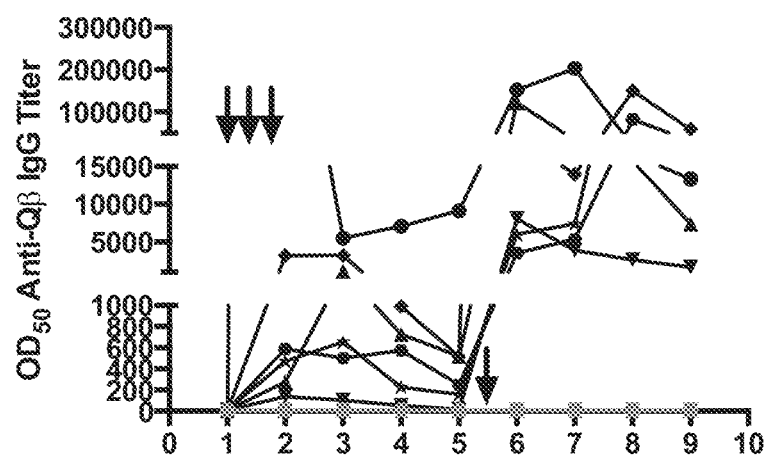

FIG. 18G: Efficient reduction of IBH disease parameters by eIL-5-C-His-Qβ in double-blind placebo controlled randomized study. Time course of antibody titer. Blood samples have been collected at several time points post injections (vaccine injections are indicated by arrows) and sera were analyzed for anti-Qβ IgG antibodies. Data timepoint 1 is 01.01.2015, timepoint 2 is 20.03.2015, timepoint 3 is 03.04.2015, timepoint 4 is 30.04.2015, timepoint 5 is 28.05.2015, timepoint 6 is 25.06.2015, timepoint 7 is 30.07.2015, timepoint 8 is 27.08.2015, timepoint 9 is 30.09.2015 of sera from vaccinated horses (black line) and placebo horses (grey line).

Figure 18H:
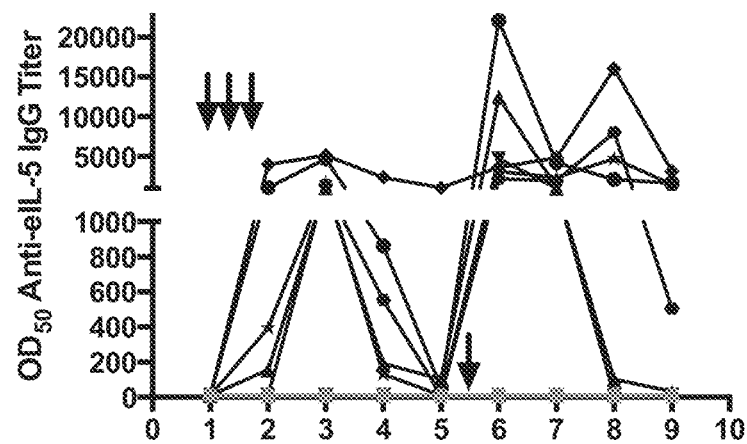

FIG. 18H: Efficient reduction of IBH disease parameters by eIL-5-C-His-Qβ in double-blind placebo controlled randomized study. Time course of antibody titer. Blood samples have been collected at several time points post injections (vaccine injections are indicated by arrows) and sera were analyzed for anti-eIL-5 IgG self-antibodies. Data timepoint 1 is 01.01.2015, timepoint 2 is 20.03.2015, timepoint 3 is 03.04.2015, timepoint 4 is 30.04.2015, timepoint 5 is 28.05.2015, timepoint 6 is 25.06.2015, timepoint 7 is 30.07.2015, timepoint 8 is 27.08.2015, timepoint 9 is 30.09.2015 of sera from vaccinated horses (black line) and placebo horses (grey line).

Figure 18I:
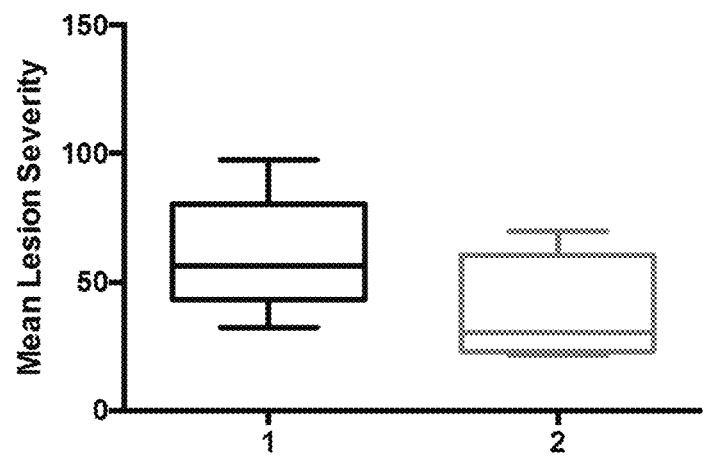

FIG. 18I: Efficient reduction of IBH disease parameters by eIL-5-C-His-Qβ in double-blind placebo controlled randomized study. Mean lesion severity of active horses (1, black bar) versus placebo horses (2, grey bar) in season before treatment (season 2014).

Figure 18J:
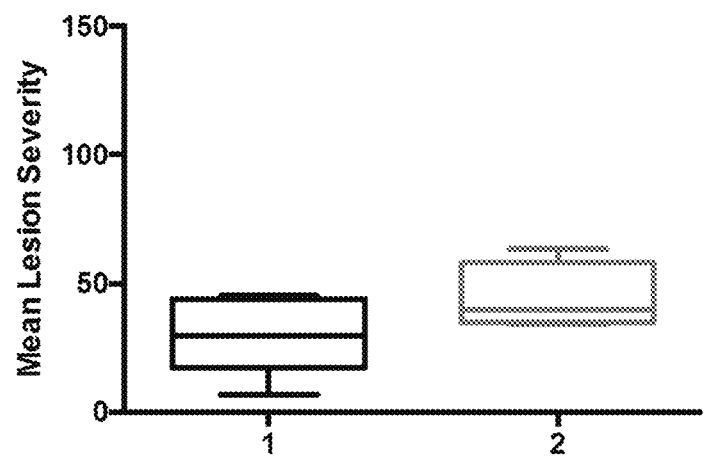

FIG. 18J: Efficient reduction of IBH disease parameters by eIL-5-C-His-Qβ in double-blind placebo controlled randomized study. Mean lesion severity of active horses (1, black bar) versus placebo horses (2, grey bar) in season with treatment (season 2015).

Figure 18K:
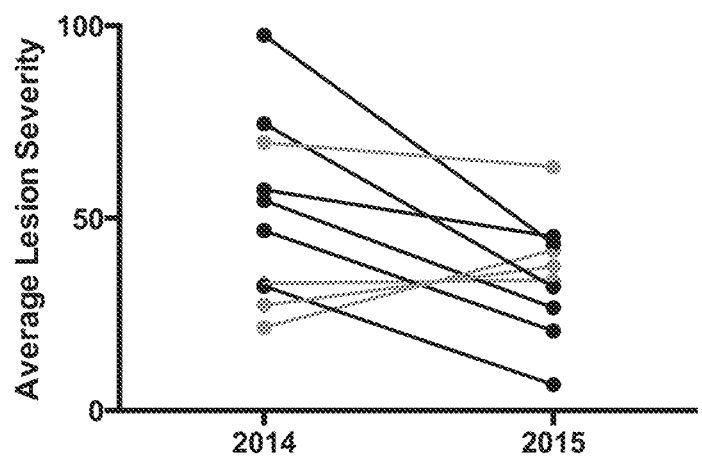

FIG. 18K: Efficient reduction of IBH disease parameters by eIL-5-C-His-Qβ in double-blind placebo controlled randomized study. Lesion severity of individual horses receiving eIL-5-C-His-Qβ vaccination (black lines) and placebo vaccination (grey lines) are shown for the season before treatment (2014) and the season with treatment (2015).

Figure 18L:
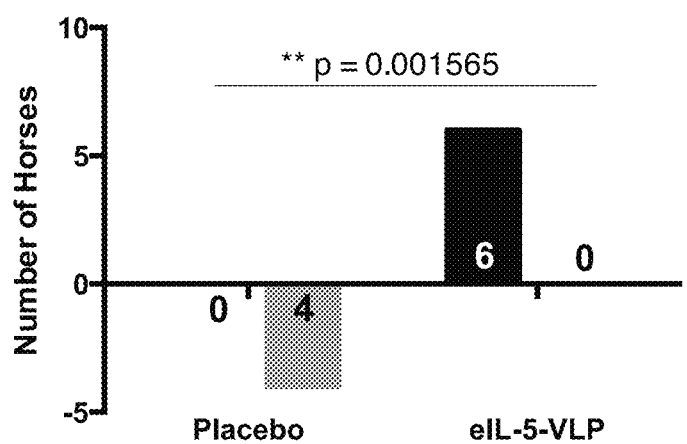

FIG. 18L: Efficient reduction of IBH disease parameters by eIL-5-C-His-Qβ in double-blind placebo controlled randomized study. Therapeutic effect of eIL-5-Qβ vaccination showing number of horses that improved in treatment season (first, black bar) or stayed stable or became worse (second, grey bar).

Figure 18M:
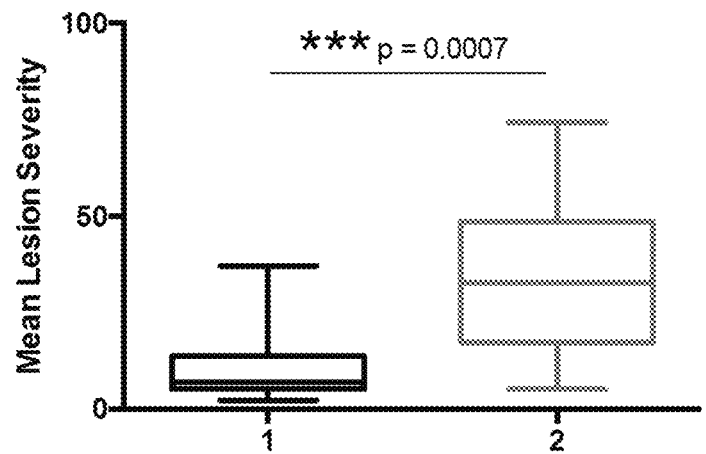

FIG. 18M: Efficient reduction of IBH disease parameters by eIL-5-C-His-Qβ in follow-up season. Mean lesion severity of ten active horses in follow-up season (1, black bar) versus fifteen placebo horses (2, grey bar) in the same season. Statistical analysis by non-parametric Mann-Whitney test.

Figure 18N:
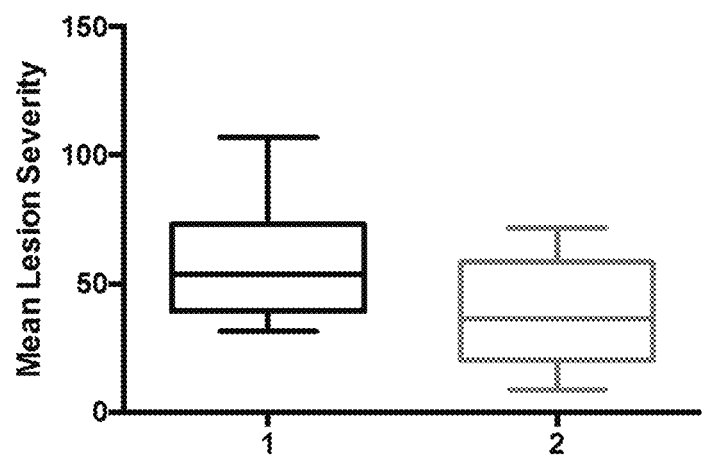

FIG. 18N: Efficient reduction of IBH disease parameters by eIL-5-C-His-CMVtt830 in double-blind placebo controlled randomized study. Mean lesion severity of active horses (1, black bar) and placebo horses (2, grey bar) in season before treatment (season 2015, April until June).

Figure 18O:
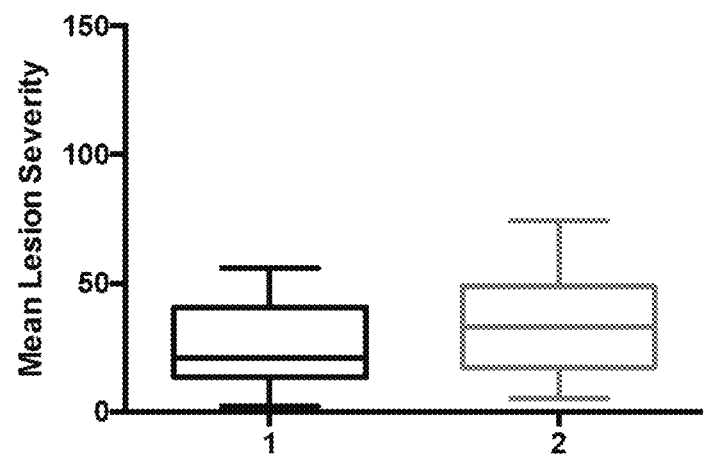

FIG. 18O: Efficient reduction of IBH disease parameters by eIL-5-C-His-CMVtt830 in double-blind placebo controlled randomized study. Mean lesion severity of active horses (1, black bar) and placebo horses (2, grey bar) in season with treatment (season 2016, April until June).

Figure 18P:
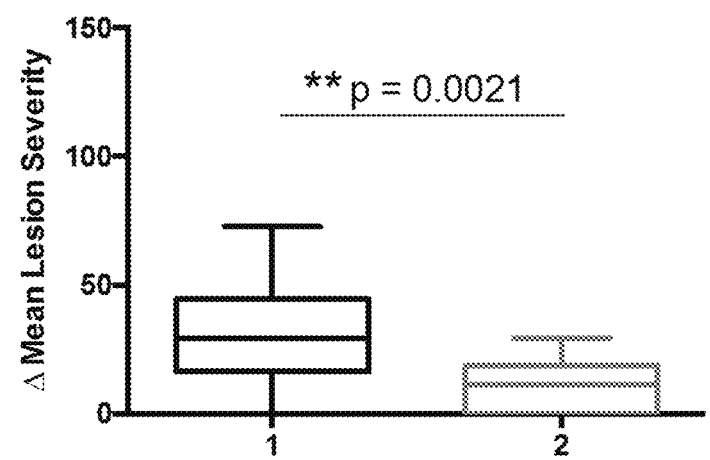

FIG. 18P: Efficient reduction of IBH disease parameters by eIL-5-C-His-CMVtt830 in double-blind placebo controlled randomized study. Delta of mean lesion severity measured from April until June of active horses (1, black bar) and placebo horses (2, grey bar) from year 2016 minus 2015. Statistical analysis by non-parametric Mann-Whitney test.

Figure 19A:
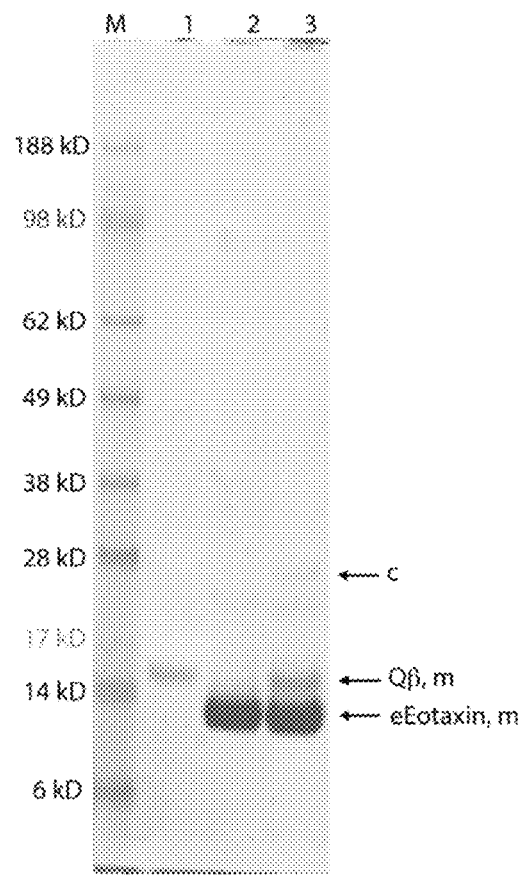

FIG. 19A: Analysis of coupling reaction of eEotaxin-C-His-Qβ. By SDS-PAGE. Proteins were stained with Coomassie blue: eEotaxin monomer (eEotaxin, m), Qβ monomer (Qβ, m) coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eEotaxin-C-His, lane 3, eEotaxin-C-His-Qβ coupling reaction.

Figure 19B:
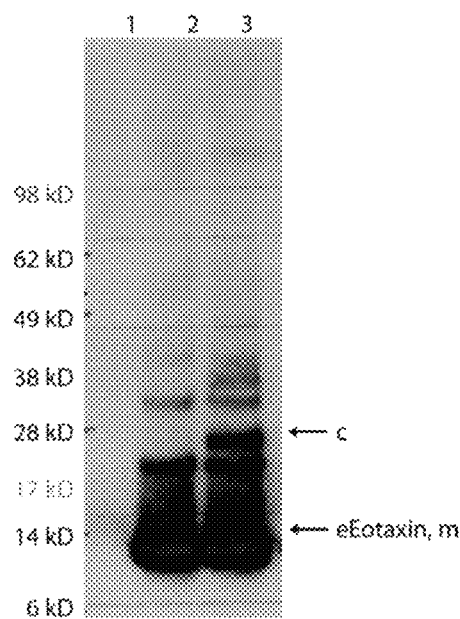

FIG. 19B: Analysis of coupling reaction of eEotaxin-C-His-Qβ. By Western-blot. Stained with α-His antibody: eEotaxin monomer (eEotaxin m), coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eEotaxin-C-His, lane 3, eEotaxin-C-His-Qβ coupling reaction.

Figure 20A:
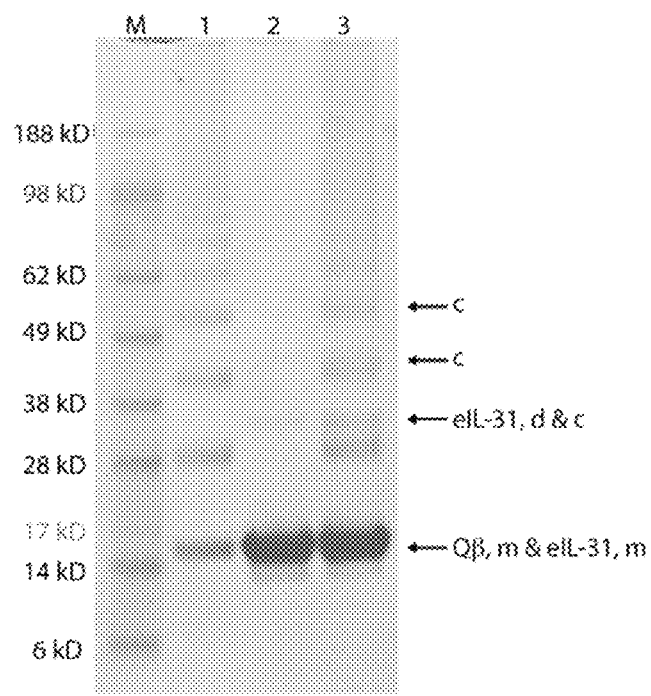

FIG. 20A: Analysis of coupling reaction of eIL-31-C-His-Qβ. By SDS-PAGE. Proteins were stained with Coomassie blue: eIL-31 monomer (eIL-31, m), eIL-31 dimer (eIL-31, d), Qβ monomer (Qβ, m) coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-31-C-His, lane 3, eIL-31-C-His-Qβ coupling reaction.

Figure 20B:
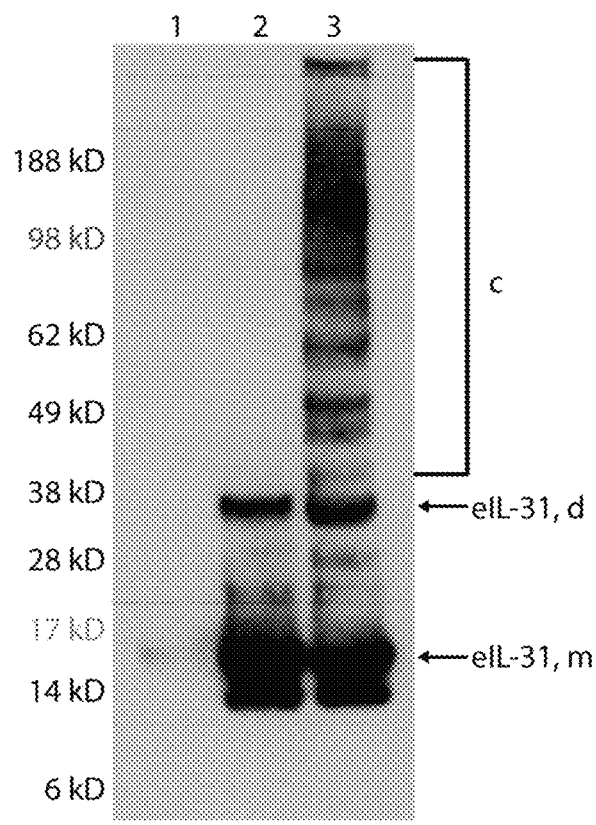

FIG. 20B: Analysis of coupling reaction of eIL-31-C-His-Qβ. By Western-blot. Stained with α-His antibody: eIL-31 monomer (eIL-31, m), eIL-31 dimer (eIL-31, d), coupling (c). Lane M, Size Marker (See Blue, prestained, NuPAGE, Novex, Invitrogen Life Technologies), lane 1, Qβ-VLP after derivatization with the chemical crosslinker SMPH, lane 2, TCEP activated eIL-31-C-His, lane 3, eIL-31-C-His-Qβ coupling reaction.

Figure 20C:
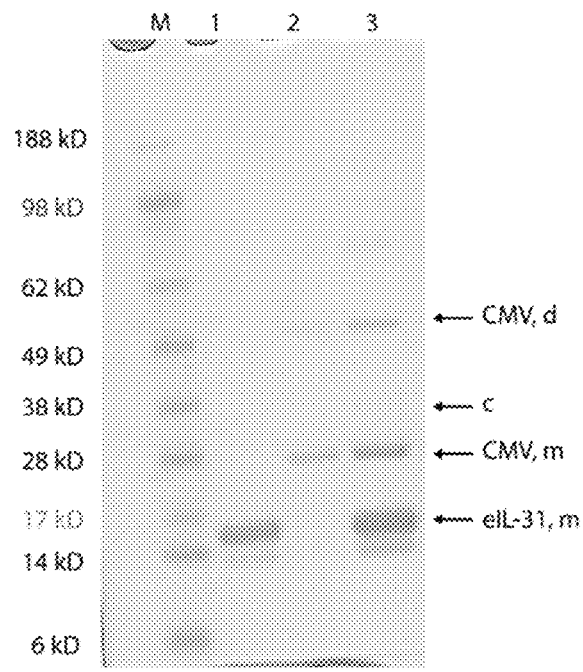

FIG. 20C: Analysis of coupling reaction of eIL-31-C-His-CMVtt830. By SDS-PAGE. Proteins were stained with Coomassie blue: eIL-31 monomer (eIL-31, m), CMVtt830 monomer (CMV, m), CMVtt830 dimer (CMV, d), coupling (c). Lane M, Size Marker (See Blue, prestained, NuPAGE, Novex, Invitrogen Life Technologies), lane 1, TCEP activated eIL-31-C-His, lane 2, CMVtt830-VLP after derivatization with the chemical crosslinker SMPH, lane 3, eIL-31-C-His-CMVtt830 coupling reaction.

Figure 20D:
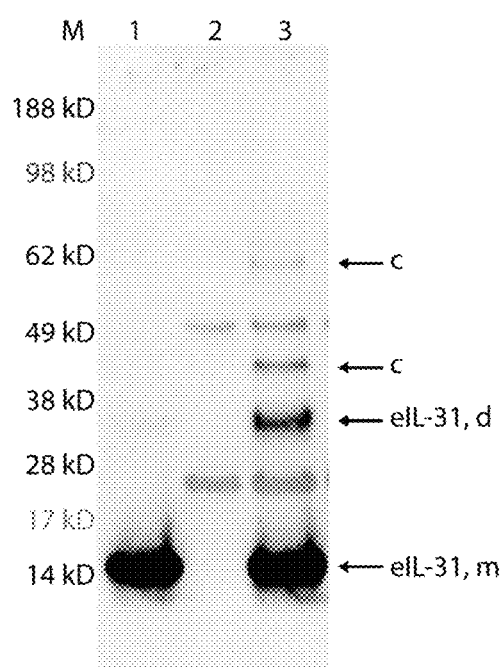

FIG. 20D: Analysis of coupling reaction of eIL-31-C-His-CMVtt830. By Western-blot. Stained with α-His antibody: eIL-31 monomer (eIL-31, m), eIL-31 dimer (eIL-31, d), coupling (c). Lane M, Size Marker (See Blue, prestained, NuPAGE, Novex, Invitrogen Life Technologies), lane 1, TCEP activated eIL-31-C-His, lane 2, CMVtt830-VLP after derivatization with the chemical crosslinker SMPH, lane 3, eIL-31-C-His-CMVtt830 coupling reaction.

DETAILED DESCRIPTION OF THE INVENTION

Unless defined otherwise, all technical and scientific terms used herein have the same meanings as commonly understood by one of ordinary skill in the art to which this invention belongs.

Virus-like particle (VLP): The term "virus-like particle (VLP)" as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. A virus-like particle in accordance with the invention is non-replicative and non-infectious since it lacks all or part of the viral genome or genome function. A virus-like particle in accordance with the invention may contain nucleic acid distinct from their genome. Recombinantly produced virus-like particles typically contain host cell derived RNA. A typical and preferred embodiment of a virus-like particle in accordance with the present invention is a viral capsid composed of polypeptides of the invention. A virus-like particle is typically a macromolecular assembly composed of viral coat protein which typically comprises 60, 120, 180, 240, 300, 360, or more than 360 protein subunits per virus-like particle. Typically and preferably, the interactions of these subunits lead to the formation of viral capsid or viral-capsid like structure with an inherent repetitive organization. One feature of a virus-like particle is its highly ordered and repetitive arrangement of its subunits.

Virus-like particle of an RNA bacteriophage: As used herein, the term "virus-like particle of an RNA bacteriophage" refers to a virus-like particle comprising, or preferably consisting essentially of or consisting of coat proteins, mutants or fragments thereof, of an RNA bacteriophage. In addition, virus-like particle of an RNA bacteriophage resembling the structure of an RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. Also included are virus-like particles of RNA bacteriophages, in which the aforementioned gene or genes are still present but inactive, and, therefore, also leading to non-replicative and/or non-infectious virus-like particles of an RNA bacteriophage. Preferred VLPs derived from RNA bacteriophages exhibit icosahedral symmetry and consist of 180 subunits (monomers). Preferred methods to render a virus-like particle of an RNA bacteriophage non replicative and/or non-infectious is by physical, chemical inactivation, such as UV irradiation, formaldehyde treatment, typically and preferably by genetic manipulation.

Virus-like particle of CMV: The terms "virus-like particle of CMV" or CMV VLPs refer to a virus-like particle comprising, or preferably consisting essentially of, or preferably consisting of at least one CMV polypeptide. Preferably, a virus-like particle of CMV comprises said CMV polypeptide as the major, and even more preferably as the sole protein component of the capsid structure. Typically and preferably, virus-like particles of CMV resemble the structure of the capsid of CMV. Virus-like particles of CMV are non-replicative and/or non-infectious, and lack at least the gene or genes encoding for the replication machinery of the CMV, and typically also lack the gene or genes encoding the protein or proteins responsible for viral attachment to or entry into the host. This definition includes also virus-like particles in which the aforementioned gene or genes are still present but inactive. Preferred methods to render a virus-like particle of CMV non replicative and/or non-infectious is by physical or chemical inactivation, such as UV irradiation, formaldehyde treatment. Preferably, VLPs of CMV lack the gene or genes encoding for the replication machinery of the CMV, and also lack the gene or genes encoding the protein or proteins responsible for viral attachment to or entry into the host. Again more preferably, non-replicative and/or non-infectious virus-like particles are obtained by recombinant gene technology. Recombinantly produced virus-like particles of CMV according to the invention typically and preferably do not comprise the viral genome. Virus-like particles comprising more than one species of polypeptides, often referred to as mosaic VLPs are also encompassed by the invention. Thus, in one embodiment, the virus-like particle according to the invention comprises at least two different species of polypeptides, wherein at least one of said species of polypeptides is a CMV polypeptide. Preferably, a VLP of CMV is a macromolecular assembly composed of CMV coat protein which typically comprises 180 coat protein subunits per VLP. Typically and preferably, a VLP of CMV as used herein, comprises, essentially consists of, or alternatively consists of, at least one CMV polypeptide comprising or preferably consisting of (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said amino acid sequence to be mutated show a sequence identity of at least 90%, preferably of at least 95%, further preferably of at least 98% and again more preferably of at least 99%.

Antigen: As used herein, the term "antigen" refers to a molecule capable of being bound by an antibody or a T-cell receptor (TCR) if presented by MHC molecules. The term "antigen", as used herein, also refers to T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and/or is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. If not indicated otherwise, the term "antigen" as used herein does not refer to the core particle or virus-like particle contained in the inventive compositions, immunogenic or vaccine compositions and/or pharmaceutical compositions.

Coat protein: The term "coat protein" refers to a viral protein, preferably to a subunit of a natural capsid of a virus, preferably of an RNA bacteriophage or a plant virus, which is capable of being incorporated into a virus capsid or a VLP. The term coat protein encompasses naturally occurring coat protein as well as recombinantly expressed coat protein. Further encompassed are mutants and fragments of coat protein, wherein said mutants and fragments retains the capability of forming a VLP.

Polypeptide: The term "polypeptide" as used herein refers to a polymer composed of amino acid monomers which are linearly linked by peptide bonds (also known as amide bonds). The term polypeptide refers to a consecutive chain of amino acids and does not refer to a specific length of the product. Thus, peptides, and proteins are included within the definition of polypeptide.

Cucumber Mosaic Virus (CMV) polypeptide: The term "cucumber mosaic virus (CMV) polypeptide" as used herein refers to a polypeptide comprising or preferably consisting of: (i) an amino acid sequence of a coat protein of cucumber mosaic virus (CMV), or (ii) a mutated amino acid sequence, wherein the amino acid sequence to be mutated is an amino acid sequence of a coat protein of CMV, and wherein said mutated amino acid sequence and said amino acid sequence to be mutated, i.e. said coat protein of CMV, show a sequence identity of at least 90%, preferably of at least 95%, further preferably of at least 98% and again more preferably of at least 99%. Typically and preferably, the CMV polypeptide is capable of forming a virus-like particle of CMV upon expression by self-assembly.

Coat protein (CP) of cucumber mosaic virus (CMV): The term "coat protein (CP) of cucumber mosaic virus (CMV)", as used herein, refers to a coat protein of the cucumber mosaic virus which occurs in nature. Due to extremely wide host range of the cucumber mosaic virus, a lot of different strains and isolates of CMV are known and the sequences of the coat proteins of said strains and isolates have been determined and are, thus, known to the skilled person in the art as well. The sequences of said coat proteins (CPs) of CMV are described in and retrievable from the known databases such as Genbank, dpvweb.net, or ncbi.nlm.nih.gov/protein/. Examples are described in EP Application No. 14189897.3. Further examples of CMV coat proteins are provided in SEQ ID NOs 15-17. It is noteworthy that these strains and isolates have highly similar coat protein sequences at different protein domains, including the N-terminus of the coat protein. In particular, 98.1% of all completely sequenced CMV isolates share more than 85% sequence identity within the first 28 amino acids of their coat protein sequence, and still 79.5% of all completely sequenced CMV isolates share more than 90% sequence identity within the first 28 amino acids of their coat protein sequence. Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in *E. coli*.

Typically and preferably, the coat protein of CMV used for the present invention is capable of forming a virus-like particle of CMV upon expression by self-assembly. Preferably, the coat protein of CMV used for the present invention is capable of forming a virus-like particle of CMV upon expression by self-assembly in *E. coli*.

Modified virus-like particle (VLP) of cucumber mosaic virus (CMV): The term "modified virus-like particle (VLP) of cucumber mosaic virus (CMV)" as used herein, refers to a VLP of CMV which is a modified one in such as it comprises, or preferably consists essentially of, or preferably consists of at least one modified CMV polypeptide, wherein said modified CMV polypeptide comprises, or preferably consists of, a CMV polypeptide, and a T helper cell epitope. Typically and preferably, said T helper cell epitope (i) is fused to the N-terminus of said CMV polypeptide, (ii) is fused to the C-terminus of said CMV polypeptide, (iii) replaces a region of consecutive amino acids of said CMV polypeptide, wherein the sequence identity between said replaced region of consecutive amino acids of said CMV polypeptide and the T helper cell epitope is at least 15%, preferably at least 20%, or (iv) replaces a N-terminal region of said CMV polypeptide, and wherein said replaced N-terminal region of said CMV polypeptide consists of 5 to 15 consecutive amino acids. Preferably, said T helper cell epitope replaces a N-terminal region of said CMV polypeptide, and wherein said replaced N-terminal region of said CMV polypeptide consists of 5 to 15 consecutive amino acids, preferably of 9 to 14 consecutive amino acids, more preferably of 11 to 13 consecutive amino acids, and most preferably of 11, 12 or 13 consecutive amino acids. Preferably said modified VLP of CMV of the present invention is a recombinant modified VLP of CMV.

Modified CMV polypeptide: The term "modified CMV polypeptide" as used herein refers to a CMV polypeptide modified in such as defined herein, that said modified CMV polypeptide comprises, or preferably consists of, a CMV polypeptide, and a T helper cell epitope. Typically, the modified CMV polypeptide is capable of forming a virus-like particle of CMV upon expression by self-assembly. Preferably, the modified CMV polypeptide is a recombinant modified CMV polypeptide and is capable of forming a virus-like particle of CMV upon expression by self-assembly in *E. coli*.

N-terminal region of the CMV polypeptide: The term "N-terminal region of the CMV polypeptide" as used herein, refers either to the N-terminus of said CMV polypeptide, and in particular to the N-terminus of a coat protein of CMV, or to the region of the N-terminus of said CMV polypeptide or said coat protein of CMV but starting with the second amino acid of the N-terminus of said CMV polypeptide or said coat protein of CMV if said CMV polypeptide or said coat protein comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes. The term "N-terminal region of the mutated amino acid sequence of a CMV polypeptide or a CMV coat protein" as used herein, refers either to the N-terminus of said mutated amino acid sequence of said CMV polypeptide or said coat protein of CMV, or to the region of the N-terminus of said mutated amino acid sequence of said CMV polypeptide or said coat protein of CMV but starting with the second amino acid of the N-terminus of said mutated amino acid sequence of said CMV polypeptide or said coat protein of CMV if said mutated amino acid sequence comprises a N-terminal methionine residue. Preferably, in case said CMV polypeptide or said coat protein comprises a N-terminal methionine residue, from a practical point of view, the start-codon encoding methionine will usually be deleted and added to the N-terminus of the Th cell epitope. Further preferably, one, two or three additional amino acids, preferably one amino acid, may be optionally inserted between the stating methionine and the Th cell epitope for cloning purposes.

Recombinant polypeptide: In the context of the invention the term "recombinant polypeptide" refers to a polypeptide which is obtained by a process which comprises at least one step of recombinant DNA technology. Typically and preferably, a recombinant polypeptide is produced in a prokaryotic expression system. It is apparent for the artisan that recombinantly produced polypeptides which are expressed in a prokaryotic expression system such as *E. coli* may comprise an N-terminal methionine residue. The N-terminal methionine residue is typically cleaved off the recombinant polypeptide in the expression host during the maturation of the recombinant polypeptide. However, the cleavage of the N-terminal methionine may be incomplete. Thus, a preparation of a recombinant polypeptide may comprise a mixture of otherwise identical polypeptides with and without an N-terminal methionine residue. Typically and preferably, a preparation of a recombinant polypeptide comprises less than 10%, more preferably less than 5%, and still more preferably less than 1% recombinant polypeptide with an N-terminal methionine residue.

Recombinant CMV polypeptide: The term "recombinant CMV polypeptide" refers to a CMV polypeptide as defined above which is obtained by a process which comprises at least one step of recombinant DNA technology. Typically and preferably a preparation of a recombinant CMV polypeptide comprises less than 10%, more preferably less than 5%, and still more preferably less than 1% recombinant CMV polypeptide with an N-terminal methionine residue. Consequently, a recombinant virus-like particle of the invention may comprise otherwise identical recombinant polypeptides with and without an N-terminal methionine residue.

Recombinant modified CMV polypeptide: The term "recombinant modified CMV polypeptide" refers to a modified CMV polypeptide as defined above which is obtained by a process which comprises at least one step of recombinant DNA technology. Typically and preferably a preparation of a recombinant modified CMV polypeptide comprises less than 10%, more preferably less than 5%, and still more preferably less than 1% recombinant modified CMV polypeptide with an N-terminal methionine residue. Consequently, a recombinant virus-like particle of the invention may comprise otherwise identical recombinant polypeptides with and without an N-terminal methionine residue.

Recombinant virus-like particle: In the context of the invention the term "recombinant virus-like particle" refers to a virus-like particle (VLP) which is obtained by a process which comprises at least one step of recombinant DNA technology. Typically and preferably a recombinant VLP is obtained by expression of a recombinant viral coat protein in host, preferably in a bacterial cell. Typically and preferably, a recombinant virus-like particle comprises at least one recombinant polypeptide, preferably a recombinant CMV polypeptide or recombinant modified CMV polypeptide. Most preferably, a recombinant virus-like particle is composed of or consists of recombinant CMV polypeptides or recombinant modified CMV polypeptides. As a consequence, if in the context of the present invention the definition of inventive recombinant VLPs are effected with reference to specific amino acid sequences comprising a N-terminal methionine residue the scope of these inventive recombinant VLPs encompass the VLPs formed by said specific amino acid sequences without said N-terminal methionine residue but as well, even though typically in a minor amount as indicated herein, the VLPs formed by said specific amino acid sequences with said N-terminal methionine. Furthermore, it is within the scope of the present invention that if the definition of inventive recombinant VLPs are effected with reference to specific amino acid sequences comprising a N-terminal methionine residue VLPs are encompassed comprising both amino acid sequences comprising still said N-terminal methionine residue and amino acid sequences lacking the N-terminal methionine residue.

Mutated amino acid sequence: The term "mutated amino acid sequence" refers to an amino acid sequence which is obtained by introducing a defined set of mutations into an amino acid sequence to be mutated. In the context of the invention, said amino acid sequence to be mutated typically and preferably is an amino acid sequence of a coat protein of CMV. Thus, a mutated amino acid sequence differs from an amino acid sequence of a coat protein of CMV in at least one amino acid residue, wherein said mutated amino acid sequence and said amino acid sequence to be mutated show a sequence identity of at least 90%. Typically and preferably said mutated amino acid sequence and said amino acid sequence to be mutated show a sequence identity of at least 91%, 92%, 93% 94%, 95%, 96%, 97%, 98%, or 99%. Preferably, said mutated amino acid sequence and said sequence to be mutated differ in at most 11, 10, 9, 8, 7, 6, 4, 3, 2, or 1 amino acid residues, wherein further preferably said difference is selected from insertion, deletion and amino acid exchange. Preferably, the mutated amino acid sequence differs from an amino acid sequence of a coat protein of CMV in least one amino acid, wherein preferably said difference is an amino acid exchange.

Position corresponding to residues . . . : The position on an amino acid sequence, which is corresponding to given residues of another amino acid sequence can be identified by sequence alignment, typically and preferably by using the BLASTP algorithm, most preferably using the standard settings. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Sequence identity: The sequence identity of two given amino acid sequences is determined based on an alignment of both sequences. Algorithms for the determination of sequence identity are available to the artisan. Preferably, the sequence identity of two amino acid sequences is determined using publicly available computer homology programs such as the "BLAST" program (blast.ncbi.nlm.nih.gov/Blast.cgi) or the "CLUSTAL, (genome.jp/tools/clustalw/) and hereby preferably by the "BLAST" program provided on the NCBI homepage at blast.ncbi.nlm.nih.gov/Blast.cgi, using the default settings provided therein. Typical and preferred standard settings are: expect threshold: 10; word size: 3; max matches in a query range: 0; matrix: BLOSUM62; gap costs: existence 11, extension 1; compositional adjustments: conditional compositional score matrix adjustment.

Epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-20 amino acids in a spatial conformation which is unique to the antigenic site.

T helper (Th) cell epitope: The term "T helper (Th) cell epitope" as used herein refers to an epitope that is capable of recognition by a helper Th cell. In another preferred embodiment, said T helper cell epitope is a universal T helper cell epitope.

Universal Th cell epitope: The term "universal Th cell epitope" as used herein refers to a Th cell epitope that is capable of binding to at least one, preferably more than one MHC class II molecules. The simplest way to determine whether a peptide sequence is a universal Th cell epitope is to measure the ability of the peptide to bind to individual MHC class II molecules. This may be measured by the ability of the peptide to compete with the binding of a known Th cell epitope peptide to the MHC class II molecule. A representative selection of HLA-DR molecules are described in e.g. Alexander J, et al., Immunity (1994) 1:751-761. Affinities of Th cell epitopes for MHC class II molecules should be at least 10'M. An alternative, more tedious but also more relevant way to determine the "universality" of a Th cell epitope is the demonstration that a larger fraction of people (>30%) generate a measurable T cell response upon immunization and boosting one months later with a protein containing the Th cell epitope formulated in IFA. A representative collection of MHC class II molecules present in different individuals is given in Panina-Bordignon P, et al., Eur J Immunol (1989) 19:2237-2242. As a consequence, the term "universal Th cell epitope" as used herein preferably refers to a Th cell epitope that generates a measurable T cell response upon immunization and boosting (one months later with a protein containing the Th cell epitope formulated in IFA) in more than 30% of a selected group of individuals as described in Panina-Bordignon P, et al., Eur J Immunol (1989) 19:2237-2242. Moreover, and again further preferred, the term "universal Th cell epitope" as used herein preferably refers to a Th cell epitope that is capable of binding to at least one, preferably to at least two, and even more preferably to at least three DR alleles selected from of DR1, DR2w2b, DR3, DR4w4, DR4w14, DR5, DR7, DR52a, DRw53, DR2w2a; and preferably selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40. In an even again more preferable manner, the term "universal Th cell epitope" as used herein refers to a Th cell epitope that is capable of binding to at least one, preferably to at least two, and even more preferably to at least three DR alleles selected from DR1, DR2w2b, DR4w4, DR4w14, DR5, DR7, DRw53, DR2w2a, with an affinity at least 500 nM (as described in Alexander J, et al., Immunity (1994) 1:751-761 and references cited herein); a preferred binding assay to evaluate said affinities is the one described by Sette A, et al., J Immunol (1989) 142:35-40.

Universal Th cell epitopes are described, and known to the skilled person in the art, such as by Alexander J, et al., Immunity (1994) 1:751-761, Panina-Bordignon P, et al., Eur J Immunol (1989) 19:2237-2242, Calvo-Calle J M, et al., J Immunol (1997) 159:1362-1373, and Valmori D, et al., J Immunol (1992) 149:717-721.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminum hydroxide, and modified muramyldipeptide. Further preferred adjuvants are mineral gels such as aluminum hydroxide, surface active substances such as lyso lecithin, pluronic polyols, polyanions, peptides, oil emulsions, keyhole limpet hemocyanins, dinitrophenol, and human adjuvants such as BCG (bacille Calmette Guerin) and Corynebacterium parvum. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants may also comprise mixtures of these substances. Virus-like particles have been generally described as an adjuvant. However, the term "adjuvant", as used within the context of this application, refers to an adjuvant not being the inventive virus-like particle. Rather "adjuvant" relates to an additional, distinct component of the inventive compositions, vaccines or pharmaceutical compositions.

Effective amount: As used herein, the term "effective amount" refers to an amount necessary or sufficient to realize a desired biologic effect. An effective amount of the composition, or alternatively the pharmaceutical composition, would be the amount that achieves this selected result, and such an amount could be determined as a matter of routine by a person skilled in the art. Preferably, the term "effective amount", as used herein, refers to an amount necessary or sufficient to be effective to reduce at least one IBH parameter or symptom, wherein preferably said at least one IBH parameter or symptom is the level or severity grade of skin lesions, and wherein further preferably said reduction of said level or severity grade of skin lesions is determined by a symptom lesion scoring test. The effective amount can vary depending on the particular composition being administered and the size of the subject. One of ordinary skill in the art can empirically determine the effective amount of a particular composition of the present invention without necessitating undue experimentation.

Treatment: As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment.

Attachment Site, First: As used herein, the phrase "first attachment site" refers to an element which is naturally occurring with the virus-like particle or which is artificially added to the virus-like particle, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid residue, preferably of a lysine residue. The first attachment site is typically located on the surface, and preferably on the outer surface of the VLP. Multiple first attachment sites are present on the surface, preferably on the outer surface of the VLP, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP. In a very preferred embodiment said first attachment site is the amino group of a lysine residue of the amino acid sequence of said VLP polypeptide.

Attachment Site, Second: As used herein, the phrase "second attachment site" refers to an element which is naturally occurring with or which is artificially added to the antigen and to which the first attachment site may be linked. The second attachment site of the antigen preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is a sulfhydryl group, preferably the sulfhydryl group of the amino acid cysteine most preferably the sulfhydryl group of a cysteine residue. The term "antigen with at least one second attachment site" refers, therefore, to a construct comprising the antigen and at least one second attachment site. However, in particular for a second attachment site, which is not naturally occurring within the antigen, such a construct typically and preferably further comprises a "linker". In another preferred embodiment the second attachment site is associated with the antigen through at least one covalent bond, preferably through at least one peptide bond. In a further embodiment, the second attachment site is naturally occurring within the antigen. In another further preferred embodiment, the second attachment site is artificially added to the antigen through a linker, wherein said linker comprises or alternatively consists of a cysteine. Preferably, the linker is fused to the antigen by a peptide bond.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s).

Linker: A "linker", as used herein, either associates the second attachment site with the antigen or already comprises, essentially consists of, or consists of the second attachment site. Preferably, a "linker", as used herein, already comprises the second attachment site, typically and preferably—but not necessarily—as one amino acid residue, preferably as a cysteine residue. A preferred linkers are an amino acid linkers, i.e. linkers containing at least one amino acid residue. The term amino acid linker does not imply that such a linker consists exclusively of amino acid residues. However, a linker consisting exclusively of amino acid residues is a preferred embodiment of the invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Association of the linker with the antigen is preferably by way of at least one covalent bond, more preferably by way of at least one peptide bond.

Equine mammal: An "equine mammal", as used herein, is a mammal included in the family Equidae including horses, ponies, asses (donkeys), and zebras. Preferably, the term "equine mammal", as used herein, refers to a horse, a pony, an ass (a donkey), and a zebra. Again more preferably, the term "equine mammal", as used herein, refers to a horse.

Thus, in a first aspect, the present invention provides for a composition comprising: (a) a core particle with at least one first attachment site; and (b) at least one antigen with at least one second attachment site, wherein said at least one antigen is (i) an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; or (ii) an equine Eotaxin antigen (eEotaxin antigen), wherein said eEotaxin antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6; (iii) an equine Interleukin-31 antigen (eIL-31 antigen), wherein said eIL-31 antigen comprises, or preferably is, a protein with the amino sequence selected from SEQ ID NO:12 or a protein with an amino acid sequence of at least 90%, preferably of at least 92%, further preferably of at least 95%, and again further preferably of at least 98% amino acid sequence identity with SEQ ID NO:12;

wherein (a) and (b) are linked through said at least one first and said at least one second attachment site via at least one non-peptide covalent bond.

In one embodiment, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 98% amino acid sequence identity with SEQ ID NO:1.

In a preferred embodiment, said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5, SEQ ID NO:35, SEQ ID NO:36, SEQ ID NO:37 and SEQ ID NO:38. In a further preferred embodiment, said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2 and SEQ ID NO:5. In a further preferred embodiment, said at least one antigen is an equine Interleukin-5 antigen (eIL-5 antigen), and wherein said eIL-5 antigen comprises, or preferably is, a protein with the amino sequence selected from SEQ ID NO:35, SEQ ID NO:36 and SEQ ID NO:38. In a further preferred embodiment, said at least one antigen is an equine Interleukin-5 antigen (eIL-5 antigen), and wherein said eIL-5 antigen comprises, or preferably is, a protein with the amino sequence of SEQ ID NO:1, In a further preferred embodiment, said at least one antigen is an equine Interleukin-5 antigen (eIL-5 antigen), and wherein said eIL-5 antigen comprises, or preferably is, a protein with the amino sequence of SEQ ID NO:2. In a further preferred embodiment, said at least one antigen is an equine Interleukin-5 antigen (eIL-5 antigen), and wherein said eIL-5 antigen comprises, or preferably is, a protein with the amino sequence of SEQ ID NO:5. In a further preferred embodiment, said at least one antigen is an equine Interleukin-5 antigen (eIL-5 antigen), and wherein said eIL-5 antigen comprises, or preferably is, a protein with the amino sequence of SEQ ID NO:35. In a very further preferred embodiment, said at least one antigen is an equine Interleukin-5 antigen (eIL-5 antigen), and wherein said eIL-5 antigen comprises, or preferably is, a protein with the amino sequence of SEQ ID NO:36. In a further preferred embodiment, said at least one antigen is an equine Interleukin-5 antigen (eIL-5 antigen), and wherein said eIL-5 antigen comprises, or preferably is, a protein with the amino sequence of SEQ ID NO:37. In a further very preferred embodiment, said at least one antigen is an equine Interleukin-5 antigen (eIL-5 antigen), and wherein said eIL-5 antigen comprises, or preferably is, a protein with the amino sequence of SEQ ID NO:38.

In one embodiment, said at least one antigen is an equine Eotaxin antigen (eEotaxin antigen), wherein said eEotaxin antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6.

In a preferred embodiment, said at least one antigen is an equine Eotaxin antigen (eEotaxin antigen), wherein said eEotaxin antigen comprises, or preferably is, a protein with the amino sequence selected from SEQ ID NO:6, SEQ ID NO:7, SEQ ID NO:10, SEQ ID NO:39, SEQ ID NO:40, SEQ ID NO:41 and SEQ ID NO:42. In a further preferred embodiment, said at least one antigen is an equine Eotaxin antigen (eEotaxin antigen), wherein said eEotaxin antigen comprises, or preferably is, a protein with the amino sequence selected from SEQ ID NO:6, SEQ ID NO:7 and SEQ ID NO:10.

In one embodiment, said at least one antigen is an equine Interleukin-31 antigen (eIL-31 antigen), wherein said eIL-31 antigen comprises, or preferably is, a protein with the amino sequence selected from SEQ ID NO:12 or a protein with an amino acid sequence of at least 90%, preferably of at least 92%, further preferably of at least 95%, and again further preferably of at least 98% amino acid sequence identity with SEQ ID NO:12.

In a preferred embodiment, said at least one antigen is an equine Interleukin-31 antigen (eIL-31 antigen), wherein said eIL-31 antigen comprises, or preferably is, a protein with the amino sequence selected from SEQ ID NO:12, SEQ ID NO:14, SEQ ID NO:43, SEQ ID NO:44, SEQ ID NO:45, SEQ ID NO:46. In a further preferred embodiment, said at least one antigen is an equine Interleukin-31 antigen (eIL-31 antigen), wherein said eIL-31 antigen comprises, or prefer- ably is, a protein with the amino sequence selected from SEQ ID NO:12 and SEQ ID NO:14.

In a further preferred embodiment, said core particle is a virus-like particle (VLP), preferably a recombinant VLP. In again a further preferred embodiment, said VLP is derived from a plant virus or a bacteriophage, and wherein preferably said bacteriophage is a RNA bacteriophage.

Thus, in a further preferred embodiment, said core particle is a virus-like particle (VLP), and wherein said VLP is derived from a RNA bacteriophage.

Further preferred is a recombinant VLP of an RNA bacteriophage as core particle of the present invention. In a further preferred embodiment, said VLP comprises, consists essentially of, or alternatively consists of, recombinant coat proteins of an RNA bacteriophage, and wherein preferably said VLP comprises, consists essentially of, or alternatively consists of, recombinant coat proteins of RNA bacteriophage Qβ or of RNA bacteriophage AP205, and wherein further preferably said VLP comprises, consists essentially of, or alternatively consists of, recombinant coat proteins of RNA bacteriophage Qβ.

In a further preferred embodiment, said VLP comprises, consists essentially of, or alternatively consists of, recombinant coat proteins comprising or preferably consisting of an amino acid sequence selected from (a) SEQ ID NO:31; (b) a mixture of SEQ ID NO:31 and SEQ ID NO:32; or (c) SEQ ID NO:33. In a very further preferred embodiment, said VLP is a VLP of RNA bacteriophage Qβ. In a further preferred embodiment, said VLP comprises, consists essentially of, or alternatively consists of, recombinant coat proteins of RNA bacteriophage Qβ. Again in a further preferred embodiment, said VLP comprises, consists essentially of, or alternatively consists of, recombinant coat proteins comprising or preferably consisting of SEQ ID NO:31.

In another preferred embodiment, said core particle is a virus-like particle (VLP) wherein said VLP is a VLP of RNA bacteriophage Qβ, and said VLP comprises, consists essentially of, or alternatively consists of, recombinant coat proteins of RNA bacteriophage Qβ, and wherein said recombinant coat proteins comprising or preferably consisting of SEQ ID NO:31.

In one embodiment, said VLP is not a VLP of an RNA bacteriophage, preferably said VLP is not a recombinant VLP of an RNA bacteriophage. In one embodiment, said virus-like particle is not a virus-like particle of an RNA-bacteriophage Qβ.

In a further preferred embodiment, said core particle is a virus-like particle (VLP), and wherein said VLP is derived from a plant virus. In another preferred embodiment, said VLP is a recombinant VLP, and wherein preferably said recombinant VLP is derived from a plant virus. In another preferred embodiment, said VLP is a VLP of cucumber mosaic virus (CMV).

In a preferred embodiment, said VLP is a modified VLP comprising, essentially consisting of, or alternatively consisting of, at least one modified VLP polypeptide, wherein said modified VLP polypeptide comprises, or preferably consists of, (a) a VLP polypeptide, and (b) a T helper cell epitope, wherein said VLP polypeptide comprises, or preferably consists of, (i) an amino acid sequence of a coat protein of a virus, preferably an amino acid sequence of a coat protein of a plant virus; or (ii) a mutated amino acid sequence, wherein the amino acid sequence to be mutated is an amino acid sequence of said coat protein of a virus, and wherein said mutated amino acid sequence and said coat protein of a virus show a sequence identity of at least 90%, preferably of at least 95%, further preferably of at least 98% and again more preferably of at least 99%.

In a preferred embodiment, said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of, (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%.

In a preferred embodiment, said CMV polypeptide comprises, preferably consists of, an amino acid sequence of a coat protein of CMV. In another preferred embodiment, said CMV polypeptide comprises, preferably consists of a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%. Typically and preferably, said mutated amino acid sequence and said amino acid sequence to be mutated differ in least one and in at most 11, 10, 9, 8, 7, 6, 5, 4, 3, or 2 amino acid residues, and wherein preferably these differences are selected from (i) insertion, (ii) deletion, (iii) amino acid exchange, and (iv) any combination of (i) to (iii).

In another preferred embodiment, said CMV polypeptide comprises, or preferably consists of, (i) (a) an amino acid sequence of a coat protein of CMV, wherein said amino acid sequence comprises, or preferably consists of, SEQ ID NO:15 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:15; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:15 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:15.

In another preferred embodiment, said CMV polypeptide comprises, or preferably consists of, (i) (a) an amino acid sequence of a coat protein of CMV, wherein said amino acid sequence comprises SEQ ID NO:34, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:34; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 95%, preferably of at least 98%, and more preferably of at least 99%.

In a further preferred embodiment, said CMV polypeptide comprises, or preferably consists of, (a) an amino acid sequence of a coat protein of CMV, wherein said amino acid sequence comprises SEQ ID NO:34, or (b) an amino acid sequence of a coat protein of CMV comprising an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:34.

In another preferred embodiment, said CMV polypeptide comprises, or preferably consists of, (i) (a) an amino acid sequence of a coat protein of CMV, wherein said amino acid sequence comprises, or preferably consists of, SEQ ID NO:15 or (b) an amino acid sequence having a sequence identity of at least 75%, preferably of at least 80%, more preferably of at least 85%, again further preferably of at least 90%, again more preferably of at least 95%, still further preferably of at least 98% and still again further more preferably of at least 99% of SEQ ID NO:15; and wherein said amino sequence as defined in (a) or (b) in this claim comprises SEQ ID NO:34; or wherein said amino sequence as defined in (a) or (b) in this claim comprises an amino acid sequence region, wherein said amino acid sequence region has a sequence identity of at least 75%, preferably of at least 80%, more preferably of at least 85%, again further preferably of at least 90%, again more preferably of at least 95%, still further preferably of at least 98% and still again further more preferably of at least 99% with SEQ ID NO:34; or (ii) a mutated amino acid sequence, wherein said amino acid sequence to be mutated is said amino acid sequence as defined in (i) of this claim, and wherein said mutated amino acid sequence and said amino acid sequence to be mutated show a sequence identity of at least 98% preferably of at least 99%.

In another preferred embodiment, said CMV polypeptide comprises, or preferably consists of, (a) an amino acid sequence of a coat protein of CMV, wherein said amino acid sequence comprises, or preferably consists of, SEQ ID NO:15 or (b) an amino acid sequence having a sequence identity of at least 90% of SEQ ID NO:15; and wherein said amino sequence as defined in (a) or (b) in this claim comprises SEQ ID NO:34; or wherein said amino sequence as defined in (a) or (b) in this claim comprises an amino acid sequence region, wherein said amino acid sequence region has a sequence identity of at least 90% with SEQ ID NO:34.

In another preferred embodiment, said T helper cell epitope replaces a N-terminal region of said CMV polypeptide. In another preferred embodiment the number of amino acids of said N-terminal region replaced is equal to or lower than the number of amino acids of which said T helper cell epitope consists.

In a further very preferred embodiment, said T helper cell epitope replaces a N-terminal region of said CMV polypeptide, and wherein the number of amino acids of said N-terminal region replaced is equal to or lower than the number of amino acids of which said T helper cell epitope consists.

Typically and preferably, said replaced N-terminal region of said CMV polypeptide consists of 5 to 15 consecutive amino acids, preferably of 9 to 14 consecutive amino acids, more preferably of 11 to 13 consecutive amino acids.

In a further very preferred embodiment, said N-terminal region of said CMV polypeptide corresponds to amino acids 2-12 of SEQ ID NO:15.

In another very preferred embodiment, said T helper cell epitope is a universal T helper cell epitope. In another preferred embodiment, said T helper cell epitope consists of at most 20 amino acids.

In a very preferred embodiment, said Th cell epitope is a PADRE sequence. In a further very referred embodiment, said Th cell epitope comprises, preferably consists of, the amino acid sequence of SEQ ID NO:19. In another very preferred embodiment, said Th cell epitope is a PADRE sequence, and wherein said Th cell epitope comprises, preferably consists of, the amino acid sequence of SEQ ID NO:19.

In another preferred embodiment, said T helper cell epitope is derived from a human vaccine. In a very preferred embodiment, said Th cell epitope is derived from tetanus toxin. In a further very referred embodiment, said Th cell epitope has, preferably consists of, the amino acid sequence of SEQ ID NO:18. In another very preferred embodiment, said Th cell epitope is derived from tetanus toxin, and wherein said Th cell epitope has, preferably consists of, the amino acid sequence of SEQ ID NO:18.

In a very preferred embodiment, said Th cell epitope is a PADRE sequence, and wherein said Th cell epitope comprises, preferably consists of, the amino acid sequence of SEQ ID NO:19; or wherein said Th cell epitope is derived from tetanus toxin, and wherein said Th cell epitope has, preferably consists of, the amino acid sequence of SEQ ID NO:18.

In a very preferred embodiment, said CMV polypeptide comprises, or preferably consists of, an amino acid sequence of a coat protein of CMV, wherein said amino acid sequence comprises, or preferably consists of, SEQ ID NO:15 or an amino acid sequence having a sequence identity of at least 95% of SEQ ID NO:15; and wherein said amino sequence comprises SEQ ID NO:34, and wherein said T helper cell epitope replaces the N-terminal region of said CMV polypeptide, and wherein said replaced N-terminal region of said CMV polypeptide consists of 11 to 13 consecutive amino acids, preferably of 11 consecutive amino acids, and wherein further preferably said N-terminal region of said CMV polypeptide corresponds to amino acids 2-12 of SEQ ID NO:15.

In another very preferred embodiment, said modified CMV polypeptide comprises, preferably consists of, an amino acid sequence of SEQ ID NO:20. In another very preferred embodiment, said modified CMV polypeptide comprises, preferably consists of, an amino acid sequence of SEQ ID NO:21.

In a very preferred embodiment, said first attachment site and said second attachment site are linked via at least one covalent non-peptide-bond. In another very preferred embodiment, said first attachment site comprises, or preferably is, an amino group, preferably an amino group of a lysine. In a further very preferred embodiment, said second attachment site comprises, or preferably is, a sulfhydryl group, preferably a sulfhydryl group of a cysteine.

In a very preferred embodiment, the at least one first attachment site is an amino group, preferably an amino group of a lysine residue and the at least one second attachment site is a sulfhydryl group, preferably a sulfhydryl group of a cysteine residue or a sulfhydryl group that has been chemically attached to the at least one antigen of the invention. In a further preferred embodiment only one of said second attachment sites associates with said first attachment site through at least one non-peptide covalent bond leading to a single and uniform type of binding of said antigen to said modified virus-like particle, wherein said only one second attachment site that associates with said first attachment site is a sulfhydryl group, and wherein said antigen and said modified virus-like particle interact through said association to form an ordered and repetitive antigen array.

In one preferred embodiment of the invention, the antigen is linked to the modified VLP by way of chemical cross-linking, typically and preferably by using a heterobifunctional cross-linker. In preferred embodiments, the hetero-bifunctional cross-linker contains a functional group which can react with the preferred first attachment sites, preferably with the amino group, more preferably with the amino groups of lysine residue(s) of the modified VLP, and a further functional group which can react with the preferred second attachment site, i.e. a sulfhydryl group, preferably of cysteine(s) residue inherent of, or artificially added to the antigen, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, Sulfo-KMUS SVSB, SIA, and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the antigen and the modified VLP upon coupling. Preferred cross-linkers belonging to this class include, for example, SPDP and Sulfo-LC-SPDP (Pierce).

Linking of the antigen to the modified VLP by using a hetero-bifunctional cross-linker according to the preferred methods described above, allows coupling of the antigen to the modified VLP in an oriented fashion. Other methods of linking the antigen to the modified VLP include methods wherein the antigen is cross-linked to the modified VLP, using the carbodiimide EDC, and NHS. The antigen may also be first thiolated through reaction, for example with SATA, SATP or iminothiolane. The antigen, after deprotection if required, may then be coupled to the modified VLP as follows. After separation of the excess thiolation reagent, the antigen is reacted with the modified VLP, previously activated with a hetero-bifunctional cross-linker comprising a cysteine reactive moiety, and therefore displaying at least one or several functional groups reactive towards cysteine residues, to which the thiolated antigen can react, such as described above. Optionally, low amounts of a reducing agent are included in the reaction mixture. In further methods, the antigen is attached to the modified VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the modified VLP.

In very preferred embodiments of the invention, the antigen is linked via a cysteine residue, having been added to either the N-terminus or the C-terminus of, or a natural cysteine residue within the antigen, to lysine residues of the modified virus-like particle. In a preferred embodiment, the composition of the invention further comprises a linker, wherein said linker associates said antigen with said second attachment site, and wherein preferably said linker comprises or alternatively consists of said second attachment site.

In a further very preferred embodiment of the invention, said core particle is a virus-like particle (VLP), preferably a recombinant VLP and said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5, SEQ ID NO:35, SEQ ID NO:36, SEQ ID NO:37 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:35, SEQ ID NO:36 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:36. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:38.

In a further very preferred embodiment of the invention, said core particle is a modified VLP, preferably a recombinant modified VLP, in accordance with the present invention and said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5, SEQ ID NO:35, SEQ ID NO:36, SEQ ID NO:37 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:35, SEQ ID NO:36 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:36. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:38.

In a further very preferred embodiment of the invention, said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, wherein said modified CMV polypeptide comprises, or preferably consists of (a) a CMV polypeptide, and (b) a T helper cell epitope; and wherein said CMV polypeptide comprises, or preferably consists of, (i) an amino acid sequence of a coat protein of CMV; or (ii) a mutated amino acid sequence, wherein the amino acid sequence to be mutated is an amino acid sequence of a coat protein of CMV, and wherein said mutated amino acid sequence and said coat protein of CMV show a sequence identity of at least 90%, preferably of at least 95%, further preferably of at least 98% and again more preferably of at least 99%, and wherein said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5, SEQ ID NO:35, SEQ ID NO:36, SEQ ID NO:37 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:35, SEQ ID NO:36 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:36. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:38.

In a further very preferred embodiment of the invention, said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, and wherein said modified CMV polypeptide comprises, preferably consists of, an amino acid sequence of SEQ ID NO:20 and said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5, SEQ ID NO:35, SEQ ID NO:36, SEQ ID NO:37 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:35, SEQ ID NO:36 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:36. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:38.

said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, and wherein said modified CMV polypeptide comprises, preferably consists of, an amino acid sequence of SEQ ID NO:21 and said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1.

In a further aspect, the present invention provides for an immunogenic or vaccine composition comprising an effective amount of the inventive composition, wherein optionally said immunogenic or vaccine composition further comprises an adjuvant.

In a further aspect, the present invention provides for a pharmaceutical composition comprising: (a) the inventive composition or the inventive immunogenic or vaccine composition; and (b) a pharmaceutically acceptable carrier.

In a further aspect, the present invention provides for a method of immunization, wherein said method comprises administering the inventive composition, the inventive immunogenic or vaccine composition or the inventive pharmaceutical composition to an equine mammal, preferably to a horse.

In a further aspect, the present invention provides for the inventive composition, the inventive immunogenic or vaccine composition, or the inventive pharmaceutical composition for use as a medicament.

In a further aspect, the present invention provides for the inventive composition, the inventive immunogenic or vaccine composition, or the inventive pharmaceutical composition for use in a method of prevention or treatment of insect bite hypersensitivity of an equine mammal, preferably of a horse, wherein an effective amount of said inventive composition, said inventive immunogenic or vaccine composition, or said inventive pharmaceutical composition is administered to said equine mammal, preferably to said horse. Preferably, said administration of said inventive composition, said inventive immunogenic or vaccine composition, or said inventive pharmaceutical composition reduces at least one IBH parameter or symptom when compared to said at least one IBH parameter or symptom before said administration, and wherein preferably said at least one IBH parameter or symptom is the level or severity grade of skin lesions, and wherein further preferably said reduction of said level or severity grade of skin lesions is determined by a symptom lesion scoring test, typically and preferably as described in Example 13. In a preferred embodiment, said reduction in the level or severity of skin lesions of said equine mammal, preferably of said horse, is expressed by a less positive symptom lesion scoring test, wherein typically and preferably said symptom lesion scoring test is effected as described in Example 13.

In a further aspect, the present invention provides for the inventive composition, the inventive immunogenic or vaccine composition, or the inventive pharmaceutical composition for use in a method of treatment of insect bite hypersensitivity of an equine mammal, preferably of a horse, wherein an effective amount of said inventive composition, said inventive immunogenic or vaccine composition, or said inventive pharmaceutical composition is administered to said equine mammal, preferably to said horse. Preferably, said administration of said inventive composition, said inventive immunogenic or vaccine composition, or said inventive pharmaceutical composition reduces at least one IBH parameter or symptom when compared to said at least one IBH parameter or symptom before said administration, and wherein preferably said at least one IBH parameter or symptom is the level or severity grade of skin lesions, and wherein further preferably said reduction of said level or severity grade of skin lesions is determined by a symptom lesion scoring test, typically and preferably as described in Example 13. In a preferred embodiment, said reduction in the level or severity of skin lesions of said equine mammal, preferably of said horse, is expressed by a less positive symptom lesion scoring test, wherein typically and preferably said symptom lesion scoring test is effected as described in Example 13.

In a further aspect, the present invention provides for the inventive composition, the inventive immunogenic or vaccine composition, or the inventive pharmaceutical composition for use in a method of treatment of insect bite hypersensitivity of a horse, wherein an effective amount of said inventive composition, said inventive immunogenic or vaccine composition, or said inventive pharmaceutical composition is administered to said horse, and wherein said core particle is a VLP, preferably a recombinant VLP, wherein said VLP is a modified VLP of cucumber mosaic virus (CMV), wherein said modified VLP of CMV comprises, essentially consists of, or alternatively consists of, at least one modified CMV polypeptide, and wherein said modified CMV polypeptide comprises, preferably consists of, an amino acid sequence of SEQ ID NO:20 and said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1. In again a very preferred embodiment of the invention, said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 95%, and preferably of at least 98% amino acid sequence identity with SEQ ID NO:1. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:1, SEQ ID NO:2, SEQ ID NO:5, SEQ ID NO:35, SEQ ID NO:36, SEQ ID NO:37 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence selected from SEQ ID NO:35, SEQ ID NO:36 and SEQ ID NO:38. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:36. In again a very preferred embodiment of the invention, said modified CMV polypeptide comprises, preferably consists of, an amino acid sequence of SEQ ID NO:20 and said at least one antigen is an equine Interleukin-5 antigen (eIL-5 antigen), and wherein said eIL-5 antigen comprises, or preferably is, a protein with the amino sequence of SEQ ID NO:38. In another very preferred embodiment, said modified CMV polypeptide comprises, preferably consists of, an amino acid sequence of SEQ ID NO:21 and said at least one antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1.

In a further aspect, the present invention provides for a method of prevention or treatment of insect bite hypersensitivity, wherein said method comprises administering an effective amount of said inventive composition, said inventive immunogenic or vaccine composition, or said inventive pharmaceutical composition to an equine mammal, preferably to a horse.

In a further aspect, the present invention provides for a method of treatment of insect bite hypersensitivity, wherein said method comprises administering an effective amount of said inventive composition, said inventive immunogenic or vaccine composition, or said inventive pharmaceutical composition to an equine mammal, preferably to a horse.

In a further aspect, the present invention provides for an immunogenic or vaccine composition comprising an effective amount of a first composition and an effective amount of a second composition, wherein said first composition comprises (a) a first core particle with at least one first attachment site; and (b) at least one first antigen with at least one second attachment site, wherein said at least one first antigen is an equine Interleukin-5 antigen (eIL-5 antigen), wherein said eIL-5 antigen comprises, or preferably is, a protein with the amino sequence selected from SEQ ID NO:1 or a protein with an amino acid sequence of at least 90%, preferably of at least 92%, further preferably of at least 95%, and again further preferably of at least 98% amino acid sequence identity with SEQ ID NO:1; and wherein said second composition comprises (c) a second core particle with at least one first attachment site; and (d) at least one second antigen with at least one second attachment site, wherein said at least one second antigen is an equine Eotaxin antigen (eEotaxin antigen), wherein said eEotaxin antigen comprises, or preferably is, a protein with the amino sequence selected from SEQ ID NO:6 or a protein with an amino acid sequence of at least 90%, preferably of at least 92%, further preferably of at least 95%, and again further preferably of at least 98% amino acid sequence identity with SEQ ID NO:6; and wherein (a) and (b) are linked through said at least one first and said at least one second attachment site via at least one non-peptide covalent bond, and wherein (c) and (d) are linked through said at least one first and said at least one second attachment site via at least one non-peptide covalent bond; and wherein optionally said immunogenic or vaccine composition further comprises an adjuvant.

In a preferred embodiment, said immunogenic or vaccine composition further comprises a third composition, wherein said third composition comprises (e) a third core particle with at least one first attachment site; and (f) at least one third antigen with at least one second attachment site, wherein said at least one third antigen is an equine Interleukin-31 antigen (eIL-31 antigen), wherein said eIL-31 antigen comprises, or preferably is, a protein with the amino acid sequence selected from SEQ ID NO:12 or a protein with an amino acid sequence of at least 90%, preferably of at least 92%, further preferably of at least 95%, and again further preferably of at least 98% amino acid sequence identity with SEQ ID NO:12; and wherein (e) and (f) are linked through said at least one first and said at least one second attachment site via at least one non-peptide covalent bond.

In a further aspect, the present invention provides for the inventive immunogenic or vaccine composition for use in a method of prevention or treatment of insect bite hypersensitivity of an equine mammal, preferably of a horse, wherein an effective amount of said composition is administered to said equine mammal, preferably to said horse. In a preferred embodiment, said administration of said inventive immunogenic or vaccine composition reduces at least one IBH parameter or symptom as compared to said at least one IBH parameter or symptom before said administration, and wherein preferably said at least one IBH parameter or symptom is the level or severity grade of skin lesions, and wherein further preferably said reduction of said level or severity grade of skin lesions is determined by a symptom lesion scoring test.

In a further aspect, the present invention provides for a kit for the prevention or treatment of insect bite hypersensitivity comprising the inventive composition, the inventive immunogenic or vaccine composition, or the inventive pharmaceutical composition and instructions for use of said kit.

In a further aspect, the present invention provides for a method for the treatment of IBH, comprising administering an effective amount of the inventive composition, or the immunogenic or vaccine composition, or the pharmaceutical composition to an equine mammal, preferably to a horse, wherein the effective amount is sufficient to ameliorate one or more of the symptoms of IBH.

EXAMPLES

Example 1

Cloning, Expression and Purification of Equine Interleukin-5 (eIL-5)

A. Cloning of eIL-5-C-his and Expression as Inclusion Bodies in *E. coli*

The DNA sequence encoding for mature eIL-5 (mature Interleukin-5, equus caballus; UniProt O02699) and fragments thereof were generated by gene-synthesis. SEQ ID NO:1, SEQ ID NO:2 and SEQ ID NO:3 have been generated. SEQ ID NO:1 corresponds to SEQ ID NO:2 but lacking the first amino acid L of SEQ ID NO:2, whereas SEQ ID NO:3 corresponds to the full-length eIL-5 sequence identified as UniProt O02699.

In addition a linker (GGC) was added C-terminally. This insert was flanked by 5' NdeI and 3' XhoI and was integrated into pET 42b(+), containing an octa His-tag (to facilitate purification) and stop codon in frame. The construct was termed pET42b-eIL-5 (SEQ ID NO:4). Fidelity of the cloning procedure was confirmed by DNA sequencing. The construct pET42b-eIL-5 (SEQ ID NO:4) was transformed into *E. coli* strain BL21-DE3. The recombinant protein expressed in *E. coli* is termed eIL-5-C-His (SEQ ID NO:5). Analogously, SEQ ID NO:35, SEQ ID NO:36 and SEG ID NO:37 have been prepared, all comprising a cysteine residue comprising linker and a His-tag, with SEQ ID NO:35 and SEQ ID NO:36 comprising a linker (GGC) and a His-tag C-terminally. SEQ ID NO:5, SEQ ID NO:35, SEQ ID NO:36 and SEG ID NO:37 are interchangeably termed herein as "eIL-5-C-His". Furthermore, when it is referred to eIL-5-C-His within this example section and the described figures, one of these eIL-5-C-His recombinant proteins have been used, in various examples even more than one or all been used in repeated experiments. Very preferred used eIL-5-C-His are SEQ ID NO:5, SEQ ID NO:35 and SEQ ID NO:36. A larger scale expression of eIL-5-C-His from clone pET42b-eIL5-C-His in BL21-DE3 cells was performed. For this purpose, clonal BL21-DE3 cells harboring pET42b-eIL-5-C-His were grown over night in 180 ml of LB containing 50 mg/L Kanamycin. Inoculate with this culture 10 L LB containing 50 mg/L Kanamycin. The culture was grown to an optical density, $OD_{600\ nm}$, of 0.7 and expression induced for 4 hours by adding 10 ml of a 1.0 M stock of Isopropyl β-D-Thiogalactopyranoside (IPTG). Recombinant eIL-5-C-His was expressed in an insoluble form and located in the inclusion body fraction of induced cells. Expression of eIL-5-C-His was confirmed in the flowing manner. The culture was taken 4 hours after induction and centrifuged for 10 min at 4200×g at 4° C. The pellet was resuspended with resuspension buffer (100 mM Tris/HCl pH 8.0 at 4° C., 1 mM EDTA) (3 ml/g of cells) using an ultraturex (800 rpm). Resuspended cells were collected in Falcon tubes and shock freeze in liquid nitrogen and stored at −20° C. overnight. Resuspended cells were unfrozen at room temperature and open cells by a cell-cracker or dounce homogenizer and sonicator (50 μl sample for gel analysis: sample A=lysate, 50 μl). 0.5 volumes of cold triton buffer (60 mM EDTA, 1.5 M NaCl, adjust to pH 7.0 with NaOH then add 6% (v/v) Triton-X-100) were added and stirred for 30 min at 4° C. Thereafter, lysate was centrifuged for 30 min at 4800×g and 4° C. (50 μl sample for gel analysis: sample B=soluble fraction, 50 ml). Inclusion bodies were resuspended in washing buffer (100 mM Tris/HCl pH 8.0 at 4° C., 20 mM EDTA) with ultraturrax and centrifuged for 10 min at 48000×g and 4° C. This washing step was repeated four times to remove triton-x 100 and finally inclusion bodies were stored at −20° C. Inclusion bodies were unfrozen at room temperature and were solubilized by resuspension in solubilization buffer (6 M GdmCl, 20 mM Immidazol, 100 mM Tris-HCl pH 8 at room temperature) (20 ml/g of inclusion bodies) using ultraturex and stirring 1-2 h at room temperature. Solubilized inclusion bodies were ultra-centrifuged for 20 min at 20° C. at 100000×g on average (50 μl sample for gel analysis: sample C=solubilized IBs 50 μl).

B. Purification and Refolding of eIL-5-C-His

The protein was purified via the His-tag by Ni-NTA resin (Ni-NTA Sepharose 6 Fast Flow, Amersham, CatNo 17-5318-01 or Ni-NTA Sepharose SUperflow, Quiagen, CatNo 1018142) column with solubilization buffer as binding buffer A and elution by buffer B (6 M GdmCl, 100 mM NaH$_2$PO$_4$, 10 mM TrisHCl, pH 4.5) (50 μl sample for gel analysis: sample D=flow thru NiNTA; 50 μl, sample E=peak NiNTA 50 μl). Purification was analyzed by SDS-PAGE. The fractions from the elution step containing eIL-5-C-His were pooled and dialyzed against 6 M GdmCl, 100 mM NaH$_2$PO$_4$, 10 mM Tris, pH 8.0 for 2 h at room temperature using a 10 kDa cut-off membrane.

Figure 1:
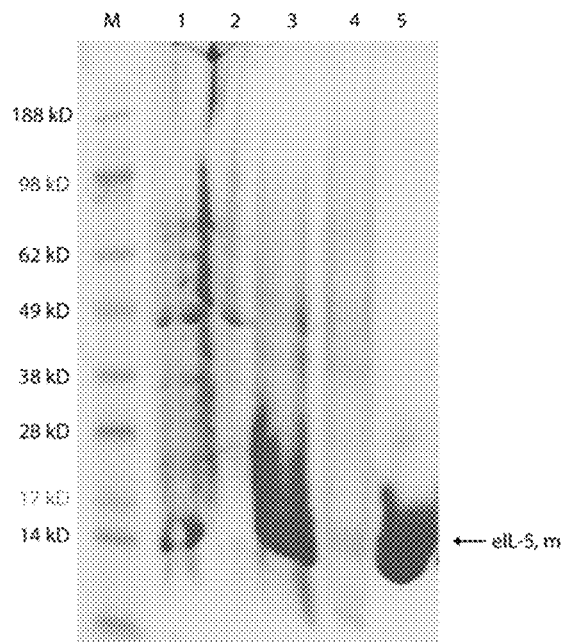
FIG. 1: SDS-PAGE analysis of the purification of eIL-5-C-His with NiNTA. Samples from various stages of the inclusion body preparation and purification were applied to a 4-12% Bis-Tris Gel (NuPAGE, Novex, Invitrogen Life Technologies) and run under reducing conditions. Proteins were stained with Coomassie blue. Lane M, Size Marker (See Blue, pre-stained, NuPAGE, Novex, Invitrogen Life Technologies), lane 1, Lysate (sample A), lane 2, soluble fraction (sample B), lane 3, solubilized inclusion bodies (sample C), lane 4, flow through (unbound material, sample D), lane 5, pooled eIL-5 monomer (eIL-5, m) eluate from Ni-NTA column (sample E).

Insoluble eIL-5-C-His was extracted from detergent washed inclusion bodies with 6M guanidine hydrochloride. Different washing steps were analyzed by SDS-PAGE (FIG. 1): lysate (FIG. 1, lane 1), soluble fraction (FIG. 1, lane 2), solubilized inclusion bodies (FIG. 1, lane 3). The solubilized protein was purified by metal chelate affinity chromatography and analyzed by SDS-PAGE (FIG. 1, lane 4, flow through, lane 5, pooled fractions eluate). Recombinant eIL- 5-C-His was found to be highly enriched by this procedure. The native protein was assessed by SDS-PAGE (FIG. 2) performed under non-reducing conditions (with SDS, no DTT, no heating of samples) (FIG. 2, lane 1) and mainly monomeric protein was found. The denatured protein was subjected to a refolding procedure as described below and optionally further purified by size exclusion chromatography.

In order to refold eIL-5-C-His, the protein was dialyzed sequentially by the following buffers: buffer 1 (2 M Urea, 50 mM $NaH_2PO_4$, 5 mM Glutathione reduced, 0.5 mM Gluthatione oxidized, 0.5 M Arginine, 10% Glycerol), buffer 2 (50 mM $NaH_2PO_4$, 5 mM Glutathione reduced, 0.5 mM Gluthatione oxidized, 0.5 M Arginine, 10% Glycerol), buffer 3 (50 mM $NaH_2PO_4$, 10% Glycerol), buffer 4 (PBS). Optionally refolded protein was concentrated by Centrifugal Filters (Amicon, Ultrafree-15 Millipore, 10 kDa cut-off) and purified on a HiLoad 26/60 Superdex 75 prep grade (GE Healthcare, CatNo 28-9893-34) with PBS buffer. Eluted fractions were pooled and analyzed by a non-reducing SDS-PAGE. Protein concentration was measured by UV-VIS or Bradford assay.

Figure 2:
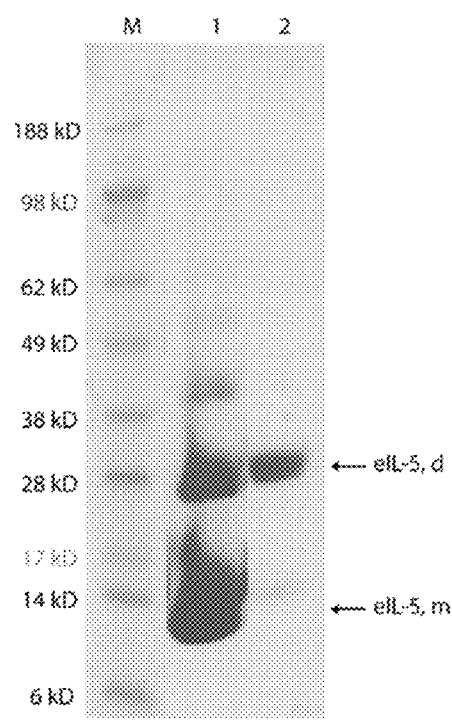
FIG. 2: SDS-PAGE refolded recombinant eIL-5-C-His. Protein was refolded and concentrated as described above. An aliquote was separated on a 4-12% Bis-Tris Gel (NuPAGE, Novex, Invitrogen Life Technologies) and run under native conditions (+SDS, no DTT, no heating). Proteins were stained with Coomassie blue: eIL-5 monomer (eIL-5, m), eIL-5 dimer (eIL-5, d). Lane M, Size Marker (See Blue, pre-stained, NuPAGE, Novex, Invitrogen Life Technologies), lane 1, pooled denatured eluate from Ni-NTA column, lane 2, refolded and homodimer enriched eIL-5-C-His.

Since biologically active native IL-5 is a disulfide-linked homodimer, the ability of purified recombinant eIL-5-C-His to form dimers after refolding was assessed by SDS-PAGE performed under non-reducing conditions (FIG. 2, lane 2). As judged by the molecular mass of approximately 28 kDa, eIL-5-C-His was demonstrated to be dimeric in nature indicating conservation of the native tertiary structure.

C. Structure of Recombinant Homodimer Enriched eIL-5-C-His

Figure 3A:
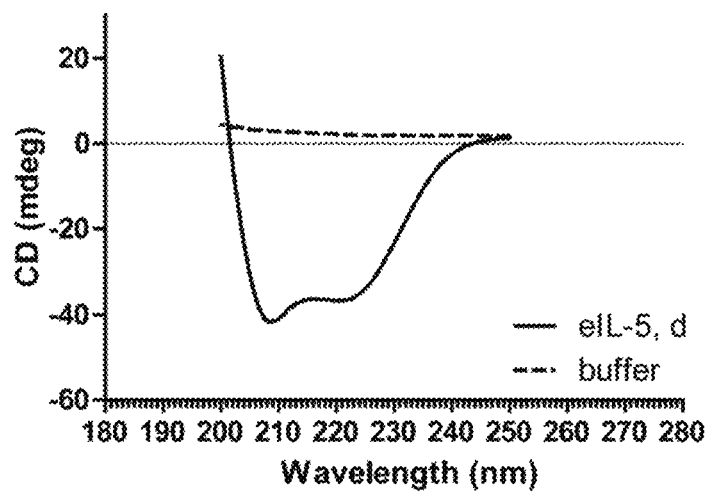
FIG. 3A: Correct structure of refolded recombinant eIL-5-C-His. Circular dichroism (CD) spectroscopy of refolded and homodimer enriched eIL-5-C-His in comparison to PBS buffer (dotted line). Secondary structure of IL-5-C-His reflecting α-helices and β-sheets measured by far-UV (ultraviolet) CD spectra.

CD spectroscopy by far-UV showing α-helices and β-sheets was measured in order to confirm correct secondary structure (FIG. 3A).

Mass spectrometry (MALDI/MS/MS of digested eIL-5-C-His followed by HPLC) was performed in order to confirm besides secondary also the primary, tertiary and quaternary structure of the protein. Typically IL-5 monomers are linked as homodimers by two intermolecular disulfide bridges leading to a head to tail position of the two monomers.

Figure 3B:
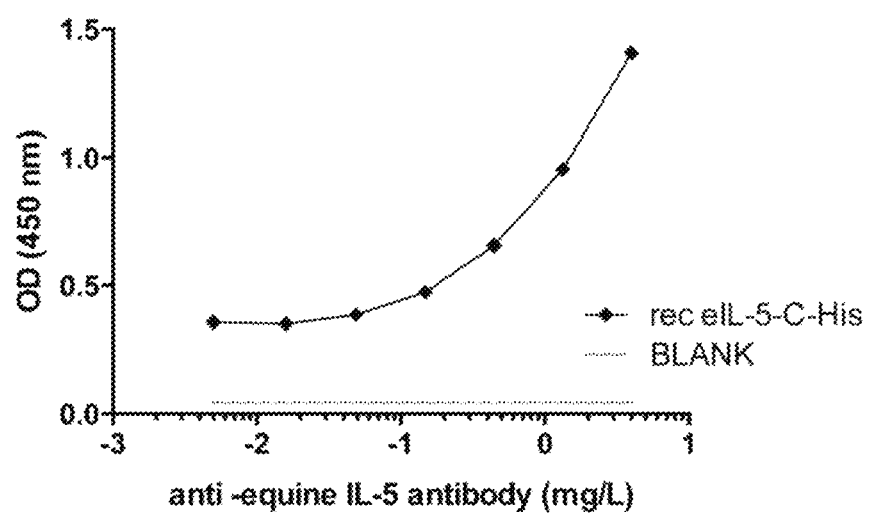
FIG. 3B: Correct structure of refolded recombinant eIL-5-C-His. Homodimer enriched eIL-5-C-His can be detected by a commercially available anti-eIL-5 antibody. Anti-His antibody coated ELISA plates were incubated with recombinantly expressed and refolded homodimer enriched eIL-5 and detected by a commercially available anti-equine IL-5 antibody (R&D Systems, UK).
Figure 4:
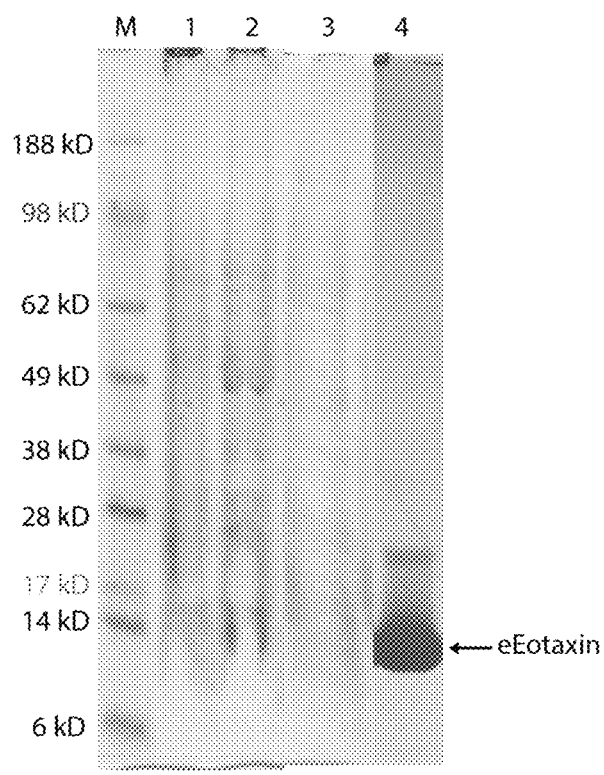
FIG. 4: SDS-PAGE refolded recombinant eEotaxin-C-His.

The ability of a commercially available antibody binding to the recombinant eIL-5-C-His was tested by ELISA (FIG. 3B). Maxisorp 96 well ELISA plates (Nunc) were coated over night with 50 µl of anti-His antibody at 0.5 mg/L. Plates were washed 3 times with PBS-Tween 0.1% (v/v) (PBST) then blocked with Superblock (Thermo Scientific) for 1 h at 37° C. Plates were washed twice with PBST and purified recombinant eIL-5-C-His (10 mg/L) was added and incubated for 1 h. Then plates were washed 3 times with PBST and anti eIL-5 antibody (Equine IL-5 affinity purified polyclonal antibody, R&D Systems, UK, CatNo AF2470) was titrated down from 4 µg/ml in 1/3 dilutions and incubated at room temperature for 2 h. The plates were subsequently washed 3 times with PBST and incubated with a secondary anti-goat IgG conjugated with HRP (dilution 1:2000) at room temperature for 30 min. The plates were again washed 3 times with PBS and 50 µl/well developing solution (TMB) were added. After 2 minutes of reaction at room temperature the ELISA was stopped with 25 µl per well 5% $H_2SO_4$. Absorbance was measured at 450 nm on a Tecan M200 spectrophotometer (Tecan, Austria).

The proper refolding of recombinant eIL-5-C-His was measured by circular dichroism (CD) spectroscopy and in majority α helices but also β sheets could be found as expected (FIG. 3A). The linkage of two monomers by two intermolecular disulfide bridges was further confirmed by MALDI/MS/MS. MSMS fractions of mass 2505, 2633, and 2761 m/z show the typical disulfide fragment pattern 32/2/32. Two monomers are linked via 2 disulfide bridges as Cys44 is linked to Cys 86 intermolecularly (spectra not shown). Furthermore, refolded equine IL-5-C-His was detectable by a commercially available anti-equine IL-5 antibody in an ELISA (FIG. 3B).

Example 2

Cloning, Expression and Purification of Equine Eotaxin (eEotaxin)

A. Cloning of eEotaxin-C-his and Expression as Inclusion Bodies in *E. coli*

The DNA sequence encoding for mature eEotaxin (mature Eotaxin, equus caballus; UniProt Q9TTQ4) and fragments thereof were generated by gene-synthesis. SEQ ID NO:6, SEQ ID NO:7 and SEQ ID NO:8 have been generated. SEQ ID NO:6 corresponds to SEQ ID NO:7 but lacking the first amino acid Q of SEQ ID NO:7, whereas SEQ ID NO:8 corresponds to the full-length eEotaxin sequence identified as UniProt Q9TTQ4.

In addition a linker (GGC) was added C-terminally. This insert was flanked by 5' NdeI and 3' XhoI and was integrated into pET 42b(+), containing an octa His-tag (to facilitate purification) and stop codon in frame. The construct was termed pET42b-eEotaxin (SEQ ID NO:9). Fidelity of the cloning procedure was confirmed by DNA sequencing. The construct pET42b-eEotaxin (SEQ ID NO:9) was transformed into *E. coli* strain BL21-DE3. The recombinant protein expressed in *E. coli* is termed eEotaxin-C-His (SEQ ID NO:10).

A larger scale expression of eEotaxin-C-His from clone pET42b-eEotaxin-C-His in BL21-DE3 cells was performed. For this purpose, clonal BL21-DE3 cells harboring pET42b-eEotaxin-C-His were grown over night in 180 ml of LB containing 50 mg/L Kanamycin. Inoculate with this culture 10 L LB containing 50 mg/L Kanamycin. The culture was grown to an optical density, $OD_{600\,nm}$, of 0.7 and expression induced for 4 hours by adding 10 ml of a 1.0 M stock of Isopropyl β-D-Thiogalactopyranoside (IPTG). Recombinant eEotaxin-C-His was expressed in an insoluble form and located in the inclusion body fraction of induced cells. Expression of eEotaxin-C-His was confirmed in the flowing manner. The culture was taken 4 hours after induction and centrifuged for 10 min at 4200×g at 4° C. The pellet was resuspended with resuspension buffer (100 mM Tris/HCl pH 8.0 at 4° C., 1 mM EDTA) (3 ml/g of cells) using an ultraturex (800 rpm). Resuspended cells were collected in Falcon tubes and shock freeze in liquid nitrogen and stored at −20° C. overnight. Resuspended cells were unfrozen at room temperature and open cells by a cell-cracker or dounce homogenizer and sonicator (50 µl sample for gel analysis: sample A=lysate, 50 µl). 0.5 volumes of cold triton buffer (60 mM EDTA, 1.5 M NaCl, adjust to pH 7.0 with NaOH then add 6% (v/v) Triton-X-100) were added and stirred for 30 min at 4° C. Thereafter, lysate was centrifuged for 30 min at 4800×g and 4° C. (50 µl sample for gel analysis: sample B=soluble fraction, 50 ml). Inclusion bodies were resuspend in washing buffer (100 mM Tris/HCl pH 8.0 at 4° C., 20 mM EDTA) with ultraturrax and centrifuged for 10 min at 48000×g and 4° C. This washing step was repeated four times to remove triton-x 100 and finally inclusion bodies were stored at −20° C. Inclusion bodies were unfrozen at room temperature and were solubilized by resuspension in solubilization buffer (6 M GdmCl, 20 mM Immidazol, 100 mM Tris-HCl pH 8 at room temperature) (20 ml/g of inclusion bodies) using ultraturex and stirring 1-2 h at room temperature. Solubilized inclusion bodies were ultra-centrifuged for 20 min at 20° C. at 100000×g on average (50 µl sample for gel analysis: sample C=solubilized IBs 500.

B. Purification and Refolding of eEotaxin-C-His

The protein was purified via the His-tag by Ni-NTA resin (Ni-NTA Sepharose 6 Fast Flow, Amersham, CatNo 17-5318-01 or Ni-NTA Sepharose SUperflow, Quiagen, CatNo 1018142) column with solubilization buffer as binding buffer A and elution by buffer B (6 M GdmCl, 100 mM $NaH_2PO_4$, 10 mM TrisHCl, pH 4.5) (50 μl sample for gel analysis: sample D=flow thru NiNTA; 50 μl, sample E=peak NiNTA 50 μl). Purification was analyzed by SDS-PAGE. The fractions from the elution step containing eEotaxin-C-His were pooled and dialyzed against 6 M GdmCl, 100 mM $NaH_2PO_4$, 10 mM Tris, pH 8.0 for 2 h at room temperature using a 10 kDa cut-off membrane. Protein was refolded by rapid dilution in refolding buffer (0.1 M TrisHCl, pH 8.0 at 4° C., 1 mM oxidized Glutathione, 0.1 mM reduced Glutathione) for 12 hours at 4° C. and at 50 μg/ml. Refolded protein was further concentrated using a crossflow and the buffer was exchanged to PBS (Sartorius, VivaFlow 200, 5 kDa cut-off). Optionally refolded protein was concentrated by Centrifugal Filters (Amicon, Ultrafree-15 Millipore, 3 kDa cut-off) and purified on a HiLoad 26/60 Superdex 75 prep grade (GE Healthcare, CatNo 28-9893-34) with PBS buffer. Protein concentration was measured by UV-VIS or Bradford assay.

Insoluble eEotaxin-C-His was extracted from detergent washed inclusion bodies with 6M guanidine hydrochloride. Different washing steps were analyzed by SDS-PAGE (FIG. 4): lysate (FIG. 4, lane 1), soluble fraction (FIG. 4, lane 2). The solubilized protein from inclusion bodies was purified by metal chelate affinity chromatography, refolded and analyzed by SDS-PAGE (FIG. 4, lane 3, flow through, lane 4, pooled fractions of column refolded eluate). Recombinant eEotaxin-C-His was found to be highly enriched by this procedure and mainly monomeric form was found. Optionally further purified by size exclusion chromatography.

C. Structure of Recombinant Refolded Equine Eotaxin

The ability of a commercially available antibody binding to the recombinant eEotaxin-C-His was tested by ELISA (FIG. 5). Test wells: Maxisorp 96 well ELISA plates (Nunc) were coated over night with 50 μl at 10 mg/L of eEotaxin-C-His or commercially available equine CCL-11 protein (recombinant equine CCL-11, Kingfisher Biotech Inc., CatNo RP0066E). Plates were washed 3 times with PBS-Tween 0.1% (v/v) (PBST) then blocked with Superblock (Thermo Scientific) for 2 h at room temperature. Plates were washed 3 times with PBST and anti CCL-11 antibody (anti CCL-11 polyclonal antibody with reactivity to equine CCL-11, Aviva, CatNo ARP30865_P050) was titrated down from 4 μg/ml in 1/3 dilutions and incubated at room temperature for 2 h. The plates were subsequently washed 3 times with PBST and incubated with a secondary anti-rabbit IgG conjugated with HRP (dilution 1:2000) at room temperature for 30 min. The plates were again washed 3 times with PBS and 50 μl/well developing solution (TMB) were added. After 2 minutes of reaction at room temperature the ELISA was stopped with 25 μl per well 5% $H_2SO_4$. Absorbance was measured at 450 nm on a Tecan M200 spectrophotometer (Tecan, Austria). Proper refolding of eEotaxin was confirmed by an ELISA. Refolded equine eEotaxin-C-His was detectable by a commercially available anti-CCL11 antibody with reactivity to equine CCL-11 (FIG. 5).

Example 3

Cloning, Expression and Purification of Equine IL-31 (eIL-31)

A. Cloning of eIL-31-C-His and Expression as Inclusion Bodies in *E. coli*

The DNA sequence encoding for mature eIL-31 (mature Eotaxin, equus caballus; UniProt F7AHG9) (SEQ ID: NO.11) and a fragment thereof (SEQ ID NO:12) were generated by gene-synthesis.

In addition a linker (GGC) was added C-terminally. This insert was flanked by 5' NdeI and 3' XhoI and was integrated into pET 42b (+), containing an octa His-tag (to facilitate purification) and stop codon in frame. The construct was termed pET42b-eIL-31 (SEQ ID NO:13). Fidelity of the cloning procedure was confirmed by DNA sequencing. The construct pET42b-eIL-31 (SEQ ID NO:13) was transformed into *E. coli* strain BL21-DE3. The recombinant protein expressed in *E. coli* is termed eIL-31-C-His (SEQ ID NO:14).

A larger scale expression of eIL-31-C-His from clone pET42b-eIL31-C-His in BL21-DE3 cells was performed. For this purpose, clonal BL21-DE3 cells harboring pET42b-eIL31-C-His were grown over night in 180 ml of LB containing 50 mg/L Kanamycin. Inoculate with this culture 10 L LB containing 50 mg/L Kanamycin. The culture was grown to an optical density, $OD_{600\ nm}$, of 0.7 and expression induced for 4 hours by adding 10 ml of a 1.0 M stock of Isopropyl β-D-Thiogalactopyranoside (IPTG). Recombinant eIL-31-C-His was expressed in an insoluble form and located in the inclusion body fraction of induced cells. Expression of eIL-31-C-His was confirmed in the flowing manner. The culture was taken 4 hours after induction and centrifuged for 10 min at 4200×g at 4° C. The pellet was resuspended with resuspension buffer (100 mM Tris/HCl pH 8.0 at 4° C., 1 mM EDTA) (3 ml/g of cells) using an ultraturex (800 rpm). Resuspended cells were collected in Falcon tubes and shock freeze in liquid nitrogen and stored at −20° C. overnight. Resuspended cells were unfrozen at room temperature and open cells by a cell-cracker or dounce homogenizer and sonicator (50 μl sample for gel analysis: sample A=lysate, 50 μl). 0.5 volumes of cold triton buffer (60 mM EDTA, 1.5 M NaCl, adjust to pH 7.0 with NaOH then add 6% (v/v) Triton-X-100) were added and stirred for 30 min at 4° C. Thereafter, lysate was centrifuged for 30 min at 4800×g and 4° C. (50 μl sample for gel analysis: sample B=soluble fraction, 50 ml). Inclusion bodies were resuspend in washing buffer (100 mM Tris/HCl pH 8.0 at 4° C., 20 mM EDTA) with ultraturrax and centrifuged for 10 min at 48000×g and 4° C. This washing step was repeated four times to remove triton-x 100 and finally inclusion bodies were stored at −20° C. Inclusion bodies were unfrozen at room temperature and were solubilized by resuspension in solubilization buffer (6 M GdmCl, 20 mM Immidazol, 100 mM Tris-HCl pH 8 at room temperature) (20 ml/g of inclusion bodies) using ultraturex and stirring 1-2 h at room temperature. Solubilized inclusion bodies were ultra-centrifuged for 20 min at 20° C. at 100000×g on average (50 μl sample for gel analysis: sample C=solubilized IBs 50 μl).

B. Purification and Refolding of eIL-31-C-His

The protein was purified via the His-tag by Ni-NTA resin (Ni-NTA Sepharose 6 Fast Flow, Amersham, CatNo 17-5318-01 or Ni-NTA Sepharose SUperflow, Quiagen, CatNo 1018142) column with solubilization buffer as binding buffer A and elution by buffer B (6 M GdmCl, 100 mM NaH$_2$PO$_4$, 10 mM TrisHCl, pH 4.5) (50 μl sample for gel analysis: sample D=flow thru NiNTA; 50 μl, sample E=peak NiNTA 50 μl). Purification was analyzed by SDS-PAGE. The fractions from the elution step containing eIL-31-C-His were pooled and dialyzed against 6 M GdmCl, 100 mM NaH$_2$PO$_4$, 10 mM Tris, pH 8.0 for 2 h at room temperature using a 8 kDa cut-off membrane.

Insoluble eIL-31-C-His was extracted from detergent washed inclusion bodies with 6M guanidine hydrochloride. Different washing steps were analyzed by SDS-PAGE (FIG. 6): lysate (FIG. 6, lane 1), soluble fraction (FIG. 6, lane 2), solubilized inclusion bodies (FIG. 6, lane 3). The solubilized protein was purified by metal chelate affinity chromatography and analyzed by SDS-PAGE (FIG. 6, lane 4, pooled fractions eluate). Recombinant eIL-31-C-His was found to be highly enriched by this procedure. The native protein was assessed by SDS-PAGE performed under non-reducing conditions (FIG. 7, lane 1) and mainly monomeric protein was found. The denatured protein was subjected to a refolding procedure as described below and optionally further purified by size exclusion chromatography.

In order to refold eIL-31-C-His, the protein was dialyzed sequentially by the following buffers: buffer 1 (2 M Urea, 50 mM NaH$_2$PO$_4$, 5 mM Glutathione reduced, 0.5 mM Gluthatione oxidized, 0.5 M Arginine, 10% Glycerol), buffer 2 (50 mM NaH$_2$PO$_4$, 5 mM Glutathione reduced, 0.5 mM Gluthatione oxidized, 0.5 M Arginine, 10% Glycerol), buffer 3 (50 mM NaH$_2$PO$_4$, 10% Glycerol), buffer 4 (PBS). Optionally refolded protein was concentrated by Centrifugal Filters (Amicon, Ultrafree-15 Millipore, 10 kDa cut-off) and purified on a HiLoad 26/60 Superdex 75 prep grade (GE Healthcare, CatNo 28-9893-34) with PBS buffer. Eluted fractions were pooled and analyzed by a non-reducing SDS-PAGE (with SDS, no DTT, no heating of samples). Protein concentration was measured by UV-VIS or Bradford assay.

The ability of purified recombinant eIL-31-C-His to form dimers after refolding was assessed by SDS-PAGE performed under non-reducing conditions (FIG. 7, lane 2). As judged by the molecular mass of approximately 33 kDa, eIL-31-C-His was demonstrated to partially exist in dimeric structure.

C. Biological Activity of Recombinant Refolded Equine eIL-31-C-His eIL-31-C-His was injected subcutaneously into the neck of a horse. Itch was defined as ≥5 seconds itching at the injection site (neck). The number of scratching/itching per hour was counted for 5 hours in total starting 1 hour post injection. Itching after injection with eIL-31-C-His was compared with injection of eIL-5-C-His control. An increased number of itching was recorded for eIL-31-C-His than for the control (FIG. 8).

Example 4

Isolation and Cloning of a Coat Protein (CP) of Cucumber Mosaic Virus (CMV)

Total RNA from CMV-infected lily leaves was isolated using TRI reagent (Sigma, Saint Louis, USA) in accordance with manufacturer's instructions. For cDNA synthesis, a OneStep RT-PCR kit (Qiagen, Venlo, Netherlands) was used. For amplification of the CMV CP gene, primer sequences were chosen following analysis of CMV sequences from GenBank: CMcpF (CA CCATGGACAAATCTGAATCAACCAGTGCTGGT) (SEQ ID NO:22) and CMcpR (CA AAGCTTATCAAACTGGGAGCACCCCAGATGTGGGA) (SEQ ID NO:23); NcoI and HindIII sites are underlined. The corresponding PCR products were cloned into the pTZ57R/T vector (Fermentas, Vilnius, Lithuania). *E. coli* XL1-Blue cells were used as a host for cloning and plasmid amplification. To avoid selecting clones containing PCR errors, several CP gene-containing pTZ57 plasmid clones were sequenced using a BigDye cycle sequencing kit and an ABI Prism 3100 Genetic analyzer (Applied Biosystems, Carlsbad, USA). After sequencing, a cDNA of the CMV CP gene without sequence errors (SEQ ID NO:24) coding for CMV coat protein of SEQ ID NO:15 was then subcloned into the NcoI/HindIII sites of the pET28a(+) expression vector (Novagen, San Diego, USA), resulting in the expression plasmid pET-CMVwt (FIG. 9).

Example 5

Expression of CP of SEQ ID NO:15 in *E. coli* Leading to VLPs of CMV

To obtain CMV VLPs, *E. coli* C2566 cells (New England Biolabs, Ipswich, USA) were transformed with the CMV CP gene-containing plasmid pET-CMVwt. After selection of clones with the highest expression levels of target protein, *E. coli* cultures were grown in 2×TY medium containing kanamycin (25 mg/l) on a rotary shaker (200 rev/min; Infors, Bottmingen, Switzerland) at 30° C. to an OD600 of 0.8-1.0. Then, the cells were induced with 0.2 mM IPTG, and the medium was supplemented with 5 mM MgCl2. Incubation was continued on the rotary shaker at 20° C. for 18 h. The resulting biomass was collected by low-speed centrifugation and was frozen at −20° C. After thawing on ice, the cells were suspended in the buffer containing 50 mM sodium citrate, 5 mM sodium borate, 5 mM EDTA, 5 mM mercaptoethanol (pH 9.0, buffer A) and were disrupted by ultrasonic treatment. Insoluble proteins and cell debris were removed by centrifugation (13,000 rpm, 30 min at 5° C.). The soluble CMV CP protein in clarified lysate was pelleted using saturated ammonium sulfate (1:1, vol/vol) overnight at +4° C. Precipitated proteins were solubilized in the same buffer A (without mercaptoethanol) for 4 h at +4° C. Insoluble proteins were removed by low speed centrifugation (13,000 rpm, 15 min at 4° C.). Soluble CMV CP-containing protein solution was separated from the cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient, and the fractions were analyzed by SDS-PAGE (data not shown). Fractions No. 2 and No. 3 containing recombinant CMV CP were combined and were dialyzed against 200 volumes of the buffer (5 mM sodium borate, 2 mM EDTA, pH 9.0) to remove the sucrose and Triton X-100. After dialysis, CMV CP solution was sterilized by filtration through the 0.2 μl filter. Next, CMV CP was concentrated using Type70 rotor (Beckman, Palo Alto, USA) ultracentrifugation through the 20% sucrose “cushion” under sterile conditions (50 000 rpm, 4 h, +5° C.). The concentration of purified CMVwt was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels.

CMV coat protein can be successfully expressed in *E. coli* cells and significant part obtained can be in soluble fraction. Moreover, these proteins are found directly in *E. coli* cell extracts in the form of isometric VLPs, as demonstrated by sucrose gradient analysis (FIG. 10A), dynamic light scattering and electron-microscopy analysis (FIG. 10B).

Example 6

Cloning of a Modified Coat Protein of CMV Containing an Tetanus Toxoid Epitope (CMV-Ntt830)

To replace the original amino acids at the N-terminus of CMV CP of SEQ ID NO:15 with the tetanus toxoid epitope coding sequence, the pET-CMVwt plasmid was used for PCR amplification and mutagenesis. A SalI site located within the CMVwt gene (FIG. 9) was used for cloning the corresponding PCR products.

To introduce the tetanus toxoid epitope coding sequence into the CMVwt gene, a two step PCR mutagenesis was used. For the first step amplification, the following primers were used: pET-220 (SEQ ID NO:25)—upstream from polylinker, the amplified region includes BglII site) and CMV-tt83-1R (SEQ ID NO:26). For the second round, the PCR product from the first amplification was diluted 1:50 and re-amplified with primers pET-220 (SEQ ID NO:25) and CMV-tt83Sal-R2 (SEQ ID NO:27). The resulting PCR product (cDNA of SEQ ID NO:28 coding for CMV-Ntt830 of SEQ ID NO:20) was subcloned in BglII/SaLI sites of pET-CMVwt. The correct clone was identified by sequencing and designated pET-CMV-Ntt830.

Example 7

Expression of CMV-Ntt830 in *E. coli* Leading to Modified VLPs of CMV

To obtain CMV-Ntt830 VLPs, *E. coli* C2566 cells (New England Biolabs, Ipswich, USA) were transformed with the CMV-Ntt830 gene-containing plasmid pET-CMV-Ntt830. After selection of clones with the highest expression levels of target protein, *E. coli* cultures were grown in 2×TY medium containing kanamycin (25 mg/l) in a rotary shaker (200 rev/min; Infors, Bottmingen, Switzerland) at 30° C. to an OD600 of 0.8-1.0. The cells were then induced with 0.2 mM IPTG, and the medium supplemented with 5 mM $MgCl_2$. Incubation was continued on the rotary shaker at 20° C. for 18 h. The resulting biomass was collected by low-speed centrifugation and frozen at −20° C. After thawing on ice, the cells were suspended in buffer containing 50 mM sodium citrate, 5 mM sodium borate, 5 mM EDTA, 5 mM mercaptoethanol (pH 9.0, buffer A) and disrupted by sonication. Insoluble proteins and cell debris were removed by centrifugation (13,000 rpm, 30 min at 5° C.). The soluble CMV-Ntt830 protein in clarified lysate was pelleted using saturated ammonium sulfate (1:1, vol/vol) overnight at +4° C. Precipitated proteins were solubilized in the buffer A (without mercaptoethanol) for 4 h at +4° C. Insoluble proteins were removed by low speed centrifugation (13,000 rpm, 15 min at 4° C.). Soluble CMV-Ntt830-containing protein solution was separated from cellular proteins by ultracentrifugation (SW28 rotor, Beckman, Palo Alto, USA; at 25,000 rpm, 6 h, 5° C.) in a sucrose gradient (20-60% sucrose in buffer A, without mercaptoethanol, supplemented with 0.5% Triton X-100). The gradient was divided into six fractions, starting at the bottom of the gradient. Fractions containing recombinant CMV-Ntt830 were combined and dialyzed against 200 volumes of 5 mM sodium borate, 2 mM EDTA (pH 9.0) to remove the sucrose and Triton X-100. After dialysis, CMV-Ntt830 solution was sterilized by filtration through a 0.2µ filter. Next, CMV-Ntt830 was concentrated using Type70 rotor (Beckman, Palo Alto, USA) ultracentrifugation through the 20% sucrose "cushion" under sterile conditions (50 000 rpm, 4 h, +5° C.). The concentration of purified CMV-Ntt830 was estimated using the QuBit fluorometer in accordance with manufacturer's recommendations (Invitrogen, Eugene, USA). Concentrated VLP solutions (approx. 3 mg/ml) were stored at +4° C. in 5 mM sodium borate, 2 mM EDTA, buffer (pH 9.0). All steps involved in the expression and purification of VLP were monitored by SDS-PAGE using 12.5% gels.

To demonstrate the presence of the tetanus toxoid epitope in CMV VLPs, mass spectrometric analysis of the purified CMV-Ntt830 VLPs was used. As shown in FIG. 11C, the major peak obtained corresponds to the theoretical molecular mass of the protein if the first methionine is removed which occurs during protein synthesis in *E. coli* cells. Dynamic light scattering and electron microscopy confirmed isometric particle morphology similar to CMVwt VLPs (FIGS. 12A and 12B).

Example 8

Cloning of a Modified Coat Protein of CMV Containing a PADRE Epitope (CMV-Npadr)

To introduce the PADRE epitope coding sequence in CMVwt gene, PCR mutagenesis was carried out using as the template for amplification and subcloning the pET-CMVwt plasmid (see also Example 5 and 6). For the amplification following primers were used: pET-220 (SEQ ID NO:25) and CMV-padrSal-R (SEQ ID NO:29). The resulting PCR product (cDNA of SEQ ID NO:30 coding for CMV-Npadr of SEQ ID NO:21) was again subcloned in BglII/SalI sites of pET-CMVwt. The correct clone was identified by sequencing and designated as pET-CMV-Npadr.

Example 9

Expression of CMV-Npadr in *E. coli* Leading to Modified VLPs of CMV

The procedures for expression and purification of CMV-Npadr were essentially the same as for CMV-Ntt830 and are described in Example 7. To demonstrate the presence of the PADRE epitope in CMV VLPs, the mass spectrometric analysis of the purified CMV-Npadr VLPs was used. As shown in FIG. 11B, the major peak obtained corresponds to the theoretical molecular mass of the protein if the first methionine is removed which occurs during protein synthesis in *E. coli* cells. Dynamic light scattering and electron microscopy analysis confirmed isometric particle morphology, (FIG. 13A and FIG. 13B).

Example 10

Coupling of eIL-5 Antigens to Different VLPs, Immunization of Horses and Demonstration of Efficacy in IBH Prone Horses A. Coupling of eIL5-C-His to VLP of Qβ

Qβ VLP comprising coat proteins of SEQ ID NO:31 were produced as described in WO 02/056905 and reacted with a 10 fold molar excess of the heterobifunctional cross-linker succinimidyl-6(β-maleimidopropionamido)hexanoate (SMPH) (Pierce). Unreacted crosslinker was removed by passage over a PD-10 desalting column (GE Healthcare). The recombinant, purified and refolded eIL-5-C-His was reduced for 1 h with an equimolar excess amount of tri(2-carboxyethyl)phosphine hydrochloride (TCEP) in PBS pH 8.0 to reduce the cysteine residue contained in the linker. The reduced eIL-5-C-His was then mixed with the derivatized Qβ VLPs at a molar ratio of Qβ monomer to eIL-5-C-His protein of 1:2 and co-incubated for 4 hours at 22° C. to allow cross-linking. Optionally, the reaction was dialysed 12 hours against PBS pH 7.4 using a 300 kDa cut-off dialysis membrane or free uncoupled eIL-5-C-His was removed by tangential flow filtration using 100 kDa MWCO.

Analysis: Coomassie staining of SDS-PAGE (FIG. 14A): Qβ, eIL5-C-His and eIL5-C-His-Qβ VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 14B): Qβ, eIL5-C-His and IL5-C-His-Qβ vaccine were separated by SDS-PAGE and electroblotted onto a nitrocellulose membrane. The membrane was blocked for 1 h with 5% (w/v) BSA powder in PBST, then incubated with 10 ml of 1:800 diluted anti-His antibody (Penta-His Antibody, BSA-free, mouse monoclonal IgG1, CatNo. 34660) in 1% BSA (w/v) powder in PBST. The membrane was washed with PBST for 15 minutes and then incubated for 1 h with 10 ml 1% (w/v) BSA in PBST anti-mouse IgG antibody conjugated with horse raddish peroxidase (HRP) at a dilution of 1:10,000. The membrane was washed for 15 minutes in PBS and developed with ECL (Amersham Pharmacia, Sweden) and exposed to Photographic film.

The covalent chemical coupling of eIL5-C-His to the virus-like particle Qβ was assessed by SDS-PAGE and Western blot analyses. Coomassie blue stained gels of the coupling reaction demonstrated the appearance of bands with molecular weights corresponding to those predicted for equine IL5-C-His covalently linked to Qβ (FIG. 14A). Furthermore, Western blot analyses showed co-localization of these bands when stained with anti-His antibody (FIG. 14B).

B. Coupling of eIL5-C-His to CMV-Npadr VLP and to CMV-Ntt830 VLP

CMV-Npadr VLP and CMV-Ntt830 VLP were produced as described above and were reacted with a 10 fold molar excess of the heterobifunctional cross-linker succinimidyl-6(β-maleimidopropionamido)-hexanoate (SMPH) (Pierce). Unreacted crosslinker was removed by passage over a PD-10 desalting column (GE Healthcare). The recombinant, purified and refolded eIL-5-C-His was reduced for 1 h with an equimolar excess amount of tri(2-carboxyethyl)phosphine hydrochloride (TCEP) in PBS pH 8.0 to reduce the cysteine residue contained in the linker. The reduced eIL-5-C-His was then mixed with the derivatized CMV-Npadr or CMV-Ntt830 VLPs at a molar ratio of VLP monomer to eIL-5-C-His protein of 1:2 and co-incubated for 4 hours at 22° C. to allow cross-linking. Optionally, the reaction was dialysed 12 hours against PBS pH 7.4 using a 300 kDa cut-off dialysis membrane or free uncoupled eIL-5-C-His was removed by tangential flow filtration using 100 kDa MWCO.

Analysis: Coomassie staining of SDS-PAGE (FIG. 15A): CMV-Npadr and CMV-Ntt830, eIL5-C-His, eIL5-C-His-CMV-Npadr VLP and eIL5-C-His-CMV-Ntt830 VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 15B): CMV-Npadr and CMV-tt830, eIL5-C-His, eIL5-C-His-CMV-Npadr VLP and eIL5-C-His-CMV-Ntt830 VLP were separated by SDS-PAGE and electroblotted onto a nitrocellulose membrane. The membrane was blocked for 1 h with 5% (w/v) BSA powder in PBST, then incubated with 10 ml of 1:1000 diluted anti-His antibody (monoclonal anti-His Tag antibody HRPO conjugate, Novagen CatNo. 71840) in 1% BSA (w/v) powder in PBST. The membrane was washed with PBST for 15 minutes and then developed with ECL (Amersham Pharmacia, Sweden) and exposed to Photographic film.

The covalent chemical coupling of eIL5-C-His to the CMV-Npadr VLP and CMV-Ntt830 VLP was assessed by SDS-PAGE and Western blot analyses. Coomassie blue stained gels of the coupling reaction demonstrated the appearance of bands with molecular weights corresponding to those predicted for equine IL5-C-His covalently linked to CMV-Npadr and CMV-tt830, respectively (FIG. 15A). Furthermore, Western blot analyses showed co-localization of these bands when stained with anti-His antibody (FIG. 15B).

C. Immunization Protocol

Mice. In order to generate antibodies against equine IL-5 in mice, C57BL/6 or BALB/c mice were injected subcutaneously or intravenously on day 0 and 14 with 25 μg of eIL5-C-His-Qβ VLP in 100 μl of PBS. Mice were bled prior to immunization and at day 21 of the immunisation protocol. Sera were analysed by ELISA.

Horses (eIL-5-C-His-Qβ VLP). In order to generate self-reactive antibodies to equine IL-5, horses were injected subcutaneously on day 0, 21 and day 42 with 300 μg of eIL5-C-His-Qβ VLP in 1,000 μl of PBS mixed 30 min prior to injection with 300 μl alum. When indicated, a booster was given on day 124. Alternatively horses have been injected subcutaneously on day 0, 28, 56, and 84 with 300 μg of eIL5-C-His-Qβ VLP in 1,000 μl of PBS without presence of adjuvants. For follow-up on second year treatment, horses were subcutaneously boosted twice in a four-weekly interval with 300 μg of eIL5-C-His-Qβ VLP in 1,000 μl of PBS without presence of adjuvants. Horses were bled prior to immunization and at least on day 42, day 56 of the immunization protocol and various additional time points post day 56. Sera were analyzed by ELISA. Sera were analyzed by ELISA.

Horses (eIL-5-C-His-CMVtt830). In order to generate self-reactive antibodies to equine IL-5, horses were injected subcutaneously either on day 0, 33, 53 or on day 0, 28, 56 and day 84 with 300 μg or 400 μg of eIL5-C-His-CMVtt830 VLP in 1,000 μl of PBS. Horses were bled prior to immunization and at least either on day 16, 51, 67 or 56, 84 of the immunization protocol and various additional time points post day 84. Sera were analyzed by ELISA. Sera were analyzed by ELISA.

D. Sera Analysis by ELISA

Maxisorp 96 well ELISA plates (Nunc) were coated over night with 50 μl purified eIL-5-C-His, Qβ or purified CMV-Ntt830 (10 μg/ml). Plates were washed 3 times with PBST blocked with 2% BSA in PBS for 2 hours at room temperature. Then plates were washed 3 times with PBST and three-fold dilutions of mouse or horse sera were added in 2% BSA in PBS and incubated at room temperature for 2 h. The plates were subsequently washed 3 times with PBST and incubated with anti-mouse IgG or anti-equine IgG conjugated with HRP (dilution 1:2000) at room temperature for 30 min. The plates were again washed 4 times with PBS and 50 µl/well developing solution (TMB) were added. After approximately 2 minutes of reaction at room temperature the ELISA was stopped with 25 µl per well 5% $H_2SO_4$. Absorbance was measured at 450 nm on a Tecan M200 spectrophotometer (Tecan, Austria).

Figure 16A:
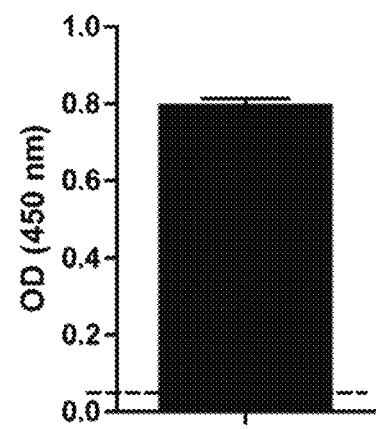
Figure 16B:
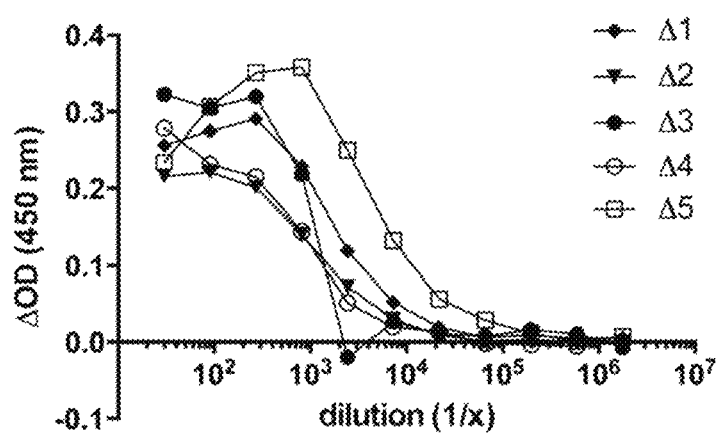
Figure 16C:
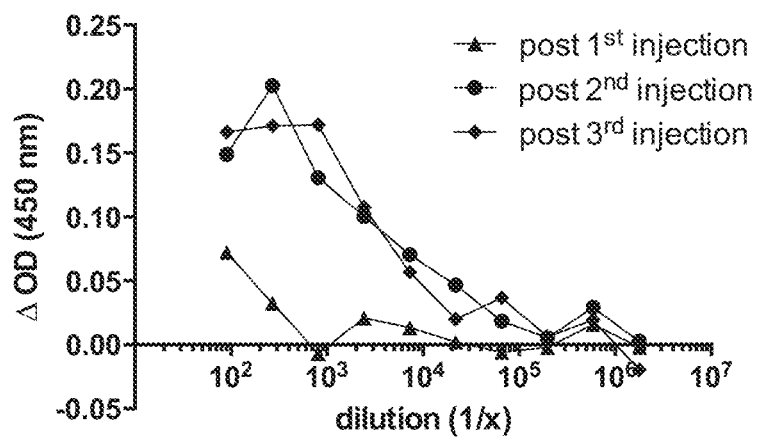
Figure 16D:
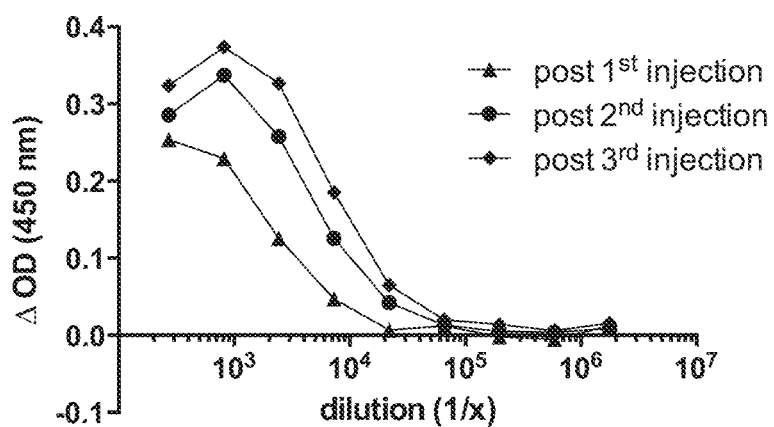
Figure 16E:
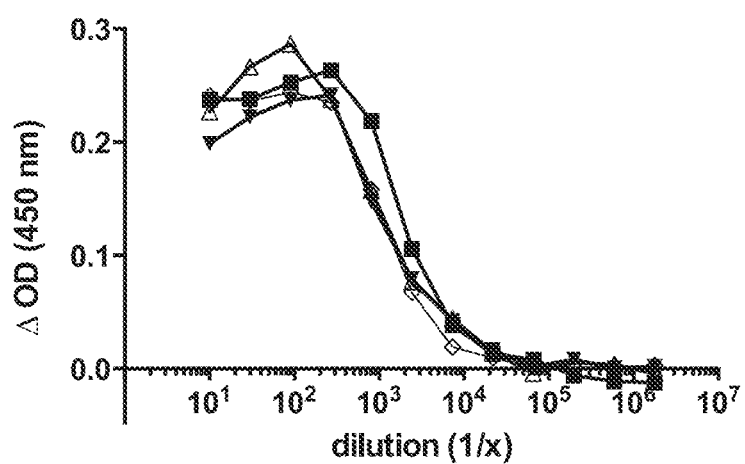

Pre-immune sera and day 21 sera from mice vaccinated with eIL5-C-His-Qβ VLP (FIG. 16A) and pre-immune and day 56 sera from horses vaccinated with eIL5-C-His-Qβ VLP (FIG. 16B) were collected and analyzed by ELISA for antibodies against eIL-5-C-His. Pre-immune and serum after and $3^{rd}$ vaccination of eIL-5-C-His-CMV-Ntt830 of a single horse was collected and sera were analyzed for antibodies against eIL-5-C-His (FIG. 16C) and CMV-Ntt830 (FIG. 16D). In addition, pre-immune sera and day 84 sera from eIL-5-C-His-CMVtt830 VLP vaccinated horses have been analyzed for eIL-5-C-His antibodies (FIG. 16E). All horse sera were blotted as delta OD (ΔOD) values, which were calculated for each dilution by subtracting OD sample serum minus OD naïve serum. The result of vaccination in horses shows that immunological tolerance towards the self-antigen IL-5 was overcome. Half maximal titer at peak of response was in the range between 1:1,000-1:50,000.

E. In Vivo Efficacy

Horses. Correlating eosinophil levels in blood and IBH disease symptoms.

Figure 17A:
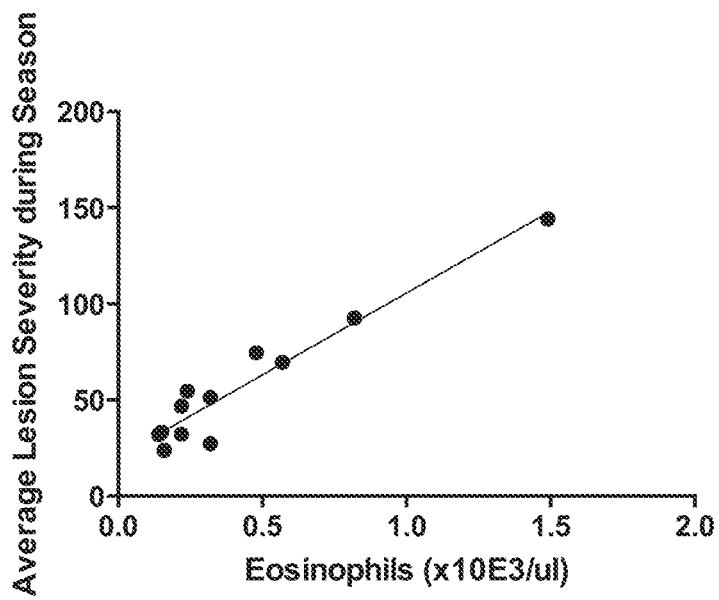
Figure 17B:
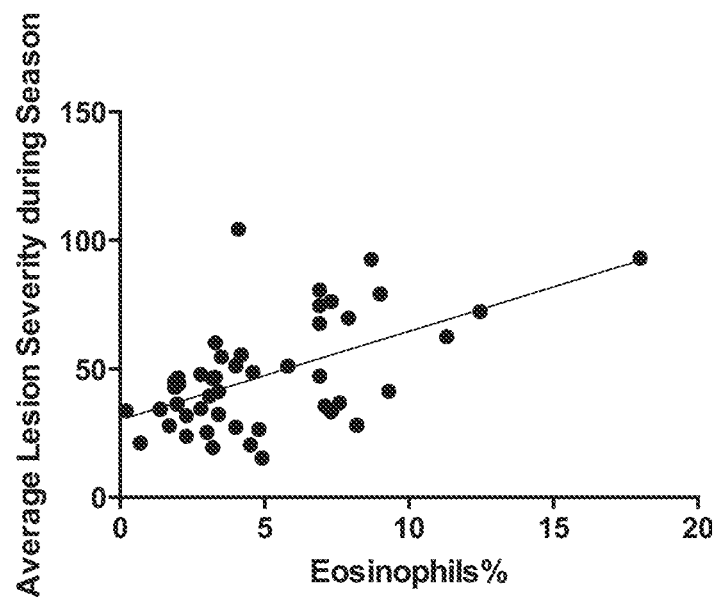

EDTA blood from 12 IBH affected Icelandic horses was taken and eosinophil levels were analyzed. Further disease symptom scoring was assessed during season, i.e. during the months from April to October. Levels of eosinophils in blood were correlated to average disease symptoms measure by lesion symptom scoring. Lesion symptom scoring was done according to Example 13. Indeed a positive correlation between number of eosinophils in blood of sick horses and IBH lesion intensity scores was found ($R^2=0.9227$, $p<0.0001$, $n=12$) (FIG. 17A) showing that the inventive compositions and their use in a method of immunizing horses affected with IBH are beneficial for the treatment of IBH. Additional correlation of blood eosinophils (%) versus average lesion severity during season from 48 IBH affected horses (FIG. 17B) in total ($R2=0.3115$, $p<0.0001$, $n=48$) confirms link between disease severity and percentage eosinophils in the blood.

Case studies: An IBH affected Icelandic horse was vaccinated subcutaneously with eIL-5-C-His-Qβ in order to assess effects of vaccination on disease symptoms and blood eosinophilia. A first horse has been vaccinated subcutaneously for three times using eIL-5-C-His-Qβ. 300 µg of eIL-5-C-His-Qβ in 1 ml PBS was injected per vaccination. The first two injections have been without alum and the third injection was freshly (approx. 30 min before injection) premixed with 0.3 ml alum (Imject Alum, Thermo Scientific, CatNo. 77161). A final volume of 1.3 ml, was injected subcutaneously. The horse was injected on day 4, day 32, and day 59. Directly before and after vaccinations at indicated timepoints, blood were taken and the eosinophil counts in said blood analyzed, in particular antibody titer against eIL-5; moreover, IBH mediated skin lesions were graded by symptoms scoring.

This experiment tested the ability of the anti-eIL5 antibodies generated by vaccination with eIL-5-C-His-Qβ to down-regulate the in vivo action of endogenous eIL-5. Immunization with eIL-5-C-His-Qβ induced anti-equine IL-5 antibody titers in the horse (FIG. 18A). In line with the establishment of an anti-eIL-5 antibody titer, eosinophil levels in blood declined (FIG. 18B). Furthermore, IBH affected lesions started to heal upon antibody titer was established and eosinophil cell numbers declined. The lesion healing was quantified by IBH lesion symptom scoring on tail and mane (FIG. 18C) according to the lesion scoring, Example 13. Hence, disease symptoms of IBH affected lesions disappeared upon vaccination. Without being bound hereby, it is believed that the reduction of eosinophils is evidence that the auto-antibodies generated by immunization with eIL-5-C-His-Qβ presented as a highly ordered immune array recognize the endogenous target molecule and thereby reducing disease symptoms score of an IBH affected horse. Eosinophil levels could be correlated to antibody titer ($R^2=0.8098$) (FIG. 18D), showing that increasing antibody titer correlate to eosinophil decline.

In a further case study, an IBH affected horse is vaccinated subcutaneously with eIL5-C-His-CMV-Ntt830 VLP in order to assess effects of vaccination on disease symptoms and blood eosinophilia. The horse is vaccinated subcutaneously for three times using eIL5-C-His-CMV-Ntt830 VLP. 300 µg of eIL5-C-His-CMV-Ntt830 VLP in 1 ml PBS is injected per vaccination. The first injection was administered in the presence of alum freshly (approx. 30 min before injection) premixed with 0.3 ml alum (Imject Alum, Thermo Scientific, CatNo. 77161), the following two injections have been done without alum. A final volume of 1.3 ml, was injected subcutaneously. The horse was injected on day 0, day 33, and day 53. Directly before and after vaccinations at indicated timepoints, blood was taken and the eosinophil counts in said blood analyzed, in particular antibody titer against eIL-5; moreover, IBH mediated skin lesions were graded by symptoms scoring.

Upon vaccinations with eIL-5-C-His-CMVtt830 the horse established antibody titers against eIL-5 and CMVtt830 (FIG. 18E). Eosinophil levels and lesion severity have been followed over time (FIG. 18F). As soon as the antibody titer against eIL-5 was established, eosinophil levels in blood dropped and with a time delay, lesion severity levels decreased accordingly.

Double-blind placebo controlled randomized study IL-5-C-His-Qβ. Ten IBH affected Icelandic horses were enclosed in a double-blind placebo controlled randomized study in order to assess effects of vaccination on disease symptoms and blood eosinophilia. In the IBH season previous to vaccination (April-October) a bi-weekly symptom scoring was assessed for all horses and blood eosinophilia was quantified beginning of August. Before the following IBH season started, six Icelandic horses were immunized with 300 µg eIL-5-C-His-Qβ and four Icelandic horses received placebo on day 0, 21 and 42 (February/March). The vaccine was administered in 1 ml PBS. All injections were administered in the presence of freshly (approx. 30 min before injection) premixed with 0.3 ml alum (Imject Alum, Thermo Scientific, CatNo. 77161). All horses receive a booster vaccination on day 124 and antibody titers and eosinophil counts were measured monthly from March until October. Furthermore, lesion grading was evaluated bi-weekly. Moreover, health status as well as parasitic status of the horses was analyzed in March and October.

Timeline of antibody titer against Qβ (FIG. 18G) and eIL-5 (FIG. 18H) was followed over the whole season. The horses had been vaccinated by three injections starting in February in a three-week interval followed by a booster immunization approximately two months after the last injection. The established antibody titers against eIL-5 in the active horses varied with a huge magnitude at the beginning, however, were less variable in terms of titer above effectiveness after the boost (FIG. 18H). Most of the titers dropped before the boost and had been practically zero in the middle of the season. Despite the dropping antibody titers in the middle of the season, the vaccinated horses could overall improve their mean lesion severity in the treatment year 2015 (FIG. 18J) when compared to year 2014 before treatment (FIG. 18I). The difference was not statistically significant, but given the low number of horses, the antibody titer drop within season, and that mean lesion severity in pre-evaluation year 2014 was already higher in the active group than in the placebo group, the effect was still remarkable. The mean lesion severity of the placebo horses were either stable or in 2 cases (50%) even worsened in 2015 most likely due to the early, long and warm spring, summer and autumn of 2015. In summary, even with varying antibody titers throughout the season all horses in the vaccine group improved in the treatment year, whereas all horses in the placebo group were stable or even worsened when compared to the previous year (10% difference up or down was determined to be within seasonally variability and was judged as stable) (FIG. 18K and FIG. L). Six out of six treated horses improved; four out of four placebo horses were stable or worsened, leading to a statistically significant therapeutic effect (FIG. 18L).

Follow-up study IL-5-C-His-Qβ. Ten horses from double-blind placebo controlled randomized study using IL-5-C-His-β have been followed-up in the following season 2016. The previously six active horses received two booster immunizations of 300 μg of eIL-5-C-His-Qβ in February and March with a four weeks interval. The previously four placebo horses received active immunization of 300 μg of eIL-5-C-His-Qβ on day 0, 28, 56, and 84. The vaccine for all horses was administered in 1 ml PBS without presence of adjuvants. Antibody titers and eosinophil counts were measured monthly from January and March until June and will be followed up until October. Furthermore, lesion grading was and will be evaluated bi-weekly to monthly. Moreover, health status as well as parasitic status of the horses was and will be analyzed in January and October. Lesion severity was followed from April until June and was compared to lesion severity of fifteen new placebo horses. Lesion severity will be followed up until October.

This study is ongoing, but an interim analysis comparing lesion severity values from April until June (FIG. 18M) from these ten follow-up horses versus fifteen placebo horses from "double-blind placebo controlled randomized study IL-5-His-CMVtt830" shows statistically significant lesion severity in immunized horses when compared to placebo.

Double-blind placebo controlled randomized study IL-5-C-His-CMVtt830. Thirty three IBH affected Icelandic horses were enclosed in a double-blind placebo controlled randomized study in order to assess effects of vaccination on disease symptoms and blood eosinophilia. In the IBH season previous to vaccination (April-October 2015) a monthly symptom scoring was assessed for all horses and blood eosinophilia was quantified at one time point during season. Before the following IBH season started, eighteen Icelandic horses were immunized with 400 μg eIL-5-C-His-CMVtt830 and fifteen Icelandic horses received placebo on day 0, 28, 56 and 84 (January until April). The vaccine was administered in 1 ml PBS without presence of adjuvants. All horses received a booster vaccination on day 126 and antibody titers and eosinophil counts were measured monthly from January and March until June and will be followed up until October. Moreover, health status as well as parasitic status of the horses was and will be analyzed in January and October. Lesion severity was followed from April until June. Lesion severity will be followed up until October.

The study is ongoing, but an interim analysis comparing lesion severity values from April until June from 2015 (FIG. 18N) and 2016 (FIG. 18O) shows reduced lesion severity in the active vaccine group in the treatment year 2016 when comparing to the previous untreated season 2015 and placebo. Delta of lesion severity from April until June 2016 subtracted by lesion severity from April until June 2015 for active vaccine and placebo group, lead to higher positive (improvement) values in the active vaccine group, whereas there was almost no difference in the placebo group (FIG. 18P). Therefore, IL-5-C-His-CMVtt830 vaccine had beneficial effects on lesion severity and thus therapeutically improved disease symptoms.

Example 11

Coupling of eEotaxin Antigen to a VLP, Immunization of Horses and Demonstration of Efficacy in IBH Prone Horses A. Coupling Equine Eotaxin-C-his to VLP of Qβ

Qβ VLP comprising coat proteins of SEQ ID NO:31 were produced as described in WO 02/056905 and reacted with a 2.3 fold molar excess of the heterobifunctional cross-linker succinimidyl-6(β-maleimidopropionamido)hexanoate (SMPH) (Pierce). Unreacted crosslinker was removed by passage over a PD-10 desalting column (GE Healthcare). The recombinant, purified and refolded eEotaxin-C-His was reduced for 1 h with an equimolar excess amount of tri(2-carboxyethyl)phosphine hydrochloride (TCEP) in PBS pH 8.0 to reduce the cysteine residue contained in the linker. The reduced eEotaxin-C-His was then mixed with the derivatized Qβ VLPs at a molar ratio of Qβ monomer to eEotaxin-C-His protein of 2.4:2 and co-incubated for 4 hours at 22° C. to allow cross-linking. Optionally, the reaction was dialysed 12 hours against PBS pH 7.4 using a 300 kDa cut-off dialysis membrane or free uncoupled eIL-5-C-His was removed by tangential flow filtration using 100 kDa MWCO.

Analysis: Coomassie staining of SDS-PAGE (FIG. 19A). Qβ, eEotaxin-C-His and eEotaxin-C-His-Qβ VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 19B). Qβ, eEotaxin-C-His and eEotaxin-C-His-Qβ VLP were separated by SDS-PAGE and electroblotted onto a nitrocellulose membrane. The membrane was blocked for 1 h with 5% (w/v) BSA powder in PBST, then incubated with 10 ml of 1:800 diluted anti-His antibody (Penta-His Antibody, BSA-free, mouse monoclonal IgG1, CatNo. 34660) in 1% BSA (w/v) powder in PBST. The membrane was washed with PBST for 15 minutes and then incubated for 1 h with 10 ml 1% (w/v) BSA in PBST anti-mouse IgG antibody conjugated with horse raddish peroxidase (HRP) at a dilution of 1:10,000. The membrane was washed for 15 minutes in PBS and developed with ECL (Amersham Pharmacia, Sweden) and exposed to Photographic film.

The covalent chemical coupling of eEotaxin-C-His to the virus-like particle Qβ was assessed by SDS-PAGE and Western blot analyses. Coomassie blue stained gels of the coupling reaction demonstrated the appearance of bands with molecular weights corresponding to those predicted for equine Eotaxin-C-His covalently linked to Qβ (FIG. 19A). Furthermore, Western blot analyses showed co-localization of these bands when stained with anti-His antibody (FIG. 19B).

B. Coupling of eEotaxin-C-His to CMV-Ntt830 VLP

CMV-Ntt830 VLP were produced as described above and were reacted with a 2.3 fold molar excess of the heterobifunctional cross-linker succinimidyl-6(β-maleimidopropionamido)-hexanoate (SMPH) (Pierce). Unreacted crosslinker was removed by passage over a PD-10 desalting column (GE Healthcare). The recombinant, purified and refolded eEotaxin-C-His was reduced for 1 h with an equimolar excess amount of tri(2-carboxyethyl)phosphine hydrochloride (TCEP) in PBS pH 8.0 to reduce the cysteine residue contained in the linker. The reduced eEotaxin-C-His was then mixed with the derivatized CMV-Ntt830 VLPs at a molar ratio of VLP monomer to eEotaxin-C-His protein of 2.4:2 and co-incubated for 1 hours at 22° C. to allow cross-linking. Optionally, the reaction was dialysed 12 hours against PBS pH 7.4 using a 300 kDa cut-off dialysis membrane or free uncoupled eIL-5-C-His was removed by tangential flow filtration using 100 kDa MWCO.

Analysis: Coomassie staining of SDS-PAGE: eEotaxin-C-His, CMV-Ntt830, and eEotaxin-C-His-CMV-Ntt830 VLP are separated by SDS-PAGE. Subsequently gel is stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody: eEotaxin-C-His, CMV-Ntt830, and eEotaxin-C-His-CMV-Ntt830 VLP are separated by SDS-PAGE and electroblotted onto a nitrocellulose membrane. The membrane is blocked for 1 h with 5% (w/v) BSA powder in PBST, then incubated with 10 ml of 1:1000 diluted anti-His antibody (monoclonal anti-His Tag antibody HRPO conjugate, Novagen CatNo. 71840) in 1% BSA (w/v) powder in PBST. The membrane is washed with PBST for 15 minutes and then developed with ECL (Amersham Pharmacia, Sweden) and exposed to Photographic film.

B. Immunization Protocol

Mice. In order to generate antibodies against equine Eotaxin in mice, C57BL/6 or BALB/c mice are injected subcutaneously or intravenously on day 0 and 14 with 25 μg of equine Eotaxin-C-His-Qβ vaccine in 100 μl of PBS. Mice are bled prior to immunization and at day 21 of the immunisation protocol. Sera are analysed by ELISA.

Horses. In order to generate self-reactive antibodies to equine IL-5 and equine Eotaxin, horses are injected subcutaneously on day 0, 21 and day 42 with 300 μg of each eIL5-C-His-Qβ/eEotaxin-C-His-Qβ vaccine in 1,000 μl of PBS mixed 30 min prior to injection with 300 μl alum. Horses are bled prior to immunization and at least on day 42, day 56 of the immunization protocol and various additional time points post day 56. Sera are analysed by ELISA.

C. Sera Analysis by ELISA

Maxisorp 96 well ELISA plates (Nunc) are coated over night with 50 μl purified eEotaxin-C-His (10 μg/ml). Plates are washed 3 times with PBST blocked with 2% BSA in PBS for 1.5 hour at room temperature. Then plates are washed 3 times with PBST and three-fold dilutions of mouse or horse sera are added in 2% BSA in PBS and incubated at room temperature for 2 h. The plates are subsequently washed 3 times with PBST and incubated with anti-mouse IgG or anti-equine IgG conjugated with HRP (dilution 1:2000) at room temperature for 30 min. The plates are again washed 4 times with PBS and 50 μl/well developing solution (TMB) are added. After approximately 2 minutes of reaction at room temperature the ELISA is stopped with 25 μl per well 5% $H_2SO_4$. Absorbance is measured at 450 nm on a Tecan M200 spectrophotometer (Tecan).

Preimmune sera and day 21 sera from mice vaccinated with eEotaxin-C-His-Qβ and preimmune and sera from indicated time points from a horse vaccinated with eEotaxin-C-His-Qβ are collected and analyzed by ELISA.

D. In Vivo Efficacy

Horses. Case study. An IBH affected Icelandic horses is vaccinated with a combination vaccine consisting of eIL-5-C-His-Qβ and eEotaxin-C-His-Qβ in order to assess effects of vaccination on disease symptoms and blood eosinophilia. A first horse is vaccinated subcutaneously for three times using eIL-5-C-His-Qβ/eEotaxin-C-His-Qβ combination vaccine. 300 μg of each vaccine in a total volume of 1 ml PBS is injected per vaccination date in alum. Alum is added freshly (approx. 30 min before injection) premixed with 0.3 ml alum (Imject Alum, Thermo Scientific, CatNo. 77161). A final volume of 1.3 ml is injected subcutaneously. The horse is injected on day 0, day 21, and day 42. Before and after vaccinations, eosinophil counts in blood are analyzed and IBH mediated skin lesions are graded by a symptoms score in accordance with the one described in Example 13.

Example 12

Coupling of eIL-31 Antigen to a VLP, Immunization of Horses and Demonstration of Efficacy in IBH Prone Horses A. Coupling Equine IL-31-C-his to VLP of Qβ

Qβ VLP comprising coat proteins of SEQ ID NO:31 were produced as described in WO 02/056905 and reacted with a 7.5 fold molar excess of the heterobifunctional cross-linker succinimidyl-6(β-maleimidopropionamido)hexanoate (SMPH) (Pierce). Unreacted crosslinker was removed by passage over a PD-10 desalting column (GE Healthcare). The recombinant, purified and refolded eIL-31-C-His was reduced for 1 h with an equimolar excess amount of tri(2-carboxyethyl)phosphine hydrochloride (TCEP) in PBS pH 8.0 to reduce the cysteine residue contained in the linker. The reduced eIL-31-C-His was then mixed with the derivatized Qβ VLPs at a molar ratio of Qβ monomer to eIL-31-C-His protein of 1:1 and co-incubated for 4 hours at 22° C. to allow cross-linking. Optionally, the reaction was dialysed 12 hours against PBS pH 7.4 using a 300 kDa cut-off dialysis membrane or free uncoupled eIL-5-C-His was removed by tangential flow filtration using 100 kDa MWCO.

Analysis: Coomassie staining of SDS-PAGE (FIG. 20A). Qβ, eIL-31-C-His and eIL-31-C-His-Qβ VLP were separated by SDS-PAGE. Subsequently gel was stained with Coomassie-Blue (0.025% Coommassie Brilliant BlueR-250, 40% methanol, 10% acetic acid) and de-stained with destainer (40% methanol, 10% acetic acid).

Western blot staining with anti-His antibody (FIG. 20B). Qβ, eIL-31-C-His and eIL-31-C-His-Qβ VLP were separated by SDS-PAGE and electroblotted onto a nitrocellulose membrane. The membrane was blocked for 1 h with 5% (w/v) BSA powder in PBST, then incubated with 10 ml of 1:800 diluted anti-His antibody (Penta-His Antibody, BSA-free, mouse monoclonal IgG1, CatNo. 34660) in 1% BSA (w/v) powder in PBST. The membrane was washed with PBST for 15 minutes and then incubated for 1 h with 10 ml 1% (w/v) BSA in PBST anti-mouse IgG antibody conjugated with horse raddish peroxidase (HRP) at a dilution of 1:10,000. The membrane was washed for 15 minutes in PBS and developed with ECL (Amersham Pharmacia, Sweden) and exposed to Photographic film.

The covalent chemical coupling of eIL-31-C-His to virus-like particle Qβ was assessed by SDS-PAGE and Western blot analyses. Coomassie blue stained gels of the coupling reaction demonstrated the appearance of bands with molecular weights corresponding to those predicted for equine IL-31-C-His covalently linked to Qβ (FIG. 20A). Furthermore, Western blot analyses showed co-localization of these bands when stained with anti-His antibody (FIG. 20B).

B. Coupling of eIL31-C-His to CMV-Ntt830 VLP

CMV-Ntt830 VLP were produced as described above and were reacted with a 10 fold molar excess of the heterobifunctional cross-linker succinimidyl-6(β-maleimidopropionamido)-hexanoate (SMPH) (Pierce). Unreacted crosslinker was removed by passage over a PD-10 desalting column (GE Healthcare). The recombinant, purified and refolded eIL-31-C-His was reduced for 1 h with an equimolar excess amount of tri(2-carboxyethyl)phosphine hydrochloride (TCEP) in PBS pH 8.0 to reduce the cysteine residue contained in the linker. The reduced eIL-31-C-His was then mixed with the derivatized CMV-Ntt830 VLPs at a molar ratio of VLP monomer to eIL-31-C-His protein of 1:2 and co-incubated for 4 hours at 22° C. to allow cross-linking. Optionally, the reaction was dialysed 12 hours against PBS pH 7.4 using a 300 kDa cut-off dialysis membrane or free uncoupled eIL-5-C-His was removed by tangential flow filtration using 100 kDa MWCO.

Analysis: Coomassie staining of SDS-PAGE (FIG. 20C): eIL-31-C-His, CMV-Ntt830, and eIL31-C-His-CMV-Ntt830 VLP were separated by SDS-PAGE. Subsequently gel was stained with Coomassie-Blue (0.025% Coomassie Brilliant BlueR-250, 40% methanol, 10% acetic acid) and de-stained with destainer (40% methanol, 10% acetic acid).

Western blot staining with anti-His antibody (FIG. 20D): eIL-31-C-His, CMV-Ntt830, and eIL31-C-His-CMV-Ntt830 VLP were separated by SDS-PAGE and electroblotted onto a nitrocellulose membrane. The membrane was blocked for 1 h with 5% (w/v) BSA powder in PBST, then incubated with 10 ml of 1:1000 diluted anti-His antibody (monoclonal anti-His Tag antibody HRPO conjugate, Novagen CatNo. 71840) in 1% BSA (w/v) powder in PBST. The membrane was washed with PBST for 15 minutes and then developed with ECL (Amersham Pharmacia, Sweden) and exposed to Photographic film.

The covalent chemical coupling of eIL5-C-His to CMV-Ntt830 VLP was assessed by SDS-PAGE and Western blot analyses. Coomassie blue stained gels of the coupling reaction demonstrated the appearance of bands with molecular weights corresponding to those predicted for equine IL31-C-His covalently linked to CMV-tt830, respectively (FIG. 20C). Furthermore, Western blot analyses showed co-localization of these bands when stained with anti-His antibody (FIG. 20D).

B. Immunization Protocol

Mice. In order to generate antibodies against equine IL-31 in mice, C57BL/6 or BALB/c mice are injected subcutaneously or intravenously on day 0 and 14 with 25 μg of equine IL-31-C-His-Qβ vaccine in 100 μl of PBS. Mice are bled prior to immunization and at day 21 of the immunisation protocol. Sera are analysed by ELISA.

Horses. In order to generate self-reactive antibodies to equine IL-5 and equine IL-31, horses are injected subcutaneously on day 0, 21 and day 42 with 300 μg of each eIL5-C-His-Qβ/eIL-31-C-His-Qβ vaccine in 1,000 μl of PBS mixed 30 min prior to injection with 300 μl alum. Horses are bled prior to immunization and at least on day 42, day 56 of the immunization protocol and various additional time points post day 56. Sera are analysed by ELISA.

C. Sera Analysis by ELISA:

Maxisorp 96 well ELISA plates (Nunc) were coated over night with 50 μl purified eIL-31-C-His (10 μg/ml). Plates were washed 3 times with PBST blocked with 2% BSA in PBS for 1.5 hour at room temperature. Then plates were washed 3 times with PBST and three-fold dilutions of mouse or horse sera were added in 2% BSA in PBS and incubated at room temperature for 2 h. The plates were subsequently washed 3 times with PBST and incubated with anti-mouse IgG or anti-equine IgG conjugated with HRP (dilution 1:2000) at room temperature for 30 min. The plates were again washed 4 times with PBS and 50 μl/well developing solution (TMB) were added. After approximately 2 minutes of reaction at room temperature the ELISA was stopped with 25 μl per well 5% $H_2SO_4$. Absorbance was measured at 450 nm on a Tecan M200 spectrophotometer (Tecan, Austria).

Preimmune sera and day 21 sera from mice vaccinated with eIL-31-C-His-Qβ and preimmune and sera from indicated time points from a horse vaccinated with eIL-31-C-His-Qβ are collected and analyzed by ELISA.

D. In vivo Efficacy: Case study. An IBH affected Icelandic horse is vaccinated with a combination vaccine consisting of eIL-5-C-His-Qβ and eIL-31-C-His-Qβ in order to assess effects of vaccination on disease symptoms and blood eosinophilia.

A first horse is vaccinated subcutaneously for three times using eIL-5-C-His-Qβ/eIL-31-C-His-Qβ combination vaccine. 300 μg of each vaccine in a total volume of 1 ml PBS is injected per vaccination date in alum. Alum is added freshly (approx. 30 min before injection) premixed with 0.3 ml alum (Imject Alum, Thermo Scientific, CatNo. 77161). A final volume of 1.3 ml, is injected subcutaneously. The horse is injected on day 0, day 21, and day 42. Before and after vaccinations, eosinophil counts in blood are analyzed and IBH mediated skin lesions are graded by a symptoms scoring described in Example 13.

Example 13

IBH Symptom Lesion Scoring

For IBH symptom scoring, the location (tail, mane, belly, flank, face, ear, leg, and the like) where IBH lesions occur are recorded. Each location is divided into 3 parts: up, middle, down. Further according to the number of lesions, each location is classified into light and strong. Dependent on how many parts are affected (up/middle/down) and how many lesions per location are found (light/strong), 1 to 4 points can be scored (1 point=one part affected, lesion light; 4 points=all three parts affected, lesion strong).

Moreover, these locations are classified for 6 further properties: size (diameter), blood, hair loss, scales, crust, and lichenification/swelling. For all these properties also 1 to 4 points can be scored. Size is divided into <0.5 cm (1 point), 0.5≥x>1 cm (2 points), 1≥x>2 cm (3 points), and ≥2 cm (4 points). Blood is divided into intact epidermis (1 point), mild (2 points), moderate (3 points), and severe (4 points). Hair loss is divided into mild (1 point), moderate (2 points), severe (3 points), and no hair (4 points). Scales is divided into none (1 point), tiny, few (2 points), moderate, mid-size (3 points), and many, big (4 points). Crust is divided into none (1 point), tiny (2 points), half (3 points), and total (4 points). Lichenification and/or swelling is divided into none (1 point), mild (2 points), moderate (3 points), and severe (4 points).

Additionally, if sheath or udder is swollen, minimally 5 or maximally 20 points can be scored: grade 1 (5 points), grade 2 (10 points), grade 3 (15 points), and grade 4 (20 points).

Finally all points are added up and are the IBH symptom score.

The invention claimed is:

1. A composition comprising:
   (a) a core particle with at least one first attachment site; and
   (b) at least one antigen with at least one second attachment site, wherein said at least one antigen is an equine Interleukin-5 antigen (eIL-5 antigen), wherein said eIL-5 antigen comprises a protein with an amino acid sequence of at least 92% amino acid sequence identity with SEQ ID NO:1;
   wherein (a) and (b) are linked through said at least one first and said at least one second attachment site via at least one non-peptide covalent bond.

2. The composition of claim 1, wherein said protein with an amino acid sequence of at least 92% amino acid sequence identity with SEQ ID NO:1 is selected from SEQ ID NO:2, SEQ ID NO:5, SEQ ID NO:35, SEQ ID NO:36, SEQ ID NO:37 and SEQ ID NO:38.

3. The composition of claim 1, wherein said core particle is a virus-like particle (VLP).

4. The composition of claim 3, wherein said VLP is derived from a plant virus or is a VLP of an RNA bacteriophage.

5. The composition of claim 3, wherein said VLP is a VLP of RNA bacteriophage Qβ, wherein said VLP of RNA bacteriophage Qβ comprises recombinant coat proteins, wherein each coat protein SEQ ID NO:31.

6. The composition of claim 3, wherein said VLP is a modified VLP comprising at least one modified VLP polypeptide, wherein said modified VLP polypeptide comprises
   (a) a VLP polypeptide, and
   (b) a T helper cell epitope,
   wherein said VLP polypeptide comprises
   (i) an amino acid sequence of a coat protein of a virus; or
   (ii) a mutated amino acid sequence, wherein said mutated amino acid sequence has a sequence identity of at least 90% to said coat protein of a virus.

7. The composition of claim 3, wherein said VLP is a modified VLP of cucumber mosaic virus (CMV), wherein said modified VLP of CMV comprises at least one modified CMV polypeptide, wherein said modified CMV polypeptide comprises
   (a) a CMV polypeptide, and
   (b) a T helper cell epitope; and
   wherein said CMV polypeptide comprises
   (ii) an amino acid sequence of a coat protein of CMV; or
   (ii) a mutated amino acid sequence, wherein said mutated amino acid sequence has a sequence identity of at least 90% to said coat protein of CMV.

8. The composition of claim 7, wherein said T helper cell epitope replaces a N-terminal region of said CMV polypeptide, and wherein said N-terminal region of said CMV polypeptide is amino acids 2-12 of SEQ ID NO:15.

9. The composition of claim 7, wherein said CMV polypeptide comprises an amino acid sequence of a coat protein of CMV, wherein said amino acid sequence comprises SEQ ID NO:15 or an amino acid sequence having a sequence identity of at least 95% with SEQ ID NO:15; and wherein said CMV polypeptide comprises an amino acid sequence comprising SEQ ID NO:34, and wherein said T helper cell epitope replaces the N-terminal region of said CMV polypeptide, and wherein said replaced N-terminal region of said CMV polypeptide consists of 11 to 13 consecutive amino acids.

10. The composition of claim 7, wherein said modified CMV polypeptide comprises an amino acid sequence of SEQ ID NO:20 or SEQ ID NO:21.

11. A pharmaceutical composition comprising:
    (a) the composition of claim 1; and
    (b) a pharmaceutically acceptable carrier.

12. The composition of claim 3, wherein said core particle is a recombinant virus-like particle (VLP).

13. The composition of claim 6, wherein said VLP polypeptide comprises an amino acid sequence of a coat protein of a plant virus.

14. The composition of claim 9, wherein said replaced N-terminal region of said CMV polypeptide consists of 11 consecutive amino acids.

15. The composition of claim 14, wherein said N-terminal region of said CMV polypeptide is amino acids 2-12 of SEQ ID NO:15.

16. The composition of claim 1, wherein said eIL-5 antigen comprises a protein with an amino acid sequence of at least 95% amino acid sequence identity with SEQ ID NO:1.

17. The composition of claim 1, wherein said eIL-5 antigen comprises a protein with an amino acid sequence of at least 98% amino acid sequence identity with SEQ ID NO:1.

18. The composition of claim 1, wherein said protein with an amino acid sequence of at least 92% amino acid sequence identity with SEQ ID NO:1 is selected from SEQ ID NO:2, SEQ ID NO:5 and SEQ ID NO:36.

19. The composition of claim 1, wherein said eIL-5 antigen comprises a protein with the amino acid sequence SEQ ID NO:2.

20. The composition of claim 1, wherein said eIL-5 antigen consists of a protein with the amino acid sequence SEQ ID NO:2.

21. The composition of claim 7, wherein said modified CMV polypeptide comprises the amino acid sequence of SEQ ID NO:20.

22. The composition of claim 19, wherein said core particle is a modified VLP of cucumber mosaic virus (CMV) comprising modified CMV polypeptides, wherein each of said modified CMV polypeptides comprises the amino acid sequence of SEQ ID NO:20.

23. The composition of claim 20, wherein said core particle is a modified VLP of cucumber mosaic virus (CMV) comprising modified CMV polypeptides, wherein each of said modified CMV polypeptides comprises the amino acid sequence of SEQ ID NO:20.

24. The composition of claim 1, wherein said core particle is a modified VLP of cucumber mosaic virus (CMV) comprising modified CMV polypeptides, wherein each of said modified CMV polypeptides comprises the amino acid sequence of SEQ ID NO:20.

* * * * *

SEQUENCE LISTING

<160> NUMBER OF SEQ ID NOS: 46

<210> SEQ ID NO 1
<211> LENGTH: 114
<212> TYPE: PRT
<213> ORGANISM: artificial sequence
<220> FEATURE:
<223> OTHER INFORMATION: eIL-5 mature protein fragment

<400> SEQUENCE: 1

Ala Val Glu Ser Pro Met Asn Arg Leu Val Ala Glu Thr Leu Thr Leu
1               5                   10                  15

Leu Ser Thr His Arg Thr Leu Leu Ile Gly Asp Gly Asn Leu Met Ile
                20                  25                  30

Pro Thr Pro Glu His Lys Asn His Gln Leu Cys Ile Glu Glu Val Phe
            35                  40                  45

Gln Gly Ile Asp Thr Leu Lys Asn Gln Thr Val Gln Gly Asp Ala Val
        50                  55                  60

Ala Lys Leu Phe Gln Asn Leu Ser Leu Ile Lys Gly Tyr Ile Asp Leu
65                  70                  75                  80

Gln Lys Lys Lys Cys Gly Gly Glu Arg Trp Arg Val Lys Gln Phe Leu
                85                  90                  95

Asp Tyr Leu Gln Glu Phe Leu Gly Val Ile Asn Thr Glu Trp Thr Ile
            100                 105                 110

Glu Gly

<210> SEQ ID NO 2
<211> LENGTH: 115
<212> TYPE: PRT
<213> ORGANISM: artificial sequence
<220> FEATURE:
<223> OTHER INFORMATION: eIL-5 mature protein fragment

<400> SEQUENCE: 2

Leu Ala Val Glu Ser Pro Met Asn Arg Leu Val Ala Glu Thr Leu Thr
1               5                   10                  15

Leu Leu Ser Thr His Arg Thr Leu Leu Ile Gly Asp Gly Asn Leu Met
                20                  25                  30

Ile Pro Thr Pro Glu His Lys Asn His Gln Leu Cys Ile Glu Glu Val
            35                  40                  45

Phe Gln Gly Ile Asp Thr Leu Lys Asn Gln Thr Val Gln Gly Asp Ala
        50                  55                  60

Val Ala Lys Leu Phe Gln Asn Leu Ser Leu Ile Lys Gly Tyr Ile Asp
65                  70                  75                  80

Leu Gln Lys Lys Lys Cys Gly Gly Glu Arg Trp Arg Val Lys Gln Phe
                85                  90                  95

Leu Asp Tyr Leu Gln Glu Phe Leu Gly Val Ile Asn Thr Glu Trp Thr
            100                 105                 110

Ile Glu Gly
        115

<210> SEQ ID NO 3
<211> LENGTH: 134
<212> TYPE: PRT
<213> ORGANISM: Equus caballus

<400> SEQUENCE: 3

Met Arg Met Leu Leu His Leu Ser Val Leu Ala Leu Gly Ala Ala Tyr
1               5                   10                  15

Val Cys Ala Leu Ala Val Glu Ser Pro Met Asn Arg Leu Val Ala Glu
            20                  25                  30

Thr Leu Thr Leu Leu Ser Thr His Arg Thr Leu Leu Ile Gly Asp Gly
        35                  40                  45

Asn Leu Met Ile Pro Thr Pro Glu His Lys Asn His Gln Leu Cys Ile
 50                  55                  60

Glu Glu Val Phe Gln Gly Ile Asp Thr Leu Lys Asn Gln Thr Val Gln
65                  70                  75                  80

Gly Asp Ala Val Ala Lys Leu Phe Gln Asn Leu Ser Leu Ile Lys Gly
                85                  90                  95

Tyr Ile Asp Leu Gln Lys Lys Cys Gly Gly Glu Arg Trp Arg Val
            100                 105                 110

Lys Gln Phe Leu Asp Tyr Leu Gln Glu Phe Leu Gly Val Ile Asn Thr
        115                 120                 125

Glu Trp Thr Ile Glu Gly
    130

<210> SEQ ID NO 4
<211> LENGTH: 390
<212> TYPE: DNA
<213> ORGANISM: artificial sequence
<220> FEATURE:
<223> OTHER INFORMATION: pET42b-eIL-5

<400> SEQUENCE: 4
catatggcag ttgaaagccc gatgaatcgt ctggttgcag aaaccctgac cctgctgagc      60
acccatcgta cactgctgat tggtgatggt aatctgatga ttccgacacc ggaacataaa     120
aatcatcagc tgtgtatcga agaagtgttt cagggcattg ataccctgaa aaatcagacc     180
gttcagggtg atgcagttgc aaaactgttt cagaatctga gcctgatcaa aggctatatc     240
gatctgcaga aaaaaaaatg cggtggtgaa cgttggcgtg ttaaacagtt tctggattat     300
ctgcaagaat ttctgggcgt gattaatacc gaatggacca ttgaaggtgg tggttgtctc     360
gagcaccacc accaccacca ccaccactaa                                      390

<210> SEQ ID NO 5
<211> LENGTH: 127
<212> TYPE: PRT
<213> ORGANISM: artificial sequence
<220> FEATURE:
<223> OTHER INFORMATION: eIL-5-C-His

<400> SEQUENCE: 5

Ala Val Glu Ser Pro Met Asn Arg Leu Val Ala Glu Thr Leu Thr Leu
1               5                   10                  15

Leu Ser Thr His Arg Thr Leu Leu Ile Gly Asp Gly Asn Leu Met Ile
            20                  25                  30

Pro Thr Pro Glu His Lys Asn His Gln Leu Cys Ile Glu Glu Val Phe
        35                  40                  45

Gln Gly Ile Asp Thr Leu Lys Asn Gln Thr Val Gln Gly Asp Ala Val
 50                  55                  60

Ala Lys Leu Phe Gln Asn Leu Ser Leu Ile Lys Gly Tyr Ile Asp Leu
65                  70                  75                  80

Gln Lys Lys Cys Gly Gly Glu Arg Trp Arg Val Lys Gln Phe Leu
                85                  90                  95

Asp Tyr Leu Gln Glu Phe Leu Gly Val Ile Asn Thr Glu Trp Thr Ile
        100                 105                 110

```
Glu Gly Gly Gly Cys Leu Glu His His His His His His His His
        115                 120                 125

<210> SEQ ID NO 6
<211> LENGTH: 76
<212> TYPE: PRT
<213> ORGANISM: artificial sequence
<220> FEATURE:
<223> OTHER INFORMATION: eEotaxin mature fragment

<400> SEQUENCE: 6

Pro Val Ser Ile Ser Thr Val Cys Cys Phe Asn Val Ala Ser Arg Lys
1               5                   10                  15

Ile Ser Phe Gln Arg Leu Gln Ser Tyr Arg Lys Ile Thr Ser Ser Lys
            20                  25                  30

Cys Pro Gln Lys Ala Val Ile Phe Lys Thr Lys Gln Ala Lys Lys Ile
        35                  40                  45

Cys Ala Asp Pro Lys Gln Lys Trp Val Gln Asp Ala Met Lys Tyr Leu
    50                  55                  60

Asp Glu Asn Ser Arg Thr Thr Lys Tyr Ser Ser Phe
65                  70                  75

<210> SEQ ID NO 7
<211> LENGTH: 77
<212> TYPE: PRT
<213> ORGANISM: artificial sequence
<220> FEATURE:
<223> OTHER INFORMATION: eEotaxin mature fragment

<400> SEQUENCE: 7

Gln Pro Val Ser Ile Ser Thr Val Cys Cys Phe Asn Val Ala Ser Arg
1               5                   10                  15

Lys Ile Ser Phe Gln Arg Leu Gln Ser Tyr Arg Lys Ile Thr Ser Ser
            20                  25                  30

Lys Cys Pro Gln Lys Ala Val Ile Phe Lys Thr Lys Gln Ala Lys Lys
        35                  40                  45

Ile Cys Ala Asp Pro Lys Gln Lys Trp Val Gln Asp Ala Met Lys Tyr
    50                  55                  60

Leu Asp Glu Asn Ser Arg Thr Thr Lys Tyr Ser Ser Phe
65                  70                  75

<210> SEQ ID NO 8
<211> LENGTH: 100
<212> TYPE: PRT
<213> ORGANISM: Equus caballus

<400> SEQUENCE: 8

Met Lys Val Ser Ala Ala Leu Leu Cys Leu Leu Leu Thr Thr Ala Ala
1               5                   10                  15

Phe Ser Thr Gln Val Leu Ala Gln Pro Val Ser Ile Ser Thr Val Cys
            20                  25                  30

Cys Phe Asn Val Ala Ser Arg Lys Ile Ser Phe Gln Arg Leu Gln Ser
        35                  40                  45

Tyr Arg Lys Ile Thr Ser Ser Lys Cys Pro Gln Lys Ala Val Ile Phe
    50                  55                  60

Lys Thr Lys Gln Ala Lys Lys Ile Cys Ala Asp Pro Lys Gln Lys Trp
65                  70                  75                  80

Val Gln Asp Ala Met Lys Tyr Leu Asp Glu Asn Ser Arg Thr Thr Lys
                85                  90                  95
```

Tyr Ser Ser Phe
            100

<210> SEQ ID NO 9
<211> LENGTH: 279
<212> TYPE: DNA
<213> ORGANISM: artificial sequence
<220> FEATURE:
<223> OTHER INFORMATION: pET42b-eEotaxin

<400> SEQUENCE: 9
catatgccgg ttagcattag caccgtttgt tgttttaatg ttgccagccg caaaattagc    60
tttcagcgtc tgcagagcta tcgtaaaatt accagcagca aatgtccgca gaaagccgtt   120
atctttaaaa ccaaacaggc caaaaaaatc tgtgccgatc cgaaacagaa atgggttcag   180
gatgcaatga aatatctgga tgaaaatagc cgcaccacca aatatagcag ctttggtggc   240
ggttgtctcg agcaccacca ccaccaccac caccactaa                          279

<210> SEQ ID NO 10
<211> LENGTH: 89
<212> TYPE: PRT
<213> ORGANISM: artificial sequence
<220> FEATURE:
<223> OTHER INFORMATION: eEotaxin-C-His

<400> SEQUENCE: 10

Pro Val Ser Ile Ser Thr Val Cys Cys Phe Asn Val Ala Ser Arg Lys
1               5                   10                  15

Ile Ser Phe Gln Arg Leu Gln Ser Tyr Arg Lys Ile Thr Ser Ser Lys
            20                  25                  30

Cys Pro Gln Lys Ala Val Ile Phe Lys Thr Lys Gln Ala Lys Lys Ile
        35                  40                  45

Cys Ala Asp Pro Lys Gln Lys Trp Val Gln Asp Ala Met Lys Tyr Leu
    50                  55                  60

Asp Glu Asn Ser Arg Thr Thr Lys Tyr Ser Ser Phe Gly Gly Cys Leu
65                  70                  75                  80

Glu His His His His His His His His
            85

<210> SEQ ID NO 11
<211> LENGTH: 149
<212> TYPE: PRT
<213> ORGANISM: Equus caballus

<400> SEQUENCE: 11

Met Val Ser His Ile Gly Thr Thr Ala Phe Ala Leu Phe Leu Leu Cys
1               5                   10                  15

Cys Leu Gly Thr Leu Met Phe Ser His Thr Gly Pro Ile Tyr Gln Leu
            20                  25                  30

Gln Pro Lys Glu Ile Gln Ala Ile Ile Val Glu Leu Gln Asn Leu Ser
        35                  40                  45

Lys Lys Leu Leu Asp Asp Tyr Leu Asn Lys Leu Lys Gly Val Gln Lys
    50                  55                  60

Phe Asp Ser Asp Leu Pro Ser Cys Phe Thr Ser Asp Ser Gln Ala Pro
65                  70                  75                  80

Gly Asn Ile Asn Ser Ser Ala Ile Leu Pro Tyr Phe Lys Ala Ile Ser
            85                  90                  95

Pro Ser Leu Asn Asn Asp Lys Ser Leu Tyr Ile Ile Glu Gln Leu Asp

Lys Leu Asn Phe Gln Asn Ala Pro Glu Thr Glu Val Ser Met Pro Thr
            100                 105                 110
        115                 120                 125

Asp Asn Phe Glu Arg Lys Arg Phe Ile Leu Thr Ile Leu Arg Trp Phe
        130                 135                 140

Ser Asn Cys Leu Glu
145

<210> SEQ ID NO 12
<211> LENGTH: 123
<212> TYPE: PRT
<213> ORGANISM: artificial sequence
<220> FEATURE:
<223> OTHER INFORMATION: eIL-31 mature fragment

<400> SEQUENCE: 12

Gly Pro Ile Tyr Gln Leu Gln Pro Lys Glu Ile Gln Ala Ile Ile Val
1               5                   10                  15

Glu Leu Gln Asn Leu Ser Lys Lys Leu Leu Asp Asp Tyr Leu Asn Lys
            20                  25                  30

Glu Lys Gly Val Gln Lys Phe Asp Ser Asp Leu Pro Ser Cys Phe Thr
        35                  40                  45

Ser Asp Ser Gln Ala Pro Gly Asn Ile Asn Ser Ala Ile Leu Pro
    50                  55                  60

Tyr Phe Lys Ala Ile Ser Pro Ser Leu Asn Asn Asp Lys Ser Leu Tyr
65                  70                  75                  80

Ile Ile Glu Gln Leu Asp Lys Leu Asn Phe Gln Asn Ala Pro Glu Thr
                85                  90                  95

Glu Val Ser Met Pro Thr Asp Asn Phe Glu Arg Lys Arg Phe Ile Leu
            100                 105                 110

Thr Ile Leu Arg Trp Phe Ser Asn Cys Leu Glu
        115                 120

<210> SEQ ID NO 13
<211> LENGTH: 420
<212> TYPE: DNA
<213> ORGANISM: artificial sequence
<220> FEATURE:
<223> OTHER INFORMATION: pET42b-eIL-31

<400> SEQUENCE: 13
catatgggtc cgatttatca gctgcagccg aaagaaattc aggccattat tgttgaactg      60
cagaacctga gcaaaaaact gctggatgat tacctgaaca agaaaaaggg cgtgcagaaa     120
tttgatagcg atctgccgag ctgttttacc agcgatagcc aggcaccggg taacattaat     180
agcagcgcaa ttctgccgta tttcaaagca attagcccga gcctgaataa tgataaaagc     240
ctgtatatta tcgaacagct ggataaactg aactttcaga atgcaccgga aaccgaagtt     300
agcatgccga ccgataattt tgaacgcaaa cgttttattc tgaccatcct gcgttggttt     360
agcaattgtc tggaaggtgg tggttgtctc gagcaccacc accaccacca ccactaa       420

<210> SEQ ID NO 14
<211> LENGTH: 136
<212> TYPE: PRT
<213> ORGANISM: artificial sequence
<220> FEATURE:
<223> OTHER INFORMATION: eIL-31-C-His

<400> SEQUENCE: 14

```
Gly Pro Ile Tyr Gln Leu Gln Pro Lys Glu Ile Gln Ala Ile Ile Val
1               5                   10                  15

Glu Leu Gln Asn Leu Ser Lys Lys Leu Leu Asp Asp Tyr Leu Asn Lys
            20                  25                  30

Glu Lys Gly Val Gln Lys Phe Asp Ser Asp Leu Pro Ser Cys Phe Thr
        35                  40                  45

Ser Asp Ser Gln Ala Pro Gly Asn Ile Asn Ser Ser Ala Ile Leu Pro
    50                  55                  60

Tyr Phe Lys Ala Ile Ser Pro Ser Leu Asn Asn Asp Lys Ser Leu Tyr
65                  70                  75                  80

Ile Ile Glu Gln Leu Asp Lys Leu Asn Phe Gln Asn Ala Pro Glu Thr
                85                  90                  95

Glu Val Ser Met Pro Thr Asp Asn Phe Glu Arg Lys Arg Phe Ile Leu
            100                 105                 110

Thr Ile Leu Arg Trp Phe Ser Asn Cys Leu Glu Gly Cys Leu Glu
        115                 120                 125

His His His His His His His
    130                 135

<210> SEQ ID NO 15
<211> LENGTH: 218
<212> TYPE: PRT
<213> ORGANISM: cucumber mosaic virus

<400> SEQUENCE: 15

Met Asp Lys Ser Glu Ser Thr Ser Ala Gly Arg Ser Arg Arg Arg
1               5                   10                  15

Pro Arg Arg Gly Ser Arg Ser Ala Pro Ser Ser Ala Asp Ala Asn Phe
            20                  25                  30

Arg Val Leu Ser Gln Gln Leu Ser Arg Leu Asn Lys Thr Leu Ala Ala
        35                  40                  45

Gly Arg Pro Thr Ile Asn His Pro Thr Phe Val Gly Ser Glu Arg Cys
    50                  55                  60

Lys Pro Gly Tyr Thr Phe Thr Ser Ile Thr Leu Lys Pro Pro Lys Ile
65                  70                  75                  80

Asp Arg Gly Ser Tyr Tyr Gly Lys Arg Leu Leu Leu Pro Asp Ser Val
                85                  90                  95

Thr Glu Tyr Asp Lys Lys Leu Val Ser Arg Ile Gln Ile Arg Val Asn
            100                 105                 110

Pro Leu Pro Lys Phe Asp Ser Thr Val Trp Val Thr Val Arg Lys Val
        115                 120                 125

Pro Ala Ser Ser Asp Leu Ser Val Ala Ala Ile Ser Ala Met Phe Ala
    130                 135                 140

Asp Gly Ala Ser Pro Val Leu Val Tyr Gln Tyr Ala Ala Ser Gly Val
145                 150                 155                 160

Gln Ala Asn Asn Lys Leu Leu Tyr Asp Leu Ser Ala Met Arg Ala Asp
                165                 170                 175

Ile Gly Asp Met Arg Lys Tyr Ala Val Leu Val Tyr Ser Lys Asp Asp
            180                 185                 190

Ala Leu Glu Thr Asp Glu Leu Val Leu His Val Asp Val Glu His Gln
        195                 200                 205

Arg Ile Pro Thr Ser Gly Val Leu Pro Val
    210                 215

<210> SEQ ID NO 16
```

```
<211> LENGTH: 217
<212> TYPE: PRT
<213> ORGANISM: cucumber mosaic virus

<400> SEQUENCE: 16

Asp Lys Ser Glu Ser Thr Ser Ala Gly Arg Asn Arg Arg Arg Pro
1               5                   10                  15

Arg Arg Gly Ser Arg Ser Ala Ser Ser Ala Asp Ala Asn Phe Arg
            20                  25                  30

Val Leu Ser Gln Gln Leu Ser Arg Leu Asn Lys Thr Leu Ala Ala Gly
            35                  40                  45

Arg Pro Thr Ile Asn His Pro Thr Phe Val Gly Ser Glu Arg Cys Lys
50                  55                  60

Pro Gly Tyr Thr Phe Ser Ser Ile Thr Leu Lys Pro Pro Lys Ile Asp
65                  70                  75                  80

Arg Gly Ser Tyr Tyr Gly Lys Arg Leu Leu Leu Pro Asp Ser Val Thr
                85                  90                  95

Glu Phe Asp Lys Lys Leu Val Ser Arg Ile Gln Ile Arg Val Asn Pro
                100                 105                 110

Leu Pro Lys Phe Asp Ser Thr Val Trp Val Thr Val Arg Lys Val Pro
            115                 120                 125

Ala Ser Ser Asp Leu Ser Val Ala Ala Ile Ser Ala Met Phe Ala Asp
130                 135                 140

Gly Ala Ser Pro Val Leu Val Tyr Gln Tyr Ala Ala Ser Gly Val Gln
145                 150                 155                 160

Ala Asn Asn Lys Leu Leu Tyr Asp Leu Ser Ala Met Arg Ala Asp Ile
                165                 170                 175

Gly Asp Met Arg Lys Tyr Ala Val Leu Val Tyr Ser Lys Asp Asp Ala
                180                 185                 190

Leu Glu Thr Asp Glu Leu Val Leu His Val Asp Ile Glu His Gln Arg
            195                 200                 205

Ile Pro Thr Ser Gly Val Leu Pro Val
            210                 215

<210> SEQ ID NO 17
<211> LENGTH: 218
<212> TYPE: PRT
<213> ORGANISM: cucumber mosaic virus

<400> SEQUENCE: 17

Met Asp Lys Ser Glu Ser Pro Asn Ala Ser Arg Thr Ser Arg Arg Arg
1               5                   10                  15

Arg Pro Arg Arg Gly Ser Arg Ser Ala Ser Gly Ala Asp Ala Gly Leu
            20                  25                  30

Arg Ala Leu Thr Gln Gln Met Leu Lys Leu Asn Lys Thr Leu Ala Ile
            35                  40                  45

Gly Arg Pro Thr Leu Asn His Pro Thr Phe Val Gly Ser Ala Ser Cys
50                  55                  60

Lys Pro Gly Tyr Thr Phe Thr Ser Ile Thr Leu Lys Pro Pro Glu Ile
65                  70                  75                  80

Glu Lys Gly Ser Tyr Phe Gly Arg Arg Leu Ser Leu Pro Asp Ser Val
                85                  90                  95

Thr Asp Tyr Asp Lys Lys Leu Val Ser Arg Ile Gln Ile Arg Ile Asn
                100                 105                 110

Pro Leu Pro Lys Phe Asp Ser Thr Val Trp Val Thr Val Arg Lys Val
            115                 120                 125
```

```
Pro Ser Ser Ser Asp Leu Ser Val Ala Thr Ile Ser Ala Met Phe Gly
        130                 135                 140

Asp Gly Asn Ser Pro Val Leu Val Tyr Gln Tyr Thr Ala Ser Gly Val
145                 150                 155                 160

Gln Ala Asn Asn Lys Leu Leu Tyr Asp Leu Ser Glu Met Arg Ala Asp
                165                 170                 175

Ile Gly Asp Met Arg Lys Tyr Ala Val Leu Val Tyr Ser Lys Asp Asp
            180                 185                 190

Lys Leu Glu Glu Asp Glu Ile Val Leu His Val Asp Val Glu His Gln
        195                 200                 205

Arg Ile Pro Ile Ser Arg Met Leu Pro Thr
    210                 215

<210> SEQ ID NO 18
<211> LENGTH: 14
<212> TYPE: PRT
<213> ORGANISM: artificial sequence
<220> FEATURE:
<223> OTHER INFORMATION: tetanus toxoid epitope tt830

<400> SEQUENCE: 18

Gln Tyr Ile Lys Ala Asn Ser Lys Phe Ile Gly Ile Thr Glu
1               5                   10

<210> SEQ ID NO 19
<211> LENGTH: 13
<212> TYPE: PRT
<213> ORGANISM: artificial sequence
<220> FEATURE:
<223> OTHER INFORMATION: PADRE

<400> SEQUENCE: 19

Ala Lys Phe Val Ala Ala Trp Thr Leu Lys Ala Ala Ala
1               5                   10

<210> SEQ ID NO 20
<211> LENGTH: 222
<212> TYPE: PRT
<213> ORGANISM: artificial sequence
<220> FEATURE:
<223> OTHER INFORMATION: CMV-Ntt830

<400> SEQUENCE: 20

Met Gly Gln Tyr Ile Lys Ala Asn Ser Lys Phe Ile Gly Ile Thr Glu
1               5                   10                  15

Arg Arg Arg Arg Pro Arg Arg Gly Ser Arg Ala Pro Ser Ser Ala
                20                  25                  30

Asp Ala Asn Phe Arg Val Leu Ser Gln Gln Leu Ser Arg Leu Asn Lys
            35                  40                  45

Thr Leu Ala Ala Gly Arg Pro Thr Ile Asn His Pro Thr Phe Val Gly
        50                  55                  60

Ser Glu Arg Cys Lys Pro Gly Tyr Thr Phe Thr Ser Ile Thr Leu Lys
65                  70                  75                  80

Pro Pro Lys Ile Asp Arg Gly Ser Tyr Tyr Gly Lys Arg Leu Leu Leu
                85                  90                  95

Pro Asp Ser Val Thr Glu Tyr Asp Lys Lys Leu Val Ser Arg Ile Gln
            100                 105                 110

Ile Arg Val Asn Pro Leu Pro Lys Phe Asp Ser Thr Val Trp Val Thr
        115                 120                 125
```

```
Val Arg Lys Val Pro Ala Ser Ser Asp Leu Ser Val Ala Ala Ile Ser
    130                 135                 140

Ala Met Phe Ala Asp Gly Ala Ser Pro Val Leu Val Tyr Gln Tyr Ala
145                 150                 155                 160

Ala Ser Gly Val Gln Ala Asn Asn Lys Leu Leu Tyr Asp Leu Ser Ala
                165                 170                 175

Met Arg Ala Asp Ile Gly Asp Met Arg Lys Tyr Ala Val Leu Val Tyr
                180                 185                 190

Ser Lys Asp Asp Ala Leu Glu Thr Asp Glu Leu Val Leu His Val Asp
            195                 200                 205

Val Glu His Gln Arg Ile Pro Thr Ser Gly Val Leu Pro Val
    210                 215                 220
```

<210> SEQ ID NO 21
<211> LENGTH: 220
<212> TYPE: PRT
<213> ORGANISM: artificial sequence
<220> FEATURE:
<223> OTHER INFORMATION: CMV-Npadr

<400> SEQUENCE: 21

```
Met Ala Lys Phe Val Ala Ala Trp Thr Leu Lys Ala Ala Arg Arg
1               5                   10                  15

Arg Arg Pro Arg Arg Gly Ser Arg Ser Ala Pro Ser Ser Ala Asp Ala
                20                  25                  30

Asn Phe Arg Val Leu Ser Gln Gln Leu Ser Arg Leu Asn Lys Thr Leu
            35                  40                  45

Ala Ala Gly Arg Pro Thr Ile Asn His Pro Thr Phe Val Gly Ser Glu
50                  55                  60

Arg Cys Lys Pro Gly Tyr Thr Phe Thr Ser Ile Thr Leu Lys Pro Pro
65                  70                  75                  80

Lys Ile Asp Arg Gly Ser Tyr Tyr Gly Lys Arg Leu Leu Leu Pro Asp
                85                  90                  95

Ser Val Thr Glu Tyr Asp Lys Lys Leu Val Ser Arg Ile Gln Ile Arg
            100                 105                 110

Val Asn Pro Leu Pro Lys Phe Asp Ser Thr Val Trp Val Thr Val Arg
        115                 120                 125

Lys Val Pro Ala Ser Ser Asp Leu Ser Val Ala Ala Ile Ser Ala Met
130                 135                 140

Phe Ala Asp Gly Ala Ser Pro Val Leu Val Tyr Gln Tyr Ala Ala Ser
145                 150                 155                 160

Gly Val Gln Ala Asn Asn Lys Leu Leu Tyr Asp Leu Ser Ala Met Arg
                165                 170                 175

Ala Asp Ile Gly Asp Met Arg Lys Tyr Ala Val Leu Val Tyr Ser Lys
            180                 185                 190

Asp Asp Ala Leu Glu Thr Asp Glu Leu Val Leu His Val Asp Val Glu
        195                 200                 205

His Gln Arg Ile Pro Thr Ser Gly Val Leu Pro Val
    210                 215                 220
```

<210> SEQ ID NO 22
<211> LENGTH: 34
<212> TYPE: DNA
<213> ORGANISM: artificial sequence
<220> FEATURE:
<223> OTHER INFORMATION: primer CMcpF

<400> SEQUENCE: 22

```
caccatggac aaatctgaat caaccagtgc tggt                                    34
```

<210> SEQ ID NO 23
<211> LENGTH: 37
<212> TYPE: DNA
<213> ORGANISM: artificial sequence
<220> FEATURE:
<223> OTHER INFORMATION: primer CMcpR

<400> SEQUENCE: 23

```
caaagcttat caaactggga gcaccccaga tgtggga                                 37
```

<210> SEQ ID NO 24
<211> LENGTH: 660
<212> TYPE: DNA
<213> ORGANISM: cucumber mosaic virus

<400> SEQUENCE: 24

```
atggacaaat ctgaatcaac cagtgctggt cgtagccgtc gacgtcgtcc gcgtcgtggt        60
tcccgctccg cccccctcct cgcggatgct aactttagag tcttgtcgca gcagctttcg       120
cgacttaata agacgttagc agctggtcgt ccaactatta accacccaac ctttgtaggg       180
agtgaacgct gtaaacctgg gtacacgttc acatctatca ccctaaagcc accaaaaata       240
gaccgtgggt cttattatgg taaaaggttg ttattacctg attcagtcac ggaatatgat       300
aagaaacttg tttcgcgcat tcaaattcga gttaatcctt gccgaaaatt tgattcaacc       360
gtgtgggtga cagtccgtaa agttcctgcc tcttcggact tatccgttgc cgccattct        420
gctatgtttg cggacggagc ctcaccggta ctggtttatc agtacgctgc atctggagtc       480
caagctaaca caaactgtt gtatgatctt tcggcgatgc gcgctgatat aggcgacatg        540
agaaagtacg ccgtcctcgt gtattcaaaa gacgatgcac tcgagacaga cgagttagta       600
cttcatgttg acgtcgagca ccaacgtatt cccacatctg gggtgctccc agtttgataa       660
```

<210> SEQ ID NO 25
<211> LENGTH: 20
<212> TYPE: DNA
<213> ORGANISM: artificial sequence
<220> FEATURE:
<223> OTHER INFORMATION: primer pET-220

<400> SEQUENCE: 25

```
agcaccgccg ccgcaaggaa                                                    20
```

<210> SEQ ID NO 26
<211> LENGTH: 52
<212> TYPE: DNA
<213> ORGANISM: artificial sequence
<220> FEATURE:
<223> OTHER INFORMATION: primer CMV-tt83-1R

<400> SEQUENCE: 26

```
atttggagtt ggccttaata tactggccca tggtatatct ccttcttaaa gt               52
```

<210> SEQ ID NO 27
<211> LENGTH: 52
<212> TYPE: DNA
<213> ORGANISM: artificial sequence
<220> FEATURE:
<223> OTHER INFORMATION: primer CMV-tt83Sal-R2

<400> SEQUENCE: 27

```
gacgtcgacg ctcggtaatc ccgataaatt tggagttggc cttaatatac tg          52
```

<210> SEQ ID NO 28
<211> LENGTH: 672
<212> TYPE: DNA
<213> ORGANISM: artificial sequence
<220> FEATURE:
<223> OTHER INFORMATION: cDNA coding for CMV-Ntt830

<400> SEQUENCE: 28

```
atgggccagt atattaaggc caactccaaa tttatcggga ttaccgagcg tcgacgtcgt    60
ccgcgtcgtg gttcccgctc cgcccctcc tccgcggatg ctaactttag agtcttgtcg   120
cagcagcttt cgcgacttaa taagacgtta gcagctggtc gtccaactat taaccaccca   180
acctttgtag ggagtgaacg ctgtaaacct gggtacacgt tcacatctat caccctaaag   240
ccaccaaaaa tagaccgtgg gtcttattat ggtaaaaggt tgttattacc tgattcagtc   300
acggaatatg ataagaaact tgtttcgcgc attcaaattc gagttaatcc tttgccgaaa   360
tttgattcaa ccgtgtgggt gacagtccgt aaagttcctg cctcttcgga cttatccgtt   420
gccgccattt ctgctatgtt tgcggacgga gcctcaccgg tactggttta tcagtacgct   480
gcatctggag tccaagctaa caacaaactg ttgtatgatc tttcggcgat gcgcgctgat   540
ataggcgaca tgagaaagta cgccgtcctc gtgtattcaa agacgatgc actcgagaca   600
gacgagttag tacttcatgt tgacgtcgag caccaacgta ttcccacatc tggggtgctc   660
ccagtttgat aa                                                     672
```

<210> SEQ ID NO 29
<211> LENGTH: 55
<212> TYPE: DNA
<213> ORGANISM: artificial sequence
<220> FEATURE:
<223> OTHER INFORMATION: primer CMV-padrSal-R

<400> SEQUENCE: 29

```
gacgtcgacg cgcggccgcc ttgagggtcc acgcggccac aaatttcgcc atggt       55
```

<210> SEQ ID NO 30
<211> LENGTH: 666
<212> TYPE: DNA
<213> ORGANISM: artificial sequence
<220> FEATURE:
<223> OTHER INFORMATION: cDNA coding for CMV-Npadr

<400> SEQUENCE: 30

```
atggcgaaat ttgtggccgc gtggaccctc aaggcggccg cgcgtcgacg tcgtccgcgt    60
cgtggttccc gctccgcccc ctcctccgcg gatgctaact ttagagtctt gtcgcagcag   120
ctttcgcgac ttaataagac gttagcagct ggtcgtccaa ctattaacca cccaaccttt   180
gtagggagtg aacgctgtaa acctgggtac acgttcacat ctatcaccct aaagccacca   240
aaaatagacc gtgggtctta ttatggtaaa aggttgttat acctgattc agtcacggaa   300
tatgataaga aacttgtttc gcgcattcaa attcgagtta atcctttgcc gaaatttgat   360
tcaaccgtgt gggtgacagt ccgtaaagtt cctgcctctt cggacttatc cgttgccgcc   420
atttctgcta tgtttgcgga cggagcctca ccggtactgg tttatcagta cgctgcatct   480
ggagtccaag ctaacaacaa actgttgtat gatctttcgg cgatgcgcgc tgatataggc   540
gacatgagaa agtacgccgt cctcgtgtat tcaaagacg atgcactcga dacagacgag   600
ttagtacttc atgttgacgt cgagcaccaa cgtattccca catctggggt gctcccagtt   660
```

-continued tgataa 666

<210> SEQ ID NO 31
<211> LENGTH: 132
<212> TYPE: PRT
<213> ORGANISM: Bacteriophage Q-beta

<400> SEQUENCE: 31

Ala Lys Leu Glu Thr Val Thr Leu Gly Asn Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Ala Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
    130

<210> SEQ ID NO 32
<211> LENGTH: 329
<212> TYPE: PRT
<213> ORGANISM: Bacteriophage Q-beta

<400> SEQUENCE: 32

Met Ala Lys Leu Glu Thr Val Thr Leu Gly Asn Ile Gly Lys Asp Gly
1               5                   10                  15

Lys Gln Thr Leu Val Leu Asn Pro Arg Gly Val Asn Pro Thr Asn Gly
            20                  25                  30

Val Ala Ser Leu Ser Gln Ala Gly Ala Val Pro Ala Leu Glu Lys Arg
        35                  40                  45

Val Thr Val Ser Val Ser Gln Pro Ser Arg Asn Arg Lys Asn Tyr Lys
    50                  55                  60

Val Gln Val Lys Ile Gln Asn Pro Thr Ala Cys Thr Ala Asn Gly Ser
65                  70                  75                  80

Cys Asp Pro Ser Val Thr Arg Gln Ala Tyr Ala Asp Val Thr Phe Ser
                85                  90                  95

Phe Thr Gln Tyr Ser Thr Asp Glu Glu Arg Ala Phe Val Arg Thr Glu
            100                 105                 110

Leu Ala Ala Leu Leu Ala Ser Pro Leu Leu Ile Asp Ala Ile Asp Gln
        115                 120                 125

Leu Asn Pro Ala Tyr Trp Thr Leu Leu Ile Ala Gly Gly Gly Ser Gly
    130                 135                 140

Ser Lys Pro Asp Pro Val Ile Pro Asp Pro Ile Asp Pro Pro
145                 150                 155                 160

Gly Thr Gly Lys Tyr Thr Cys Pro Phe Ala Ile Trp Ser Leu Glu Glu
                165                 170                 175

```
Val Tyr Glu Pro Pro Thr Lys Asn Arg Pro Trp Pro Ile Tyr Asn Ala
            180                 185                 190

Val Glu Leu Gln Pro Arg Glu Phe Asp Val Ala Leu Lys Asp Leu Leu
        195                 200                 205

Gly Asn Thr Lys Trp Arg Asp Trp Asp Ser Arg Leu Ser Tyr Thr Thr
    210                 215                 220

Phe Arg Gly Cys Arg Gly Asn Gly Tyr Ile Asp Leu Asp Ala Thr Tyr
225                 230                 235                 240

Leu Ala Thr Asp Gln Ala Met Arg Asp Gln Lys Tyr Asp Ile Arg Glu
                245                 250                 255

Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
                325

<210> SEQ ID NO 33
<211> LENGTH: 131
<212> TYPE: PRT
<213> ORGANISM: Bacteriophage AP205

<400> SEQUENCE: 33

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 34
<211> LENGTH: 27
<212> TYPE: PRT
<213> ORGANISM: artificial sequence
<220> FEATURE:
<223> OTHER INFORMATION: aa 2-28 of SEQ ID NO:15

<400> SEQUENCE: 34

Asp Lys Ser Glu Ser Thr Ser Ala Gly Arg Ser Arg Arg Arg Arg Pro
1               5                   10                  15

Arg Arg Gly Ser Arg Ser Ala Pro Ser Ser Ala
            20                  25
```

<210> SEQ ID NO 35
<211> LENGTH: 128
<212> TYPE: PRT
<213> ORGANISM: artificial sequence
<220> FEATURE:
<223> OTHER INFORMATION: eIL-5 mature protein fragment var1

<400> SEQUENCE: 35

Met Ala Val Glu Ser Pro Met Asn Arg Leu Val Ala Glu Thr Leu Thr
1               5                   10                  15

Leu Leu Ser Thr His Arg Thr Leu Leu Ile Gly Asp Gly Asn Leu Met
            20                  25                  30

Ile Pro Thr Pro Glu His Lys Asn His Gln Leu Cys Ile Glu Glu Val
        35                  40                  45

Phe Gln Gly Ile Asp Thr Leu Lys Asn Gln Thr Val Gln Gly Asp Ala
    50                  55                  60

Val Ala Lys Leu Phe Gln Asn Leu Ser Leu Ile Lys Gly Tyr Ile Asp
65                  70                  75                  80

Leu Gln Lys Lys Lys Cys Gly Gly Glu Arg Trp Arg Val Lys Gln Phe
                85                  90                  95

Leu Asp Tyr Leu Gln Glu Phe Leu Gly Val Ile Asn Thr Glu Trp Thr
            100                 105                 110

Ile Glu Gly Gly Gly Cys Leu Glu His His His His His His His
            115                 120                 125

<210> SEQ ID NO 36
<211> LENGTH: 125
<212> TYPE: PRT
<213> ORGANISM: artificial sequence
<220> FEATURE:
<223> OTHER INFORMATION: eIL-5 mature protein fragment var2

<400> SEQUENCE: 36

Met Leu Ala Val Glu Ser Pro Met Asn Arg Leu Val Ala Glu Thr Leu
1               5                   10                  15

Thr Leu Leu Ser Thr His Arg Thr Leu Leu Ile Gly Asp Gly Asn Leu
            20                  25                  30

Met Ile Pro Thr Pro Glu His Lys Asn His Gln Leu Cys Ile Glu Glu
        35                  40                  45

Val Phe Gln Gly Ile Asp Thr Leu Lys Asn Gln Thr Val Gln Gly Asp
    50                  55                  60

Ala Val Ala Lys Leu Phe Gln Asn Leu Ser Leu Ile Lys Gly Tyr Ile
65                  70                  75                  80

Asp Leu Gln Lys Lys Lys Cys Gly Gly Glu Arg Trp Arg Val Lys Gln
                85                  90                  95

Phe Leu Asp Tyr Leu Gln Glu Phe Leu Gly Val Ile Asn Thr Glu Trp
            100                 105                 110

Thr Ile Glu Gly Gly Gly Cys His His His His His His
            115                 120                 125

<210> SEQ ID NO 37
<211> LENGTH: 125
<212> TYPE: PRT
<213> ORGANISM: artificial sequence
<220> FEATURE:
<223> OTHER INFORMATION: eIL-5 mature protein fragment var3

<400> SEQUENCE: 37

Met Gly Gly Cys Leu Ala Val Glu Ser Pro Met Asn Arg Leu Val Ala
1               5                   10                  15

Glu Thr Leu Thr Leu Leu Ser Thr His Arg Thr Leu Leu Ile Gly Asp
            20                  25                  30

Gly Asn Leu Met Ile Pro Thr Pro Glu His Lys Asn His Gln Leu Cys
        35                  40                  45

Ile Glu Glu Val Phe Gln Gly Ile Asp Thr Leu Lys Asn Gln Thr Val
    50                  55                  60

Gln Gly Asp Ala Val Ala Lys Leu Phe Gln Asn Leu Ser Leu Ile Lys
65                  70                  75                  80

Gly Tyr Ile Asp Leu Gln Lys Lys Lys Cys Gly Gly Glu Arg Trp Arg
                85                  90                  95

Val Lys Gln Phe Leu Asp Tyr Leu Gln Glu Phe Leu Gly Val Ile Asn
            100                 105                 110

Thr Glu Trp Thr Ile Glu Gly His His His His His
            115                 120                 125

<210> SEQ ID NO 38
<211> LENGTH: 119
<212> TYPE: PRT
<213> ORGANISM: artificial sequence
<220> FEATURE:
<223> OTHER INFORMATION: eIL-5 mature protein fragment var4

<400> SEQUENCE: 38

Met Gly Gly Cys Leu Ala Val Glu Ser Pro Met Asn Arg Leu Val Ala
1               5                   10                  15

Glu Thr Leu Thr Leu Leu Ser Thr His Arg Thr Leu Leu Ile Gly Asp
            20                  25                  30

Gly Asn Leu Met Ile Pro Thr Pro Glu His Lys Asn His Gln Leu Cys
        35                  40                  45

Ile Glu Glu Val Phe Gln Gly Ile Asp Thr Leu Lys Asn Gln Thr Val
    50                  55                  60

Gln Gly Asp Ala Val Ala Lys Leu Phe Gln Asn Leu Ser Leu Ile Lys
65                  70                  75                  80

Gly Tyr Ile Asp Leu Gln Lys Lys Lys Cys Gly Gly Glu Arg Trp Arg
                85                  90                  95

Val Lys Gln Phe Leu Asp Tyr Leu Gln Glu Phe Leu Gly Val Ile Asn
            100                 105                 110

Thr Glu Trp Thr Ile Glu Gly
            115

<210> SEQ ID NO 39
<211> LENGTH: 90
<212> TYPE: PRT
<213> ORGANISM: artificial sequence
<220> FEATURE:
<223> OTHER INFORMATION: eEotaxin mature fragment var1

<400> SEQUENCE: 39

Met Pro Val Ser Ile Ser Thr Val Cys Cys Phe Asn Val Ala Ser Arg
1               5                   10                  15

Lys Ile Ser Phe Gln Arg Leu Gln Ser Tyr Arg Lys Ile Thr Ser Ser
            20                  25                  30

Lys Cys Pro Gln Lys Ala Val Ile Phe Lys Thr Lys Gln Ala Lys Lys
        35                  40                  45

Ile Cys Ala Asp Pro Lys Gln Lys Trp Val Gln Asp Ala Met Lys Tyr

```
                    50                  55                  60

Leu Asp Glu Asn Ser Arg Thr Thr Lys Tyr Ser Ser Phe Gly Gly Cys
 65                  70                  75                  80

Leu Glu His His His His His His His
                85                  90

<210> SEQ ID NO 40
<211> LENGTH: 87
<212> TYPE: PRT
<213> ORGANISM: artificial sequence
<220> FEATURE:
<223> OTHER INFORMATION: eEotaxin mature protein fragment var2

<400> SEQUENCE: 40

Met Gln Pro Val Ser Ile Ser Thr Val Cys Cys Phe Asn Val Ala Ser
 1                5                  10                  15

Arg Lys Ile Ser Phe Gln Arg Leu Gln Ser Tyr Arg Lys Ile Thr Ser
                20                  25                  30

Ser Lys Cys Pro Gln Lys Ala Val Ile Phe Lys Thr Lys Gln Ala Lys
            35                  40                  45

Lys Ile Cys Ala Asp Pro Lys Gln Lys Trp Val Gln Asp Ala Met Lys
 50                  55                  60

Tyr Leu Asp Glu Asn Ser Arg Thr Thr Lys Tyr Ser Ser Phe Gly Gly
 65                  70                  75                  80

Cys His His His His His His
                85

<210> SEQ ID NO 41
<211> LENGTH: 87
<212> TYPE: PRT
<213> ORGANISM: artificial sequence
<220> FEATURE:
<223> OTHER INFORMATION: eEotaxin mature protein fragment var4

<400> SEQUENCE: 41

Met Gly Gly Cys Gln Pro Val Ser Ile Ser Thr Val Cys Cys Phe Asn
 1                5                  10                  15

Val Ala Ser Arg Lys Ile Ser Phe Gln Arg Leu Gln Ser Tyr Arg Lys
                20                  25                  30

Ile Thr Ser Ser Lys Cys Pro Gln Lys Ala Val Ile Phe Lys Thr Lys
            35                  40                  45

Gln Ala Lys Lys Ile Cys Ala Asp Pro Lys Gln Lys Trp Val Gln Asp
 50                  55                  60

Ala Met Lys Tyr Leu Asp Glu Asn Ser Arg Thr Thr Lys Tyr Ser Ser
 65                  70                  75                  80

Phe His His His His His His
                85

<210> SEQ ID NO 42
<211> LENGTH: 81
<212> TYPE: PRT
<213> ORGANISM: artificial sequence
<220> FEATURE:
<223> OTHER INFORMATION: eEotaxin mature protein fragment var4

<400> SEQUENCE: 42

Met Gly Gly Cys Gln Pro Val Ser Ile Ser Thr Val Cys Cys Phe Asn
 1                5                  10                  15

Val Ala Ser Arg Lys Ile Ser Phe Gln Arg Leu Gln Ser Tyr Arg Lys
                20                  25                  30
```

```
Ile Thr Ser Ser Lys Cys Pro Gln Lys Ala Val Ile Phe Lys Thr Lys
         35                  40                  45

Gln Ala Lys Lys Ile Cys Ala Asp Pro Lys Gln Lys Trp Val Gln Asp
 50                  55                  60

Ala Met Lys Tyr Leu Asp Glu Asn Ser Arg Thr Thr Lys Tyr Ser Ser
 65                  70                  75                  80

Phe

<210> SEQ ID NO 43
<211> LENGTH: 137
<212> TYPE: PRT
<213> ORGANISM: artificial sequence
<220> FEATURE:
<223> OTHER INFORMATION: eIL-31 mature protein fragment var1

<400> SEQUENCE: 43

Met Gly Pro Ile Tyr Gln Leu Gln Pro Lys Glu Ile Gln Ala Ile Ile
 1               5                  10                  15

Val Glu Leu Gln Asn Leu Ser Lys Lys Leu Leu Asp Asp Tyr Leu Asn
             20                  25                  30

Lys Glu Lys Gly Val Gln Lys Phe Asp Ser Asp Leu Pro Ser Cys Phe
         35                  40                  45

Thr Ser Asp Ser Gln Ala Pro Gly Asn Ile Asn Ser Ser Ala Ile Leu
 50                  55                  60

Pro Tyr Phe Lys Ala Ile Ser Pro Ser Leu Asn Asn Asp Lys Ser Leu
 65                  70                  75                  80

Tyr Ile Ile Glu Gln Leu Asp Lys Leu Asn Phe Gln Asn Ala Pro Glu
             85                  90                  95

Thr Glu Val Ser Met Pro Thr Asp Asn Phe Glu Arg Lys Arg Phe Ile
            100                 105                 110

Leu Thr Ile Leu Arg Trp Phe Ser Asn Cys Leu Glu Gly Gly Cys Leu
        115                 120                 125

Glu His His His His His His His
            130                 135

<210> SEQ ID NO 44
<211> LENGTH: 133
<212> TYPE: PRT
<213> ORGANISM: artificial sequence
<220> FEATURE:
<223> OTHER INFORMATION: eIL-31 mature protein fragment var2

<400> SEQUENCE: 44

Met Gly Pro Ile Tyr Gln Leu Gln Pro Lys Glu Ile Gln Ala Ile Ile
 1               5                  10                  15

Val Glu Leu Gln Asn Leu Ser Lys Lys Leu Leu Asp Asp Tyr Leu Asn
             20                  25                  30

Lys Glu Lys Gly Val Gln Lys Phe Asp Ser Asp Leu Pro Ser Cys Phe
         35                  40                  45

Thr Ser Asp Ser Gln Ala Pro Gly Asn Ile Asn Ser Ser Ala Ile Leu
 50                  55                  60

Pro Tyr Phe Lys Ala Ile Ser Pro Ser Leu Asn Asn Asp Lys Ser Leu
 65                  70                  75                  80

Tyr Ile Ile Glu Gln Leu Asp Lys Leu Asn Phe Gln Asn Ala Pro Glu
             85                  90                  95

Thr Glu Val Ser Met Pro Thr Asp Asn Phe Glu Arg Lys Arg Phe Ile
            100                 105                 110
```

Leu Thr Ile Leu Arg Trp Phe Ser Asn Cys Leu Glu His His His
        115                 120                 125

His His Gly Gly Cys
        130

<210> SEQ ID NO 45
<211> LENGTH: 133
<212> TYPE: PRT
<213> ORGANISM: artificial sequence
<220> FEATURE:
<223> OTHER INFORMATION: eIL-31 mature protein fragment var3

<400> SEQUENCE: 45

Met Gly Gly Cys Gly Pro Ile Tyr Gln Leu Gln Pro Lys Glu Ile Gln
1               5                   10                  15

Ala Ile Ile Val Glu Leu Gln Asn Leu Ser Lys Leu Leu Asp Asp
                20                  25                  30

Tyr Leu Asn Lys Glu Lys Gly Val Gln Lys Phe Asp Ser Asp Leu Pro
            35                  40                  45

Ser Cys Phe Thr Ser Asp Ser Gln Ala Pro Gly Asn Ile Asn Ser Ser
    50                  55                  60

Ala Ile Leu Pro Tyr Phe Lys Ala Ile Ser Pro Ser Leu Asn Asn Asp
65                  70                  75                  80

Lys Ser Leu Tyr Ile Ile Glu Gln Leu Asp Lys Leu Asn Phe Gln Asn
                85                  90                  95

Ala Pro Glu Thr Glu Val Ser Met Pro Thr Asp Asn Phe Glu Arg Lys
            100                 105                 110

Arg Phe Ile Leu Thr Ile Leu Arg Trp Phe Ser Asn Cys Leu Glu His
        115                 120                 125

His His His His His
        130

<210> SEQ ID NO 46
<211> LENGTH: 127
<212> TYPE: PRT
<213> ORGANISM: artificial sequence
<220> FEATURE:
<223> OTHER INFORMATION: eIL-31 mature protein fragment var4

<400> SEQUENCE: 46

Met Gly Gly Cys Gly Pro Ile Tyr Gln Leu Gln Pro Lys Glu Ile Gln
1               5                   10                  15

Ala Ile Ile Val Glu Leu Gln Asn Leu Ser Lys Leu Leu Asp Asp
                20                  25                  30

Tyr Leu Asn Lys Glu Lys Gly Val Gln Lys Phe Asp Ser Asp Leu Pro
            35                  40                  45

Ser Cys Phe Thr Ser Asp Ser Gln Ala Pro Gly Asn Ile Asn Ser Ser
    50                  55                  60

Ala Ile Leu Pro Tyr Phe Lys Ala Ile Ser Pro Ser Leu Asn Asn Asp
65                  70                  75                  80

Lys Ser Leu Tyr Ile Ile Glu Gln Leu Asp Lys Leu Asn Phe Gln Asn
                85                  90                  95

Ala Pro Glu Thr Glu Val Ser Met Pro Thr Asp Asn Phe Glu Arg Lys
            100                 105                 110

Arg Phe Ile Leu Thr Ile Leu Arg Trp Phe Ser Asn Cys Leu Glu
        115                 120                 125